(12) United States Patent
El-Boubbou et al.

(10) Patent No.: US 11,318,214 B2
(45) Date of Patent: May 3, 2022

(54) IRON OXIDE MESOPOROUS MICROPARTICLE DRUG CARRIER

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Kheireddine El-Boubbou, Riyadh (SA); Rizwan Ali, Riyadh (SA); Abdulmohsen Alkushi, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 0 days.

(21) Appl. No.: 16/909,501

(22) Filed: Jun. 23, 2020

(65) Prior Publication Data
US 2021/0393798 A1  Dec. 23, 2021

(51) Int. Cl.
*A61K 47/69* (2017.01)
*A61K 31/138* (2006.01)
*A61K 31/704* (2006.01)

(52) U.S. Cl.
CPC ...... *A61K 47/6929* (2017.08); *A61K 47/6923* (2017.08); *A61K 31/138* (2013.01); *A61K 31/704* (2013.01)

(58) Field of Classification Search
None
See application file for complete search history.

(56) References Cited

U.S. PATENT DOCUMENTS

| | | | |
|---|---|---|---|
| 10,493,098 B2 | 12/2019 | Haynes et al. | |
| 10,561,747 B1 | 2/2020 | Ayyub et al. | |
| 2020/0038525 A1 | 2/2020 | Jermy et al. | |

FOREIGN PATENT DOCUMENTS

| | | |
|---|---|---|
| CN | 104069513 A | 10/2014 |
| CN | 109679144 A | 4/2019 |

OTHER PUBLICATIONS

Benyettou et al., "Mesoporous-Iron Oxide Nanoparticles for Magnetically Triggered Release of Doxorubicin and Hyperthermia Treatment", Chem. Eur. J., 2016, 22, p. 17020-17028. (Year: 2016).*
Su et al., "Targeted Mesoporous Iron Oxide Nanoparticles-Encapsulated Perfluorohexane and a Hydrophobic Drug for Deep Tumor Penetration and Therapy", 2015, Theranostics, 5(11), pp. 1233-1248. (Year: 2015).*
Su et al., Supporting Information, 2015, Theranostics, 5(11), pp. 1-7 (Year: 2015).*
Li et al., "Functionalized Large-Pore Mesoporous Silica Microparticles for Gefitinib and Doxorubicin Codelivery", Materials 2019, 12, 766. (Year: 2019).*
Wang et al., "A nanomedicine based combination therapy based on QLPVM peptide functionalized liposomal tamoxifen and doxorubicin against Luminal A breast cancer", Nanomedicine: Nanotechnology, Biology and Medicine, 12(2), 2016, pp. 387-397. (Year: 2016).*
Jermy, et al. ; SPIONs/3D SiSBA-16 based Multifunctional Nanoformulation for target specific cisplatin release in colon and cervical cancer cell lines ; ScientificReports, natureresearch ; Oct. 10, 2019 ; 12 Pages.
Sen, et al. ; Simple one-pot fabrication of ultra-stable coreshell superparamagnetic nanoparticles for potential application in drug delivery ; RSC Advances, 2(12) ; pp. 5221-5228 ; 9 Pages.
Aval, et al. ; Doxoribicin loaded large-pore mesoporous hydroxoapatite coated superparamagnetic Fe3O4 nanoparticles for cancer treatment ; International Journal of Pharmaceutics, vol. 509, Issue 1-2 ; pp. 159-167 ; Abstract Only ; 2 Pages.
El-Boubbou, et al. ; Preparation of iron oxide mesoporous magnetic microparticles as novel multidrug carriers for synergistic anticancer therapy and deep tumor penetration ; Scientific Reports ; Jul. 1, 2019 ; 20 Pages.

* cited by examiner

*Primary Examiner* — Melissa L Fisher
(74) *Attorney, Agent, or Firm* — Oblon, McClelland, Maier & Neustadt, L.L.P.

(57) ABSTRACT

A magnetic microparticle drug carrier comprising mesoporous iron oxide is described. The drug carrier has an average diameter in a range of 0.5-1.2 μm, a BET surface area ranging from 50-300 m$^2$/g, and a pore volume ranging from 0.15-0.65 cm$^3$/g. The drug carrier is made using a hard mesoporous silica template which is completely removed from the deposited iron oxide. The drug carrier may be loaded with high amounts of hydrophilic anticancer chemotherapeutic drugs and/or hydrophobic hormonal anticancer drugs, and released in a pH-controlled manner inside cancerous cells. Compared to free drugs, the drug microparticle carrier displays enhanced drug accumulation inside tumor tissues, deeply penetrates into a tumor region and kills the tumor cells inside. The designed carriers described here entrap and release different kinds of anticancer drugs in a controlled manner for synergistic combinatorial chemo/hormonal cancer therapy.

15 Claims, 40 Drawing Sheets

Before Treatment     After Treatment

IRON OXIDE MESOPOROUS MICROPARTICLE DRUG CARRIER

STATEMENT REGARDING PRIOR DISCLOSURES BY THE INVENTORS

Aspects of this technology are described in "Preparation of iron oxide mesoporous magnetic microparticles as novel multidrug carriers for synergistic anticancer therapy and deep tumor penetration" by El-Boubbou, K.; Ali, R.; Al-Zahrani, H.; Trivilegio, T.; Alanazi, A. H.; Khan, A. L.; Boudjelal, M.; and AlKushi, A., in *Scientific Reports*, 9, 9481 (2019), DOI: 10.1038/s41598-019-46007-z, which is incorporated herein by reference in its entirety.

STATEMENT OF ACKNOWLEDGEMENT

This project was prepared through support by King Abdullah International Medical Research Center (KAIMRC) under grant RC13/204 and RC16/096, as well as support by KSAU-HS, NGHA, the core facility, and the Nanomedicine Department at KAIMRC.

BACKGROUND OF THE INVENTION

Technical Field

The present invention relates to a microparticle drug carrier comprising mesoporous iron oxide, and a method of use.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cancer therapy is a long-standing, formidable, and complex process. See Arruebo, M. et al. Assessment of the evolution of cancer treatment therapies. *Cancers* 3, 3279-3330 (2011), incorporated herein by reference in its entirety. In most cases, a single strategy such as chemotherapy, hormonal therapy, photothermal therapy, or immunotherapy alone is not sufficient to eradicate and eliminate tumors completely. The major challenge remains to establish an advanced carrier platform that can efficiently and selectively destroy cancer cells and penetrate deeply into tumor tissues, releasing their therapeutic payloads in a controlled manner. See Venditto, V. J. & Szoka, F. C. Jr. Cancer Nanomedicines: So Many Papers and So Few Drugs! *Adv. Drug. Del. Rev.* 65, 80-88 (2013); Sengupta, S. Cancer Nanomedicine: Lessons for Immuno-Oncology. *Trends in Cancer* 3, 551-560 (2017); Schroeder, A. et al. Treating metastatic cancer with nanotechnology. *Nat Rev. Cancer* 12, 39-50 (2012); and Jain, R. K. & Stylianopoulos, T. Delivering nanomedicine to solid tumors. *Nat. Rev. Clin. Oncol.* 7, 653-664 (2010), each incorporated herein by reference in their entirety. Consequently, examples of advanced drug delivery systems with chemo/photodynamic, immuno/photothermal, or chemo/immuno therapeutic combinations have been recently investigated with promising potentials in cancer treatment. See Guo, L. et al. Combinatorial Photothermal and Immuno Cancer Therapy Using Chitosan-Coated Hollow Copper Sulfide Nanoparticles. *ACS Nano* 8, 5670-5681 (2014); Tang, X.-L. et al. pH-Responsive Magnetic Mesoporous Silica-Based Nanoplatform for Synergistic Photodynamic Therapy/Chemotherapy. *ACS Appl. Mater. Interfaces* 10, 15001-15011 (2018); and Liu, Y. et al. Dual pH-responsive multifunctional nanoparticles for targeted treatment of breast cancer by combining immunotherapy and chemotherapy. *Acta Biomater.* 66, 310-324 (2018), each incorporated herein by reference in their entirety. Despite the many obstacles, however, developing formulations with controlled drug release and synergistic combination therapy should be the main strategy for intratumoural drug delivery and enhanced cancer therapeutics.

Of the various drug delivery systems established, mesoporous (having pores of 2 to 50 nm) platforms are especially attractive, due to their large surface areas, internal pore volumes, and tunable pore structures allowing large amounts of various drugs to be loaded into their pores at once and subsequently released on demand. See Rosenholm, J. M., Sahlgren, C. & Linden, M. Towards multifunctional, targeted drug delivery systems using mesoporous silica nanoparticles—opportunities & challenges. *Nanoscale* 2, 1870-1883 (2010); and Tiwari, G. et al. Drug delivery systems: An updated review. *Int. J. Pharm. Investig.* 2, 2-11 (2012), each incorporated herein by reference in their entirety. Besides, when the construct is further magnetic, the particles have promise in medicine, particularly as magneto-responsive drug delivery carriers. See El-Boubbou, K. Magnetic iron oxide nanoparticles as drug carriers: clinical relevance. *Nanomedicine* 13, 953-971 (2018), incorporated herein by reference in its entirety. In fact, hybrid mesoporous and/or magnetic carriers are gaining immense importance in improving cancer therapies. See Soler-Illia et al. Chemical Strategies To Design Textured Materials: from Microporous and Mesoporous Oxides to Nanonetworks and Hierarchical Structures. *Chem. Rev.* 102, 4093-4138 (2002); and Lee, J. E., Lee, N., Kim, T., Kim, J. & Hyeon, T. Multifunctional Mesoporous Silica Nanocomposite Nanoparticles for Theranostic Applications. *Acc. Chem. Res.* 44, 893-902 (2011), each incorporated herein by reference in their entirety. In this context, materials that respond to intracellular pH-driven stimulus have been shown to provide excellent spatial, temporal, and dosage control drug release from different types of carriers with reduced side toxicities, thus enhancing the efficacy of therapies. See Niedermayer, S. et al. Multifunctional polymer-capped mesoporous silica nanoparticles for pH-responsive targeted drug delivery. *Nanoscale* 7, 7953-7964 (2015); Zhao, Z. et al. Magnetite nanoparticles as smart carriers to manipulate the cytotoxicity of anticancer drugs: magnetic control and pH-responsive release. *J. Mater. Chem.* 22, 15717-15725 (2012); and Mura, S., Nicolas, J. & Couvreur, P. Stimuli-responsive nanocarriers for drug delivery. *Nat. Mater.* 12, 991-1003 (2013), each incorporated herein by reference in their entirety. Consequently, a pH-susceptible iron oxide-based mesoporous material, which is both magnetic and porous, employed as an antitumor platform for cancer therapy is highly desirable. Nonetheless, a means to synthesize high-quality mesoporous magnetic iron oxide materials with large surface areas and pore volumes remains elusive. Thus, preparation of mesoporous iron oxides with controllable physiochemical properties for drug delivery applications is not well established and is explored to a lesser extent. In fact, most mesoporous-based drug delivery systems focus either on mesoporous silica materials or hetero-structured materials, particularly composed of magnetic iron oxide nanoparticles (MNPs) coated with mesoporous silica shells (core/shell), loaded into hollow mesoporous silica nanosphere, or embedded in a mesoporous silica matrix. See Knežević, N. Ž., Ruiz-Hernández, E., Hennink, W. E. & Vallet-Regí, M. Magnetic mesoporous silica-based core/shell nanoparticles for biomedical applications. *RSC Adv.* 3, 9584-9593 (2013); Kim, J. et al. Multifunctional uniform nanoparticles composed of a magnetite nanocrystal core and a mesoporous silica shell for magnetic resonance and fluorescence imaging and for drug delivery. *Angew. Chem., Int. Ed.* 47, 8438-8441 (2008); Lu, F., Popa, A., Zhou, S., Zhu, J.-J. & Samia, A. C. S. Iron oxide-loaded hollow mesoporous silica nanocapsules for controlled drug release and hyperthermia. *Chem. Commun.* 49, 11436-11438 (2013); Gan, Q. et al. Endosomal pH-activatable magnetic nanoparticle-capped mesoporous silica for intracellular controlled release. *J. Mater. Chem.* 22, 15960-15968 (2012); Chen, D. Y. et al. Modification of magnetic silica/iron oxide nanocomposites with fluorescent polymethacrylic acid for cancer targeting and drug delivery. *J. Mater. Chem.* 20, 6422-6429 (2010); and Qiu, X.-L. et al. Sugar and pH dual-responsive snap-top nanocarriers based on mesoporous silica-coated $Fe_3O_4$ magnetic nanoparticles for cargo delivery. *Chem. Commun.* 51, 4237-4240 (2015), each incorporated herein by reference in their entirety. Reports on the utilization of mesoporous iron oxide nano/microstructures for therapeutic drug delivery applications are very rare. See Xuan, S. H. et al. Synthesis of Biocompatible, Mesoporous $Fe_3O_4$ Nano/Microspheres with Large Surface Area for Magnetic Resonance Imaging and Therapeutic Applications. *ACS Appl. Mater. Interfaces* 3, 237-244 (2011); Li, D. et al. Doxorubicin-Conjugated Mesoporous Magnetic Colloidal Nanocrystal Clusters Stabilized by Polysaccharide as a Smart Anticancer Drug Vehicle. *Small* 8, 2690-2697 (2012); and Benyettou, F. et al. Mesoporous γ-Iron Oxide Nanoparticles for Magnetically Triggered Release of Doxorubicin and Hyperthermia Treatment. *Chem. Eur. J.* 22, 17020-17028 (2016), each incorporated herein by reference in their entirety. Importantly, the multi-drug delivery using mesoporous magnetic constructs to deliver a combination of both hydrophilic and hydrophobic anticancer therapeutic drugs simultaneously has not been previously reported.

Methods of forming mesoporous silica, alumino-silicates, and related materials are well-known and rely on supramolecular arrays: micellar systems formed by anionic or cationic surfactants or block copolymers (mainly polyethylene-based polymers). See Firouzi, A. et al. Cooperative organization of inorganic-surfactant and biomimetic assemblies. *Science* 267, 1138-1143 (1995); and Soler-Illia, G., Crepaldi, E. L., Grosso, D. & Sanchez, C. Block copolymer-templated mesoporous oxides. *Curr. Opin. Colloid Interface Sci.* 8, 109-126 (2003), each incorporated herein by reference in their entirety. However, the synthesis of porous transition metal oxides, particularly iron oxides, has proven to be significantly more difficult and limited, with some important advances seen in recent decades. See Yang, P. D., Zhao, D. Y., Margolese, D. I., Chmelka, B. F. & Stucky, G. D. Generalized syntheses of large-pore mesoporous metal oxides with semicrystalline frameworks. *Nature* 396, 152-155 (1998); and Gu, D. & Schüth, F. Synthesis of non-siliceous mesoporous oxides. *Chem. Soc. Rev.* 43, 313-344 (2014), each incorporated herein by reference in their entirety. In general, other than the less-used solvothermal or hydrothermal methods which result in very poor porous materials, mesoporous metal oxide materials are most commonly prepared either via "soft-templating method" (templated by surfactants, block copolymers, colloids etc.) or by the "hard-templating method" (i.e. guest materials replicate the "inverse" or "surface" structures of the "host" inorganic materials), where an inverse replica is produced. See Li et al. (2012); Guo, S. J., Li, D., Zhang, L. M., Li, J. & Wang, E. K. Monodisperse mesoporous superparamagnetic single-crystal magnetite nanoparticles for drug delivery. *Biomaterials* 30, 1881-1889 (2009); Su, Y.-L. et al. Targeted Mesoporous Iron Oxide Nanoparticles-Encapsulated Perfluorohexane and a Hydrophobic Drug for Deep Tumor Penetration and Therapy. *Theranostics* 5, 1233-1248 (2015); Liu, X., Hu, Q., Fang, Z., Wu, Q. & Xie, Q. Carboxyl Enriched Monodisperse Porous $Fe_3O_4$ Nanoparticles with Extraordinary Sustained-Release Property. *Langmuir* 25, 7244-7248 (2009); Sanchez, C. et al. Designed hybrid organic-inorganic nanocomposites from functional nanobuilding blocks. *Chem. Mater.* 13, 3061-3083 (2001); Sun, B. et al. Synthesis of Mesoporous α-$Fe_2O_3$ Nanostructures for Highly Sensitive Gas Sensors and High Capacity Anode Materials in Lithium Ion Batteries. *J. Phys. Chem. C* 114, 18753-18761 (2010); Yang, P. D., Zhao, D. Y., Margolese, D. I., Chmelka, B. F. & Stucky, G. D. Block copolymer templating syntheses of mesoporous metal oxides with large ordering lengths and semicrystalline framework. *Chem. Mater.* 11, 2813-2826 (1999); Mitra, A., Vázquez-Vázquez, C., López-Quintela, M. A., Paul, B. K. & Bhaumik, A. Soft-templating approach for the synthesis of high surface area and superparamagnetic mesoporous iron oxide materials. *Micropor. Mesopor. Mat.* 131, 373-377 (2010); Delahaye, E. et al. "Nanocasting": Using SBA-15 silicas as hard templates to obtain ultrasmall monodispersed gamma-$Fe_2O_3$ nanoparticles. *J. Phys. Chem. B* 110, 26001-26011 (2006); Dong, A. G. et al. General synthesis of mesoporous spheres of metal oxides and phosphates. *J. Am. Chem. Soc.* 125, 4976-4977 (2003); Lu, A. H. et al. Spatially and Size Selective Synthesis of Fe-Based Nanoparticles on Ordered Mesoporous Supports as Highly Active and Stable Catalysts for Ammonia Decomposition. *J. Am. Chem. Soc.* 132, 14152-14162 (2010); and Deng, X., Chen, K. & Tüsysüz, H. Protocol for the Nanocasting Method: Preparation of Ordered Mesoporous Metal Oxides. *Chem. Mater.* 29, 40-52 (2017), each incorporated herein by reference in their entirety.

The utilization of hard templates for the preparation of mesoporous metal oxides has some advantages compared with soft templates, especially with respect to specific topological stability, veracity, predictability, controllability, and crystalline properties. See Jiao, F. et al. Ordered mesoporous $Fe_2O_3$ with crystalline walls. *J. Am. Chem. Soc.* 128, 5468-5474 (2006), incorporated herein by reference in its entirety. From the various hard templates employed (i.e. alumina membranes, latex spheres, carbon nanotubes, carbon-silica composites etc.), mesoporous silica has already displayed its power to incorporate different guests, which led to fabrication of a great variety of nanostructured composites, such as carbon, transition metals, and metal oxides. See Kleitz, F., Choi, S. H. & Ryoo, R. Cubic Ia3d large mesoporous silica: synthesis and replication to platinum nanowires, carbon nanorods and carbon nanotubes. *Chem. Commun.*, 2136-2137 (2003); Shin, H. J., Ryoo, R., Liu, Z. & Terasaki, O. Template Synthesis of Asymmetrically Mesostructured Platinum Networks. *J. Am. Chem. Soc.* 123, 1246-1247 (2001); Lu et al. (2010); Laha, S. C. & Ryoo, R. Synthesis of thermally stable mesoporous cerium oxide with nanocrystalline frameworks using mesoporous silica templates. *Chem. Commun.*, 2138-2139 (2003); Dickinson, C. et al. Formation Mechanism of Porous Single-Crystal $Cr_2O_3$ and $Co_3O_4$ Templated by Mesoporous Silica. *Chem. Mater.* 18, 3088-3095 (2006); Kim, S. S. et al. Preparation of Highly Ordered Mesoporous $TiO_2$ Materials with Crystalline Framework from Different Mesostructured Silica Templates via Nanoreplication. *Chem. Lett.* 37, 140-141 (2007); and Sun, X. et al. Container Effect in Nanocasting Synthesis of Mesoporous Metal Oxides. *J. Am. Chem. Soc.* 133, 14542-14545 (2011), each incorporated herein by reference in their entirety. Particularly, three-dimensional (3D) and two-dimensional (2D) mesoporous silica (i.e. KIT-6, SBA-15, MSU-H, MCM-41 etc.) with ordered or disordered mesopores and high internal pore surface area have proven to be an ideal host for the syntheses of such materials. See Jiao, F. et al. Synthesis of ordered mesoporous $Fe_3O_4$ and $\gamma$-$Fe_2O_3$ with crystalline walls using post-template reduction/oxidation. *J. Am. Chem. Soc.* 128, 12905-12909 (2006); Crowley, T. A. et al. Synthesis of metal and metal oxide nanowire and nanotube arrays within a mesoporous silica template. Chem. Mat. 15, 3518-3522 (2003); Yang, H. F. et al. One-step synthesis of highly ordered mesoporous silica monoliths with metal oxide nanocrystals in their channels. *Adv. Func. Mater.* 15, 1377-1384 (2005); Shon, J. K. et al. Synthesis of Mesoporous Iron Oxide Nanoparticles from Mesoporous Silica Template Via Nano-Replication. *Func. Mater. Lett.* 1, 151-154 (2008); and Shon, J. K. et al. Facile synthesis of highly ordered mesoporous silver using cubic mesoporous silica template with controlled surface hydrophobicity. *Chem. Commun.*, 650-652 (2009), each incorporated herein by reference in their entirety. Moreover, their thermal stability and high silanol density helps to incorporate inorganic metal precursors into their channels by sorption, phase transition, ion exchange, or grafting and, thus, form an inorganic framework by further thermal treatments. For instance, solutions of iron salts (i.e. $FeCl_3$ or $Fe(NO_3)_3$) are typically used as precursors that are either co-precipitated with the silica source or infiltrated into porous silica. See Fröba, M., Köhn, R., Bouffaud, G., Richard, 0. & van Tendeloo, G. $Fe_2O_3$ Nanoparticles within Mesoporous MCM-48 Silica: In Situ Formation and Characterization. *Chem. Mater.* 11, 2858-2865 (1999); and Samanta, S. et al. Synthesis and Characterization of Iron-Rich Highly Ordered Mesoporous Fe-MCM-41. *Ind. Eng. Chem. Res.* 42, 3012-3018 (2003), each incorporated herein by reference in their entirety. The subsequent drying and thermal treatment results in distribution of iron oxide nanoparticles inside the silica matrix, followed by final etching of the silica template to form the desired material. Using this nanocasting templated approach, mesoporous iron oxides ($Fe_2O_3$ or $Fe_3O_4$) with ordered and disordered crystalline walls have been prepared via impregnation of different iron concentrations into calcined mesostructured silica templates, mainly 3D bicontinuous KIT-6 and 2D hexagonally ordered SBA-15. See Jiao et al. Ordered mesoporous $Fe_2O_3$ with crystalline walls (2006); Jiao et al. Synthesis of ordered mesoporous $Fe_3O_4$ and $\gamma$-$Fe_2O_3$ with crystalline walls using post-template reduction/oxidation. (2006); Shon et al. (2008); Suteewong, T. et al. Ordered mesoporous silica nanoparticles with and without embedded iron oxide nanoparticles: structure evolution during synthesis. *J. Mater. Chem.* 20, 7807-7814 (2010); and Tsoncheva, T. et al. Critical evaluation of the state of iron oxide nanoparticles on different mesoporous silicas prepared by an impregnation method. *Micropor. Mesopor. Mat.* 112, 327-337 (2008), each incorporated herein by reference in their entirety. However, low surface areas and pore volumes are typically obtained. General challenges with quick crystallization, accompanied with structural collapse during the mesostructure formations, along with the nature of the pore structures within the micellar silica template chosen are considerable issues. Other difficulties lie in the removal of the silica template, where the replicated mesostructure is seldom maintained because the inorganic precursors are inclined to be absorbed on the external surface of templates or the channels are not completely filled, causing the framework formed inside the pores to be lacking in sufficient internal cross-linkages. See Shon et al. (2008); and Yang, H. et al. One-Step Nanocasting Synthesis of Highly Ordered Single Crystalline Indium Oxide Nanowire Arrays from Mesostructured Frameworks. *J. Am. Chem. Soc.* 125, 4724-4725 (2003), each incorporated herein by reference in their entirety.

In view of the above, one objective of the present invention is the preparation of iron oxide mesoporous magnetic microparticles (IO-MMMs) with high surface areas and large internal pore volumes based on a modified reverse hard-templating approach using a mesoporous silica as the host. In particular, acid-prepared mesoporous spheres (APMS) are employed as the hard silica templates. Because of the excellent properties of the APMS template resulting from its rigid framework, 3D interconnected pores, as well as its high chemical and thermal stability, good control over key physiochemical properties of the replicated material is achieved. The as-prepared IO-MMMs exhibit generally spherical shapes, uniform size distributions, high surface areas, and large pore volumes, allowing them to be utilized as efficient multi-drug delivery vehicles. In order to achieve maximal anticancer effects, co-loading high amounts of one or more therapeutic drugs is a necessity to attain simultaneous drug delivery with efficient dosing.

BRIEF SUMMARY OF THE INVENTION

According to a first aspect, the present disclosure relates to a microparticle drug carrier, incorporating iron oxide nanoparticles having an average diameter in a range of 2-10 nm, where the microparticle drug carrier has an average diameter in a range of 0.5-1.2 μm and does not contain Si.

In one embodiment, the microparticle drug carrier has a BET surface area in a range of 50-300 $m^2/g$.

In one embodiment, the microparticle drug carrier is mesoporous with interconnected pores.

In a further embodiment, the microparticle drug carrier has an average pore diameter in a range of 2-10 nm.

In a further embodiment, the microparticle drug carrier has a pore volume in a range of 0.15-0.65 $cm^3/g$.

In one embodiment, the iron oxide nanoparticles comprise iron oxide (magnetite or maghemite).

In one embodiment, the microparticle drug carrier further comprises 50-250 μg of a pharmaceutical compound per mg microparticle drug carrier.

In a further embodiment, an amount of the pharmaceutical compound released is 4-10 times greater when the microparticle drug carrier is in contact with a slightly acidic medium having a pH in a range of 3.5-5.5 (~4.5) than a neutral physiological medium having a pH in a range of 6.4-8.4 (~7.4).

In a further embodiment, the microparticle drug carrier with the pharmaceutical compound has a hydrodynamic diameter in a range of 500-1200 nm.

In one embodiment, a plurality of the microparticle drug carrier in water, has a polydispersity index in a range of 0.4-0.6.

According to a second aspect, the present disclosure relates to a method for making the microparticle drug carrier of claim 1. The method involves contacting a mesoporous silica microparticle with an aqueous solution of an $Fe^{3+}$ salt and a reducing agent to produce an iron loaded silica particle. The iron loaded silica particle is dried and heated at 300-400° C. under an inert atmosphere to produce an iron oxide impregnated silica particle having an iron oxide within its pores. The iron oxide impregnated silica particle is reacted with a base to remove the silica, thus producing the microparticle drug carrier.

In one embodiment, the iron oxide impregnated silica particle has a Fe to Si atomic ratio of 0.5:1, corresponding to almost equal weight percentages of Fe to Si.

In one embodiment, the mesoporous silica microparticle has an average diameter in a range of 0.5-2 µm.

In one embodiment, the aqueous solution comprises 0.1-1.0 M $Fe^{3+}$.

In one embodiment the method further comprises, before the heating, repeating the contacting with the aqueous solution and the drying. The impregnation process is repeated with the $Fe^{3+}$ aqueous solution to ensure complete and maximal iron impregnation. According to a third aspect, the present invention relates to a method for treating a tumor with an anticancer drug. The method involves loading the anticancer drug into the microparticle drug carrier to produce a loaded carrier comprising 1-50 wt % anticancer drug, relative to a total weight of the loaded carrier (between 80-95% of the anticancer drug can be uploaded per mg of the microparticles), and contacting a tumor with the loaded carrier. Cancerous cells of the tumor uptake the loaded carrier, and the loaded carrier releases the drug within the cancerous cells.

In one embodiment, the anticancer drug is doxorubicin, daunorubicin, and/or tamoxifen.

In one embodiment, the tumor is a breast tumor or a colorectal tumor.

In one embodiment, a viability of the cancerous cells of the tumor after the contacting is 30-80% lower than a viability of noncancerous cells being contacted by a substantially similar loaded carrier.

In a further embodiment, the viability of the noncancerous cells after being contacted by the substantially similar loaded carrier is 2-10 times the viability of substantially similar noncancerous cells being contacted with a substantially similar amount of anticancer drug free in a solution.

In one embodiment, the uptake of the loaded carrier by the cancerous cells, relative to a total amount of the loaded carrier, is a factor of 2-10 times greater than an uptake of a similar concentration of loaded carrier brought into contact with a similar concentration of noncancerous cells under substantially similar conditions. The uptake increases with time with the most uptake observed after 24-48 hrs.

In one embodiment, during the uptake the loaded carrier interacts with a plasma membrane of a cancerous cell of a tumor and is internalized into the cytoplasm of the cancerous cell.

In one embodiment, where the anticancer drug is both daunorubicin and tamoxifen, a viability of the cancerous cells after the contacting is 5-50% of a viability of substantially similar cancerous cells being contacted with a single drug loaded carrier loaded with only one anticancer drug selected from the group consisting of doxorubicin, daunorubicin, and tamoxifen.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
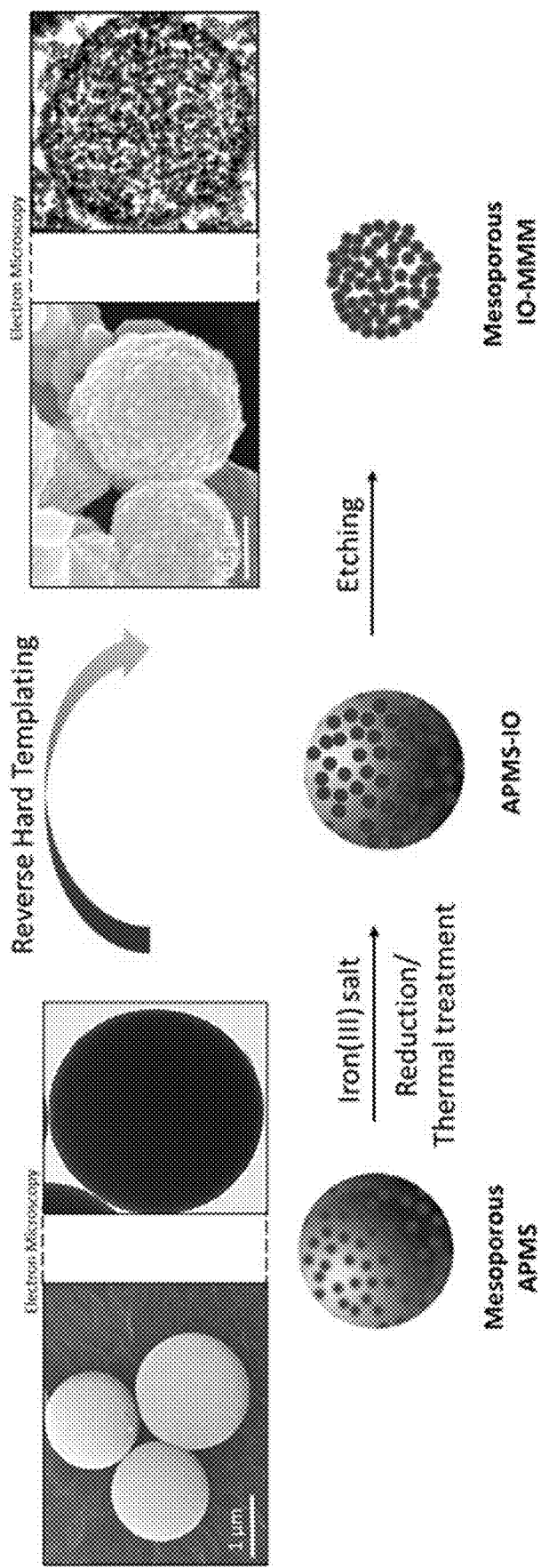
FIG. 1 shows a preparation of the microparticle drug carrier, or iron oxide mesoporous magnetic microparticle (IO-MMM).

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid, or gas, and whether in a crude mixture or isolated and purified.

As used herein, "composite" refers to a combination of two or more distinct constituent materials into one. The individual components, on an atomic level, remain separate and distinct within the finished structure. The materials may have different physical or chemical properties, that when combined, produce a material with characteristics different from the original components. In some embodiments, a composite may have at least two constituent materials that comprise the same empirical formula but are distinguished by different densities, crystal phases, or a lack of a crystal phase (i.e. an amorphous phase).

In the present disclosure, when comparing two numerical values, "percent difference" refers to the absolute difference between the two values, divided by the average of the two values, all multiplied by 100. Two values being "substantially similar" may have a percent difference of 10% or less, 5% or less, 2.5% or less, 1.0% or less, 0.50% or less, or 0.1% or less.

As used herein, the microparticle drug carrier may be referred as the "microparticle."

The present disclosure is intended to include all hydration states of a given compound or formula, unless otherwise noted or when heating a material. For example, $Ni(NO_3)_2$ includes anhydrous $Ni(NO_3)_2$, $Ni(NO_3)_2 \cdot 6H_2O$, and any other hydrated forms or mixtures. $CuCl_2$ includes both anhydrous $CuCl_2$ and $CuCl_2 \cdot 2H_2O$. Iron (III) chloride includes $FeCl_3 \cdot 6H_2O$, $FeCl_3$, anhydrous $FeCl_3$, and any other forms, mixtures, or hydration states.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of nitrogen include $^{14}N$ and $^{15}N$. Isotopes of oxygen include $^{16}O$, $^{17}O$, and $^{18}O$. Isotopes of nickel include $^{58}Ni$, $^{60}Ni$, $^{61}Ni$, $^{62}Ni$, and $^{64}Ni$. Isotopes of silicon include $^{28}Si$, $^{29}Si$, $^{30}Si$, $^{31}Si$, and $^{32}Si$. Isotopes of iron include $^{54}Fe$, $^{55}Fe$, 56Fe, $^{57}Fe$, $^{58}Fe$, $^{59}Fe$, and $^{60}Fe$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

According to a first aspect, the present disclosure relates to a microparticle drug carrier, comprising iron oxide nanoparticles. The iron oxide nanoparticles, as individual nanoparticles, have an average diameter in a range of 2-10 nm, 5-10 nm, 30-60 nm, 32-58 nm, 35-55 nm, 10-60 nm, 15-40 nm, or 20-35 nm. In one embodiment, the iron oxide nanoparticles consist of iron oxide, or in other embodiments, at least 99 wt %, at least 99.5 wt %, or at least 99.9 wt % of the iron oxide nanoparticles is Fe and O, relative to a total weight of the nanoparticles.

The iron oxide of the iron oxide nanoparticles may be an oxide of $Fe^{2+}$, $Fe^{3+}$, or a combination of $Fe^{2+}$ and $Fe^{3+}$. Oxides of $Fe^{2+}$ include FeO (iron(II) oxide, wüstite), $FeO_2$ (iron dioxide), and mixtures thereof. Mixed oxides of $Fe^{2+}$ and $Fe^{2+}$ include $Fe_3O_4$ (iron(II,III) oxide, magnetite), $Fe_4O_5$, $Fe_5O_6$, $Fe_5O_7$, $Fe_{25}O_{32}$, $Fe_{13}O_{19}$, and further mixtures thereof. Oxides of $Fe^{3+}$ include $Fe_2O_3$ (iron(III) oxide). $Fe_2O_3$ may be present as an amorphous phase or as at least one of the four crystalline phases: $\alpha$-$Fe_2O_3$ (hematite), $\beta$-$Fe_2O_3$, $\gamma$-$Fe_2O_3$ (maghemite), and $\varepsilon$-$Fe_2O_3$, or present as any mixture of amorphous and/or crystalline phases. In one embodiment, the iron oxide comprises hematite, magnetite, and/or maghemite. Preferably the iron oxide comprises $Fe_2O_3$ at a weight percentage of at least 75 wt %, preferably at least 80 wt %, more preferably at least 90 wt %, even more preferably at least 95 wt %, or at least 99 wt %, at least 99.5 wt %, at least 99.9 wt % relative to a total weight of the iron oxide.

In one embodiment, the agglomerated iron oxide nanoparticles comprise maghemite ($\gamma$-$Fe_2O_3$), and in a related embodiment, they consist of maghemite. Maghemite may be distinguished by X-ray diffraction (XRD) patterns, and a d-value of 2.96 Å corresponding to the spacing of the (220) crystal planes. In another embodiment, the iron oxide nanoparticles may comprise $Fe_2O_3$ of which at least 60 wt %, at least 75 wt %, preferably at least 85%, more preferably at least 90 wt %, or at least 95 wt %, or at least 99 wt %, or at least 99.5 wt %, or at least 99.9 wt % is maghemite relative to a total weight of the $Fe_2O_3$. In one embodiment, the agglomerated $Fe_2O_3$ nanoparticles may be considered superparamagnetic iron oxide nanoparticles (SPIONs), and thus the microparticle drug carrier may exhibit magnetic properties. Where the agglomerated $Fe_2O_3$ nanoparticles comprise less than 100 wt % $Fe_2O_3$, or less than 100 wt % maghemite, the nanoparticles may comprise amorphous $Fe_2O_3$ or any of the other three phases as previously mentioned. In an alternative embodiment, a different metal oxide may be used in addition to or in place of the iron oxide, including but not limited to $Co_3O_4$, NiO, $Cr_2O_3$, $In_2O_3$, $RuO_2$, and $CeO_2$.

In one embodiment, the iron oxide nanoparticles are clustered together to form microparticles that have an average diameter in a range of 500-1,200 nm, preferably 600-1,200 nm, more preferably 630-1,100 nm, even more preferably 650-1,000 nm, or 680-900 nm, or 700-850, or 720-820 nm, or about 750 nm. In one embodiment, each microparticle comprises an average of 900 to 12,000 agglomerated iron oxide nanoparticles, preferably 1,000 to 10,000 nanoparticles, preferably 2,000 to 9,000 nanoparticles, more preferably 3,000 to 8,000 nanoparticles. In one embodiment, each microparticle comprises an average of 100 to 2,000 nanoparticles, preferably 150 to 1,000 nanoparticles, more preferably 200 to 850 nanoparticles, or 250 to 800 nanoparticles. In one embodiment, a density of the nanoparticles may be greater in a volume adjacent to the exterior surface of the microparticle rather than a volume entirely within the microparticle. In other words, a porosity and pore volume may vary throughout the microparticle, where closer to the geometric center or centroid of the microparticle, the porosity and pore volume may be greater. In an alternative embodiment, the microparticles may be considered to be hollow. However, in a preferred embodiment, the density or packing of the agglomerated iron oxide nanoparticles does not vary significantly throughout the microparticle.

In one embodiment, the microparticle drug carrier has a BET surface area in a range of 50-300 $m^2/g$, 200-300 $m^2/g$, 210-290 $m^2/g$, 220-280 $m^2/g$, 225-270 $m^2/g$, 230-260 $m^2/g$, 235-250 $m^2/g$, or about 240 $m^2/g$. In one embodiment, the microparticle drug carrier is mesoporous. In one embodiment, the microparticle drug carrier is mesoporous with an average pore diameter in a range of 2-10 nm, 3.0-5.0 nm, preferably 3.2-4.8 nm, more preferably 3.4-4.6 nm, or about 4.0 nm. In one embodiment, the microparticle drug carrier has a pore volume in a range of 0.15-0.65 $cm^3/g$, 0.45-0.65 $cm^3/g$, preferably 0.47-0.63 $cm^3/g$, more preferably 0.50-0.60 $cm^3/g$, even more preferably 0.52-0.58 $cm^3/g$, or 0.53-0.57 $cm^3/g$, or 0.54-0.56 $cm^3/g$, or about 0.55 $cm^3/g$. In one embodiment, the pores are interconnected, meaning that they are in fluid communication with one another through the interior of the microparticle. Preferably for the average microparticle, at least 80 vol %, at least 85 vol %, at least 90 vol %, at least 95 vol % of the total pore volume is interconnected, or equivalently, a part of one continuous volume. In one embodiment, the microparticle has a porosity in a range of 25-75%, preferably 30-70%, more preferably 35-65%.

The Wadell sphericity of a rounded three-dimensional object is defined by the ratio of the surface area of a sphere (the sphere of a size chosen to have the same volume as the given particle) to the surface area of the object. The values of Wadell sphericity range from 0 to 1, where a value of 1 is a perfect sphere, and objects become less spherical as their sphericity approaches a value of 0. The Wadell sphericity may be approximated by $$\Psi \approx \left(\frac{bc}{a^2}\right)^{1/3},$$

where a, b, and c are the lengths of the long, intermediate, and short axes, respectively, of an individual object.

In one embodiment, the microparticles are round and substantially spherical, having an average Wadell sphericity value in a range of 0.85-1.00, more preferably 0.90-1.0. In another embodiment, the microparticles are round but may not be substantially spherical, but generally spherical or having some degree of oblong, ellipsoidal, and/or ovoidal character. Thus, the Wadell sphericity may be lower, for instance, in a range of 0.30-0.90, preferably 0.35-0.80, more preferably 0.40-0.75.

In one embodiment, the microparticles may be substantially spherical, meaning that for each microparticle, the distance from the microparticle centroid (center of mass) to anywhere on the microparticle outer surface varies by less than 30%, preferably by less than 20%, more preferably by less than 10% of the average distance.

In one embodiment, a cross-section of the microparticles may be generally circular with an average circularity in a range of at least 0.80, preferably at least 0.85, more preferably at least 0.87, or at least 0.90. As defined here, for a 2-dimensional region, the circularity is $4\pi \times [area] \times [perimeter]^{-2}$, where a circle has a circularity of 1.0. A cross-section of a sphere is a circle, and thus the cross-section of a sphere would have a circularity of 1.0.

In one embodiment, the agglomerated iron oxide nanoparticles have an average Wadell sphericity in a range of 0.20-0.90, preferably 0.25-0.60, more preferably 0.30-0.55. However, in some embodiments, the agglomerated iron oxide nanoparticles may be more spherical with an average Wadell sphericity of at least 0.85 or at least 0.90. In one embodiment, the microparticle drug carrier further comprises a pharmaceutical compound that may be confined within the pores of the microparticle and/or adsorbed onto an interior or less preferably to an exterior surface of the microparticle. In one embodiment, the pharmaceutical compound may be present in an amount of 50-250 μg per mg microparticle drug carrier, preferably 120-240 μg per mg microparticle, even more preferably 200-240 μg per mg microparticle.

In one embodiment, a plurality of the microparticle drug carriers in water is generally dispersed and not agglomerated, with or without the pharmaceutical compound. Here, the polydispersity index (PDI) may be in a range of 0.0-0.6, preferably 0.1-0.5, or 0.4-0.6. In one embodiment, microparticle drug carriers may be easily dispersed in water due to the presence of hydroxyl groups on the exterior surface of the microparticle.

In one embodiment, the pharmaceutical compound may be an active therapeutic agent. As used herein, the terms "therapeutic agent" include any synthetic or naturally occurring biologically active compound or composition of matter which, when administered to an organism (human or non-human animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; chemotherapy agent; cough and cold preparations; decongestants; diagnostics; hormones; bone growth stimulants and bone resorption inhibitors; immunosuppressives; muscle relaxants; antitumor agents; psychostimulants; anticancer agents; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Preferably the therapeutic agent has a width or diameter smaller than 5 nm so that it may adsorb within a pore of the microparticle drug carrier. Typically, anticancer drugs are less than 5 nm, for instance plenty of anticancer drugs with suitable molecular sizes such as Dox have a molecular size estimated to be ~1.37 nm. However, large molecule drugs such as biologics may be successfully used with the microparticle drug carrier.

In one embodiment, the pharmaceutical compound is an anticancer drug such as a hormonal therapeutic anticancer drug and/or a chemotherapeutic anticancer drug. In one embodiment, the pharmaceutical compound is an anticancer drug, including but not limited to doxorubicin, daunorubicin, tamoxifen, nab-paclitaxel, carboplatin, cyclophosphamide, epirubicin, fluorouracil, gemcitabine, eribulin, ixabepilone, methotrexate, mutamycin, mitoxantrone, vinorelbine, paclitaxel, docetaxel, thiotepa, vincristine, cepecitabine, raloxifen, toremifene, anastrozole, exemestane, letrozole, fulvestrant, and combinations thereof. In a preferred embodiment, the pharmaceutical compound is an anticancer drug comprising doxorubicin, daunorubicin, and/or tamoxifen.

In one embodiment, the microparticle drug carrier may be loaded with a pharmaceutical compound by mixing the microparticle drug carrier in a solution of the pharmaceutical compound to be adsorbed. Here, in this embodiment, a mass ratio of the pharmaceutical compound to the microparticle may be in a range of 0.10-2.00, preferably 0.15-1.00, more preferably 0.20-0.75, even more preferably 0.22-0.50. In one embodiment, the microparticle may be present in the solution at a concentration in a range of 0.1-5.0 mg/mL, preferably 0.2-2.0 mg/mL, more preferably 0.5-1.5 mg/mL, or about 1.0 mg/mL. The microparticle and the pharmaceutical compound may be mixed for a time in a range of 18-48 h, preferably 24-48 h, or 30-42 h. The loaded microparticle may be rinsed and washed several times to prevent a sudden release of weakly-bound pharmaceutical compound when the loaded microparticle is used for therapy. In one embodiment, the microparticle may be loaded with other compounds such as a fluorescent dye, for tracking within cells or organisms. A fluorescent dye may be loaded with a pharmaceutical compound, or microparticles loaded with a pharmaceutical compound only may be mixed with microparticles loaded with fluorescent dyes only. The fluorescent dye may be FITC, Texas Red®, NBD, DAPI, or some other fluorescent dye, and may be present at concentrations similar to those described for the pharmaceutical compound. In another embodiment, an exterior surface of the microparticle drug carrier may be chemically functionalized with a fluorescent dye. In another embodiment, the magnetic nature of the microparticle may be used for tracking within organisms.

In one embodiment, the microparticle drug carrier loaded with a pharmaceutical compound may release the pharmaceutical compound, for instance, by desorption or diffusion. In one embodiment, the rate of release may be pH dependent. For instance, the rate of release may be greater at a lower pH range than a higher pH range.

In a preferred embodiment, the rate of release is greater at a lower pH range. In one embodiment, an amount of the pharmaceutical compound released is 4-8 times greater, preferably 5-7 times greater when a loaded microparticle drug carrier is in contact with a slightly acidic medium having a pH in a range of 3.5-5.5, preferably 4.0-5.0 than compared with a medium having a pH in a range of 6.4-8.4, preferably 7.0-7.6, more preferably about 7.4 or about a physiological pH. Here, the amount of pharmaceutical compound released may be compared over a time period in a range of 0.5-100 h, 0.5-50 h, more preferably 0.5-48 h. In one embodiment, 35-95%, preferably 40-90%, more preferably 45-85% of the total pharmaceutical compound adsorbed on and within the microparticle drug carrier is released in a time period of 30-60 h, preferably 40-55 h, more preferably 45-50 h.

In one embodiment, the microparticle drug carrier does not have a pharmaceutical compound or drug and consists of iron oxide, or consists essentially of iron oxide. However, in another embodiment, the microparticle drug carrier, as a loaded drug carrier, consists of iron oxide and the pharmaceutical compound to be delivered. In another embodiment, the microparticle drug carrier does not contain Si, or the microparticle drug carrier comprises less than 1 wt %, less than 0.5 wt %, preferably less than 0.1 wt %, more preferably less than 0.05 wt %, even more preferably less than 0.01 wt % Si relative to a total weight of the microparticle drug carrier. In another embodiment, the microparticle drug carrier does not contain silica, or the microparticle drug carrier comprises less than 1 wt %, less than 0.5 wt %, preferably less than 0.1 wt %, more preferably less than 0.05 wt %, even more preferably less than 0.01 wt % silica relative to a total weight of the microparticle drug carrier. While the microparticle may not comprise Si or silica, it is possible in some embodiments that it may be loaded with a drug or pharmaceutical compound that contains Si or silica.

In another embodiment, the microparticle drug carrier does not contain gold, or the microparticle drug carrier comprises less than 1 wt %, less than 0.5 wt %, preferably less than 0.1 wt %, more preferably less than 0.05 wt %, even more preferably less than 0.01 wt % gold relative to a total weight of the microparticle drug carrier. In another embodiment, the microparticle drug carrier does not contain hydroxyapatite, or the microparticle drug carrier comprises less than 1 wt %, less than 0.5 wt %, preferably less than 0.1 wt %, more preferably less than 0.05 wt %, even more preferably less than 0.01 wt % hydroxyapatite relative to a total weight of the microparticle drug carrier. In another embodiment, the microparticle drug carrier does not contain lipids or a lipid layer (monolayer or bilayer) or is not partially or fully enclosed by a lipid layer. In another embodiment, the microparticle drug carrier is not partially or fully enclosed by a lipid layer that is not a cell membrane. In another embodiment, the microparticle drug carrier comprises less than 1 wt %, less than 0.5 wt %, preferably less than 0.1 wt %, more preferably less than 0.05 wt %, even more preferably less than 0.01 wt % lipids relative to a total weight of the microparticle drug carrier. As used here, the phrasing "does not contain" is considered equivalent to "is not in contact with." In one embodiment, the microparticle drug carrier is not coated or does not have a coating on its exterior surface. In alternative embodiments, the microparticle drug carrier may be encapsulated within a micelle or a lipid vesicle. In another embodiment, the microparticle drug carrier does not contain a ceramic material. In alternative embodiments, the microparticle drug carrier may not be used for therapeutic compounds but for different applications. For instance, the microparticle may be loaded with fertilizer and applied to plants. Alternatively, the microparticle may be loaded with dyes, flavor molecules, or scents.

According to a second aspect, the present invention relates to a method for treating a tumor with an anticancer drug. The method involves loading the anticancer drug into the microparticle drug carrier to produce a loaded carrier comprising 1-50 wt %, preferably 5-40 wt %, more preferably 10-30 wt %, even more preferably 12-25 wt % anticancer drug, relative to a total weight of the loaded carrier, and contacting a tumor with the loaded carrier. The cancerous cells of the tumor uptake the loaded carrier, and the loaded carrier releases the drug within the cancerous cells due to the acidic microenvironment of the tumor.

Here, the method of loading and the type of anticancer drug may be those discussed previously. In one embodiment, the tumor is of a breast cancer or a colorectal cancer. However, in other embodiments, the tumor may be of a liver cancer, stomach cancer, skin cancer, prostate cancer, ovarian cancer, testicular cancer, renal cancer, brain cancer, lung cancer, uterine cancer, colon cancer, bladder cancer, esophageal cancer, and pancreatic cancer. The cancer may be an adenocarcinoma, a basal cell carcinoma, a squamous cell carcinoma, a renal cell carcinoma, a ductal carcinoma in situ (DCIS), an invasive ductal carcinoma, a transitional cell carcinoma, a soft tissue sarcoma, or leukemia. Preferably the cancer is an adenocarcinoma. In other embodiments, the microparticle drug carrier is brought into contact with cancer cells that may not necessarily be part of a tumor. Preferably the tumor or cancer cells are of a mammal. The mammal may be *Homo sapiens sapiens, Pan troglodytes, Bos primigenius, Sus scrofa domesticus, Canis lupus familiaris, Felis catus, Rattus norvegicus, Mus musculus*, or *Equus ferus caballus*. Preferably, the mammal may be *Homo sapiens sapiens*. In an alternative embodiment, the cancer may be in a non-mammal animal, such as a *Gallus gallus*.

A mammal in need of treatment includes a subject already with a cancer, a mammal which does not yet experience or exhibit symptoms of a cancer, and a mammal predisposed to a cancer. In one embodiment, the subject is a person who is predisposed to cancer, e.g. a person with a family history of cancer. Other examples include a person with: (i) a personal history of colorectal polyps and/or inflammatory bowel disease, (ii) a family history of adenomatous polyps, (iii) an inherited syndrome (Lynch syndrome, Turcot syndrome, Peutz-Jeghers syndrome, MUTYH-associated polyposis), and/or (iv) type 2 diabetes, are at a higher risk of contracting colon cancer. Women or a person with (i) certain inherited genes (e.g. mutated BRCA1, BRCA2, ATM, TP53, CHEK2, PTEN, CDH1, STK11, and PALB2), (ii) radiation to one's chest, and/or (iii) exposure to diethylstilbestrol (DES), are at a higher risk of contracting breast cancer. A person with (i) chronic viral hepatitis (Hep-B or Hep-C), (ii) cirrhosis, (iii) type 2 diabetes, (iv) diseases such as tyrosinemia, alphal-antitrypsin deficiency, *porphyria cutanea tarda*, glycogen storage diseases, wilson disease, and/or (v) chronic exposure to aflatoxins, vinyl chloride, and thorium dioxide (Thorotrast), are at a higher risk of contracting cancer. In a preferred embodiment, the mammal in need of treatment may be currently undergoing other forms of treatment for a cancer, for instance, chemotherapy or radiation therapy. In another embodiment, the mammal in need of treatment may be one that has had cancer and is being treated in order to prevent relapse.

In another embodiment, cancer cells may be treated in vitro, for instance, as a way to test the loaded carrier under different conditions in a controlled environment or with additional drugs. These cancer cells may come from a biopsy of a mammal, for instance a biopsy of a colorectal cancer or a breast cancer, or the cells may be from an established cancer cell line, for instance, MDA-MB-231, MCF-7, AU565, BT20, HeLa, HepG2, SNU-475, LH86, Caco-2, NCI-H250, A-498, Eph41424.2, SK-MES-1, DU 145, CHLA-02-ATRT, SCC-4, A-253, HCT-8, HCA-46, HCA-7, MDST8, LS174T, or some other cancer cell line. Preferably the cancer cell line may be MCF-7, HCT-8, and/or KAIMRC-1. The cells may come from a cancer that formed on its own in a mammal, or may come from a cancer that was formed by chemical induction or radiation. Diethyl nitrosoamine, (DEN), 7,12-dimethylbenz[a]anthracene (DMBA), 12-O-tetradecanoylphorbol-13-acetate (TPA), azoxymethane (AOM), or some other carcinogenic compound may be used to chemically induce cancer. Additionally, the cancer cells may be derived from a tumor or cancer cells that were transplanted and allowed to grow in a mammal.

In one embodiment, where the tumor to be treated is within a mammal, the method of contacting involves a step of administering the loaded carrier to the mammal. In one embodiment of the method, the administering is by a mode of oral administration, intravenous administration, topical administration, inhalation spray, rectal administration, topical administration, intradermal administration, transdermal administration, subcutaneous administration, intramuscular administration, intralesional administration, intrapulmonal administration, sublingual administration, or intratumoral administration. Preferably the administering is by intravenous administration, intramuscular administration, or intratumoral administration.

Preferably, an amount of the loaded carrier is administered in order that a therapeutically effective amount of the anticancer drug or some other pharmaceutical compound is released from the loaded carrier to the tumor, including inside the cancer cells of the tumor. Here, a "therapeutically effective amount" of the anticancer drug, with respect to a method of treatment, refers to an amount of the anticancer drug released from the loaded carrier which, when administered as part of a desired dosage regimen, alleviates a symptom, ameliorates a condition, or slows the onset of disease conditions according to clinically acceptable standards for the disorder or condition to be treated, e.g., at a reasonable benefit/risk ratio applicable to any medical treatment.

In one embodiment of the method, the therapeutically effective amount is 0.1 mg-5 g, preferably 0.2 mg-3 g, more preferably 0.3-2 mg of the anticancer drug per kg of the mammal per day. In other embodiments, lower dosages may be effective, such as 0.1-100 µg, preferably 10-50 µg per kg of the mammal per day. In one embodiment, the administration may be split or distributed over a single day. For example, a 1 mg per kg per day dose could be split into two separate doses of 0.5 mg per kg, and administered at two different times in a day, for example, 8 AM and 7 PM. Or, a 1 mg per kg per day dose could be split into four separate doses of 0.25 mg per kg, and administered at four different times in a day. In a related embodiment, a daily dose may be a combined dose administered less frequently than every day. For example, a 0.75 g per kg per day dose could be administered as a 1.5 g per kg dose every other day. In certain embodiments, the dose may be continually administered throughout an entire day or a part of a day, such as by transdermal administration or intravenous administration.

In one embodiment, when the loaded carrier is brought into contact with the tumor, the cancerous cells of the tumor uptake the loaded carrier inside the cell (e.g. by endocytosis). In one embodiment, the uptake of the loaded carrier by the cancerous cells, relative to a total amount of the loaded carrier, is a factor of 2-10, preferably 2.5-9.0, more preferably 2.8-8.0, even more preferably 3.2-7.0, 3.5-6.5, or 4-7 times greater than an uptake of a similar concentration of loaded carrier brought into contact with a similar concentration of noncancerous cells under substantially similar conditions. Preferably the cancerous and non-cancerous cells are of the same type (e.g. epithelial cells) and of the same tissue (e.g. breast tissue). In one embodiment, the difference in uptake becomes apparent when the cells are in contact with the loaded carrier for a time period in a range of 2-60 h, preferably 4-55 h, more preferably 6-48 h.

In one embodiment, during the uptake the loaded carrier interacts with a plasma membrane of a cancerous cell of a tumor and is internalized into the cytoplasm of the cancerous cell. In one embodiment, the cell membrane wraps around the microparticle drug carrier. In one embodiment, the microparticle drug carriers interact or attach to the plasma membrane and/or microvilli. In one embodiment, the microparticle drug carrier is internalized and localized to the cytoplasm of the cancerous cell but not the nucleus. However, in some embodiments, the aggregates or clusters of the microparticle drug carrier may form near the nucleus, suggesting trafficking within acidic lysosomal compartments. In one embodiment, the cancerous cells uptake the microparticle drug carriers through an endocytic mechanism. The cell membrane may engulf the microparticle drug carrier. In one embodiment, the phospholipid head groups of the plasma membrane may adsorb to surface hydroxyl groups on the microparticle drug carrier. The microparticle drug carrier may be contained intracellularly within a vesicle which is then trafficked by an endolysosomal pathway. In one embodiment, the microparticle drug carrier is taken up via nonspecific energy-dependent membrane-tangled internalization and micropinocytosis. In one embodiment, the microparticle drug carrier is unable to passively diffuse into cells or into organelles within the cells. In one embodiment, anticancer drugs are released from a loaded carrier due to biochemical changes inside cells or the tumor microenvironment, for instance as a result of acidic pH and/or lysosomal hydrolytic enzymes. Released drugs may then diffuse and traffic to the nucleus.

Figure 10A:
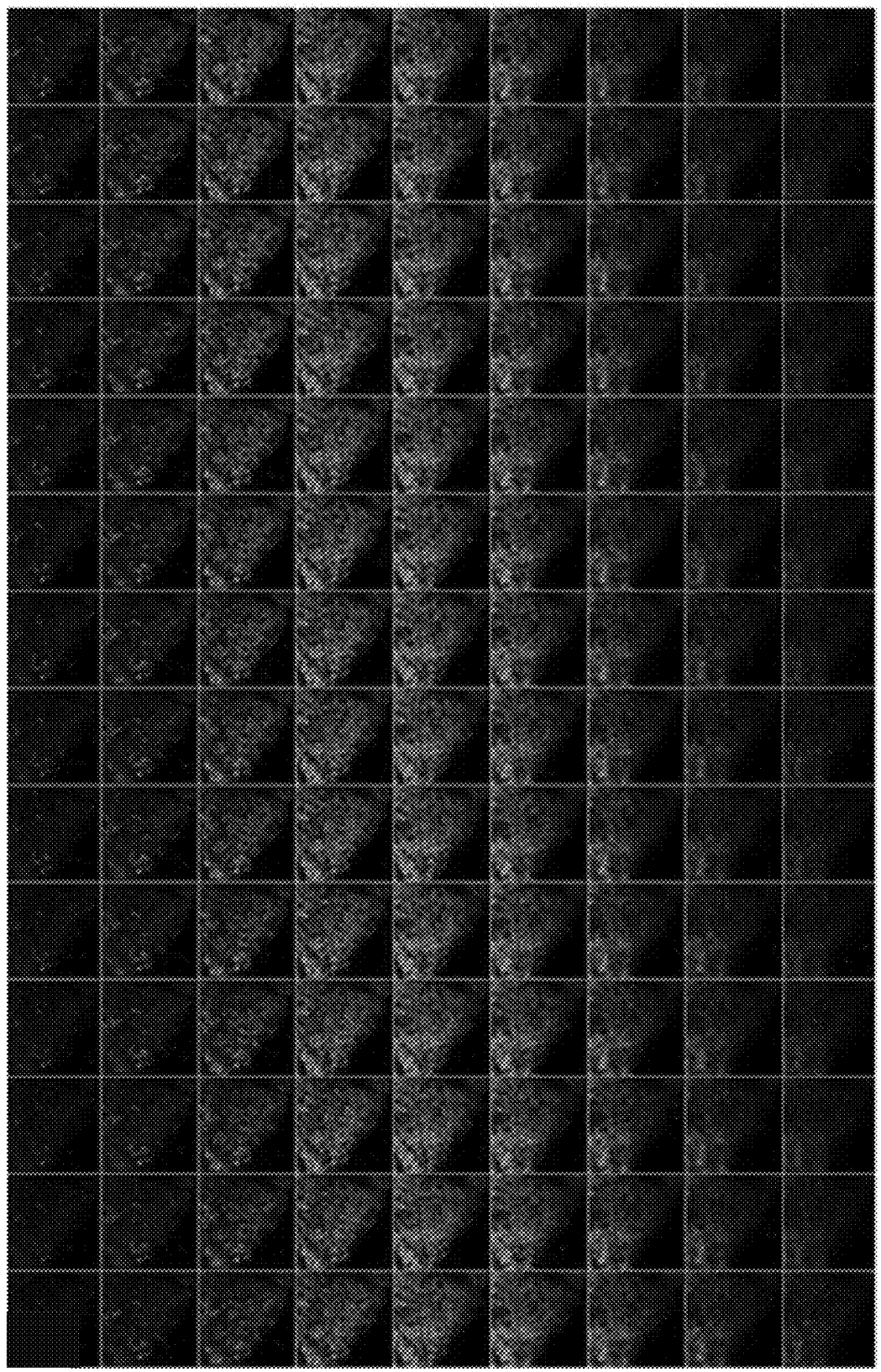
FIG. 10A is a gallery view of z-stack images of a patient breast cancer tumor tissue treated with Daun/Tam@IO-MMMs for 2 weeks at 37° C. and 5% $CO_2$.
Figure 10B:
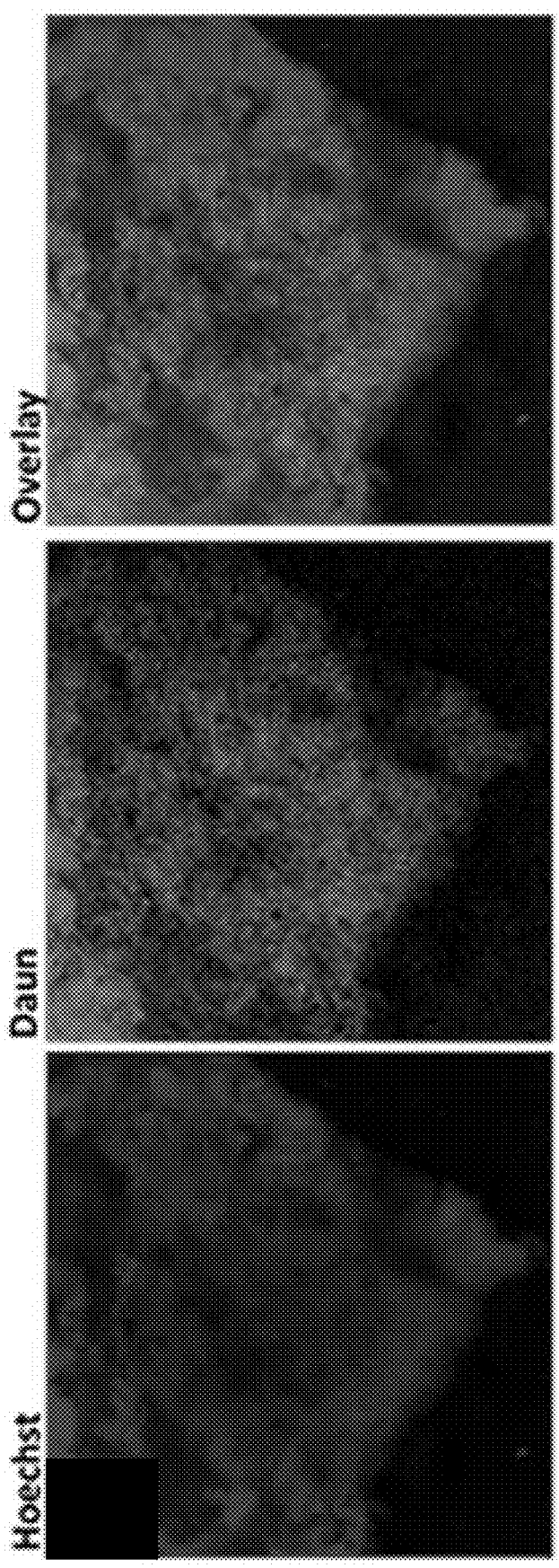
FIG. 10B shows a representative middle slice image of the z-stack of FIG. 10A.
Figure 10C:
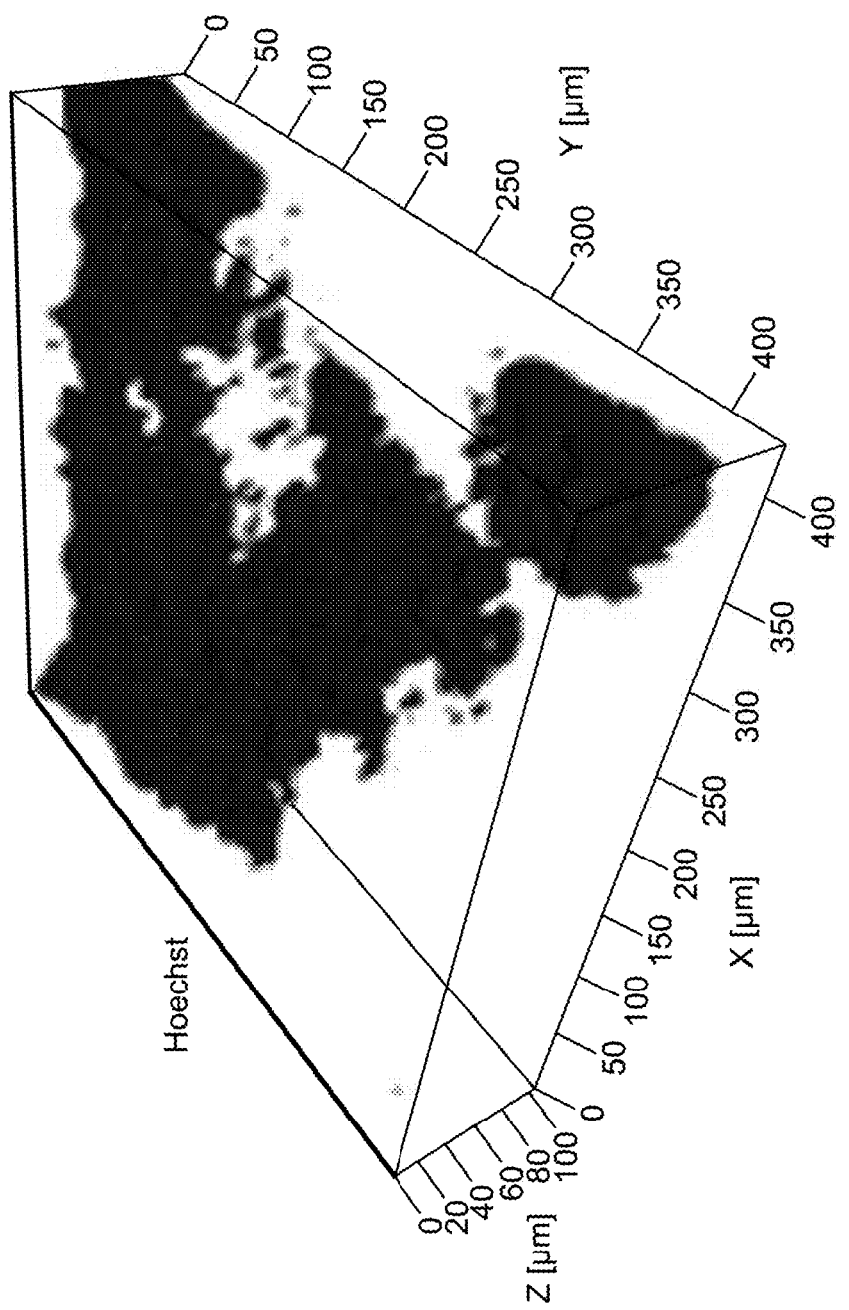
FIG. 10C is a 3D reconstruction of z-stack images from FIG. 10A.
Figure 10C:
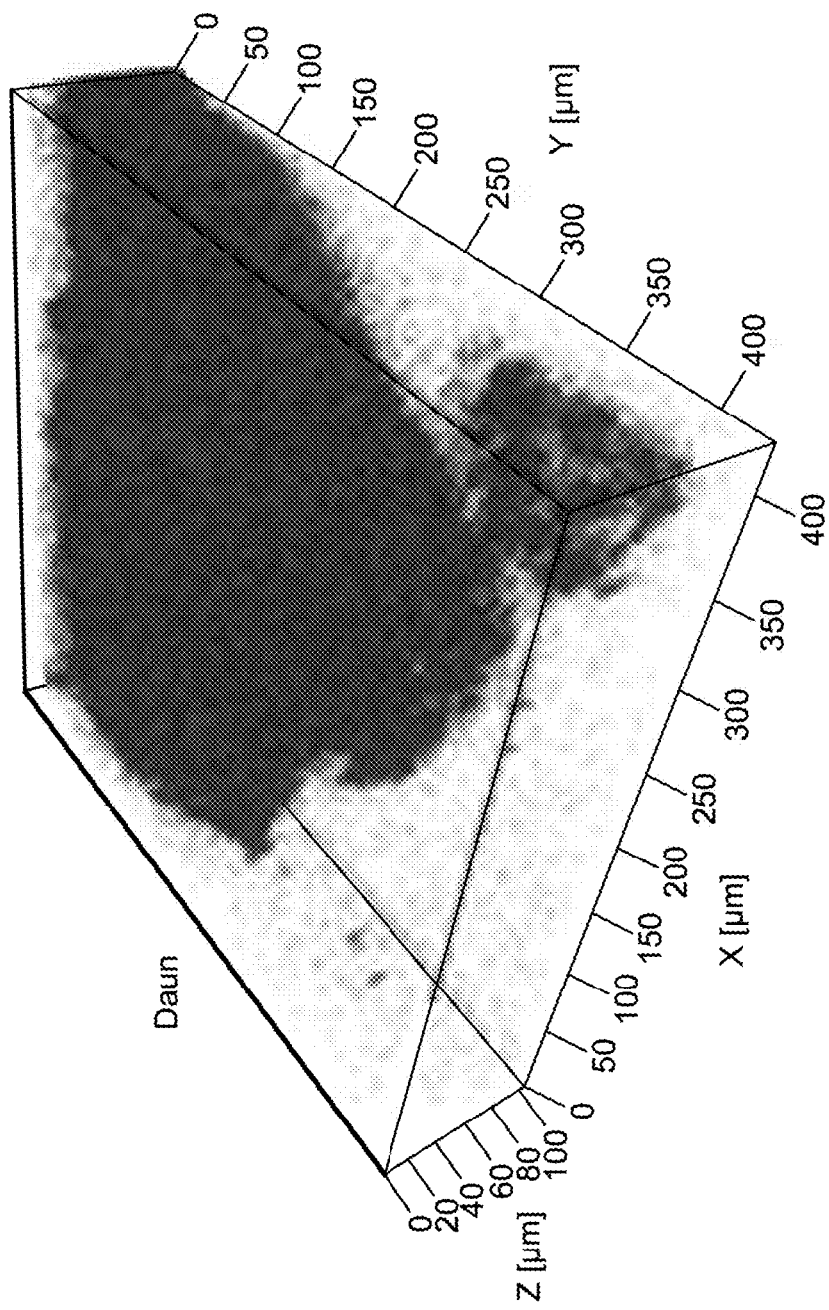
Figure 10C:
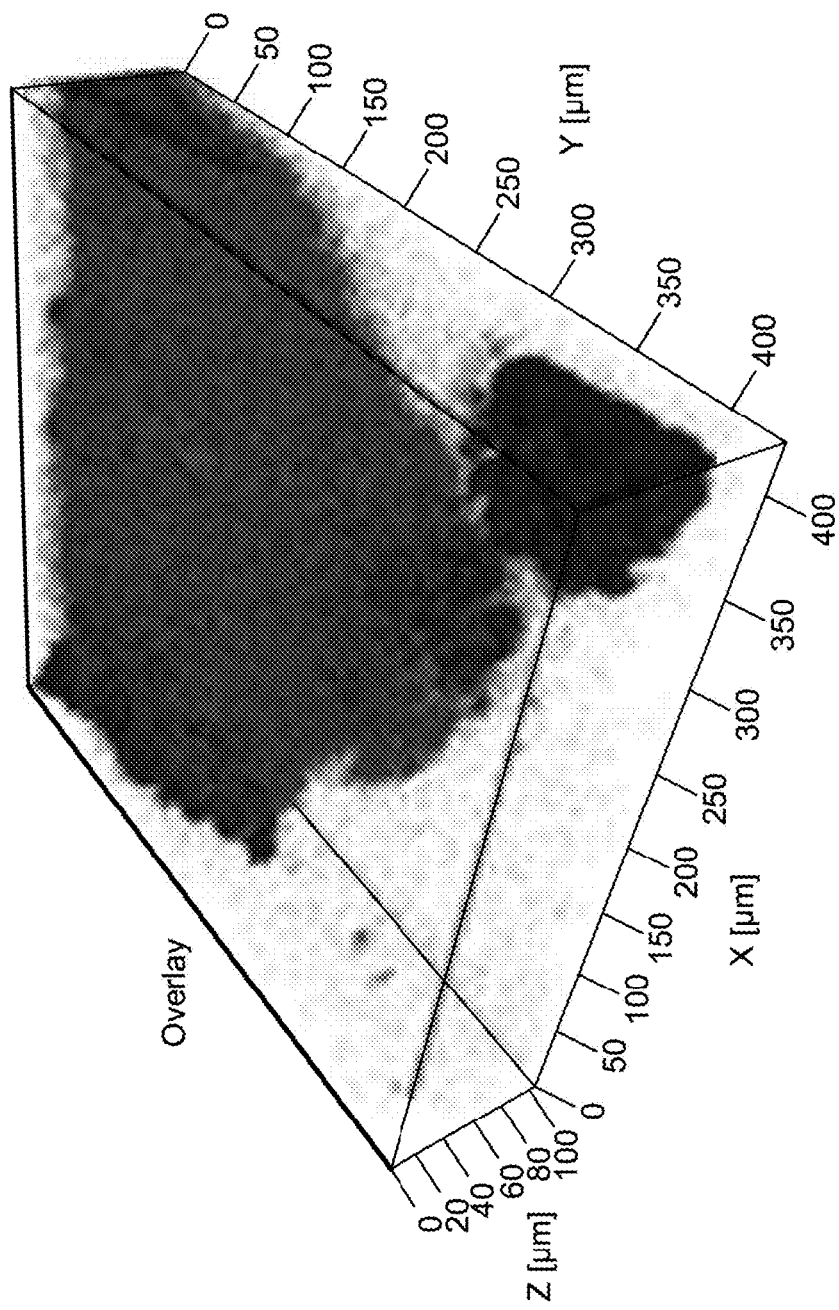

Generally, the means of uptake and internalization of the microparticle drug carrier may be observed by SEM and TEM (FIGS. 8A-8G, 9A-9E), and the extent of the internalization may also be observed by confocal fluorescence microscopy imaging (FIGS. 10A-10C).

In one embodiment, the uptake ability shown here of the microparticle drug carrier indicates that the microparticle drug carrier can access unusually leaky solid tumors, significantly improving the limited tumor penetration drug capabilities known to drugs free in solution. Due to the enhanced permeation and retention (EPR) effect, the loaded drug carriers accumulate and retain in the tumor vicinity or within the tumor, releasing the loaded drugs. Moreover, since the loaded drug carriers have average sizes between 500-1200 nm, considerably larger than nanoparticles of 200 nm or less, they are unlikely to penetrate the blood-brain barrier.

Preferably, following the uptake of the loaded carrier, the loaded carrier releases more of the anticancer drug within the acidic lysosomal environment of the cell than outside the cell. In some embodiments, cancer cells may have cytoplasms with a lower average pH than non-cancerous cells, and where the drug release of the loaded carrier is pH dependent, the loaded carrier may release more of the drug in the cancer cell than if it was uptaken by a non-cancerous cell. In other embodiments, this might be due to the increased uptake of the loaded carrier by cancerous cells compared to non-cancerous cells, attributed to differences in cell-membrane compositions, characteristics, morphologies, immunoprofiles, and metabolic activities between the cancerous and non-cancerous cells. The high metabolic activity of tumor cells along with the low metabolic activity of non-cancerous cells can particularly contribute to the observed increase in uptake and subsequent drug release.

In one embodiment, the loaded carrier may be uptaken by multiple cells deep within a tumor. For instance, a tumor incubated with the loaded carrier for a time in a period of 7-21 days, preferably 10-18 days, more preferably 12-16 days, or about 14 days may have microparticles of loaded carrier transported by the cancer cells to a depth in a range of 50-300 μm, preferably 75-250 μm, more preferably 80-200 μm, even more preferably 90-120 μm within the tumor.

In one embodiment, a viability of the cancerous cells of the tumor after the contacting is 40-80% lower, preferably 45-75% lower, more preferably 50-70%, more preferably 30-80% lower than a viability of the noncancerous cells being contacted by a substantially similar loaded carrier. Here, the viability may be measured 24-60 h, preferably 36-48 h after the contacting or administering. In the case of in vitro testing, the cell viability may be measured by MTT assay or some other assay.

Figure 6A:
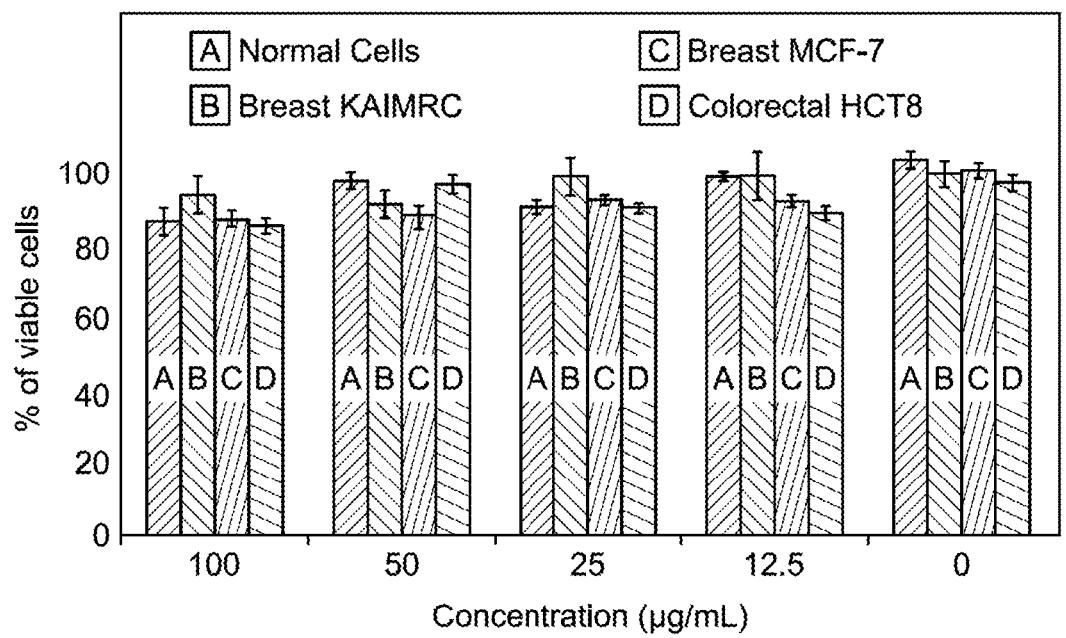
FIG. 6A shows MTT cell viability assay results for different concentrations of drug-free IO-MMMs being contacted with different types of cancerous and primary normal cells.
Figure 6B:
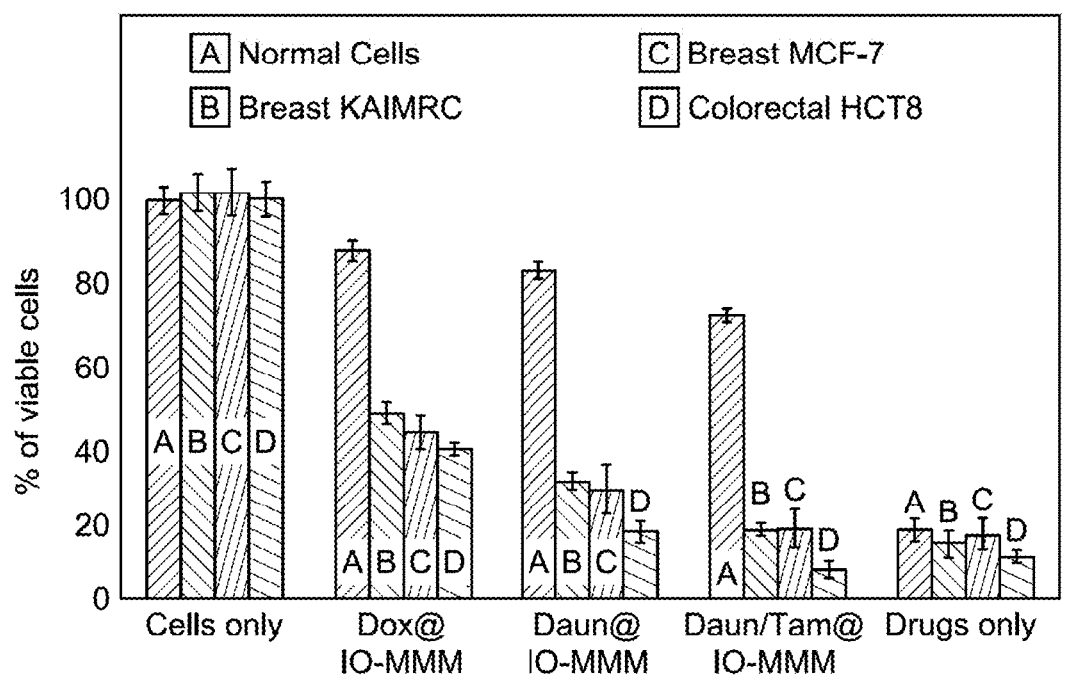
FIG. 6B shows MTT cell viability assay results for drug loaded IO-MMMs being contacted with different types of cancerous and primary normal cells.

In a further embodiment, the viability of the noncancerous cells after being contacted by the substantially similar loaded carrier is 2-10, 3-9, or 4-8 times the viability of substantially similar noncancerous cells being contacted with a substantially similar amount of anticancer drug free in a solution. Here, the substantially similar amount of anticancer drug free in solution means that the cells are treated with the same concentration of the drug as if it has been completely released from the microparticle drug carrier. In a related embodiment, the substantially similar amount means that the concentration of anticancer drug free in solution is similar to the concentration used in the solution for microparticle carrier drug loading. Here, the contacting times, temperatures, and other common parameters of cell culture are all similar. The anticancer drug being free in solution means that the drug molecules are not attached, tethered, or adsorbed to a solid support and are able to freely diffuse in solution. An example of this embodiment is shown in FIG. 6B, where the cell viability is similar for the free drug in solution, indicating similar cytotoxicities against both cancerous and non-cancerous cells. However, where the anticancer drug is loaded into the microparticle drug carrier, the noncancerous cells have a higher viability than the cancerous cells.

Compared to free drugs, the microparticle drug carrier displays enhanced drug accumulation inside tumor tissues and selective drug delivery in cancer cells (see confocal images of FIGS. 7A-7C and 10A-10C). While the potency of the drug loaded carrier towards the different cancerous cell lines was comparable to the potency of free drugs, it significantly decreased against the noncancerous cells. Importantly, the free anticancer drugs, at equivalent concentrations, were found to be toxic to all the tested cells killing the cancerous and noncancerous cells concurrently. This observed enhanced cytotoxicities of the drug loaded carrier compared to free drugs towards cancerous cells, with the least sensitivity towards the normal cells, shows potential for the microparticle drug carrier as an efficient and selective drug delivery vehicle. Thus, the microparticle drug carrier described here is superiorly advantageous, as it reduces the unwanted diffusive side effects of the free drugs and limited tissue penetration allowing selective synergistic anticancer drug delivery.

In one embodiment, the anticancer drug is both daunorubicin and tamoxifen, and a viability of the cancerous cells after the contacting is 5-50%, 5-80%, 10-70%, preferably 20-65%, 30-60% of a viability of substantially similar cancerous cells being contacted with a single drug loaded carrier. Here, the single drug loaded carrier is loaded with only doxorubicin, daunorubicin, or tamoxifen. An example of this embodiment is shown in FIG. 6B, where the cancerous cells treated with the Daun/Tam loaded carrier have a lower viability than the cancerous cells treated with the Daun loaded carrier. In one embodiment, this may be considered a synergistic effect. In one embodiment, a total mass of the daunorubicin and the tamoxifen loaded in the drug carrier is similar to the mass of the single drug loaded in the single drug loaded carrier. In another embodiment, the single drug loaded carrier is loaded with only daunorubicin or tamoxifen, and the mass of that drug is similar to the mass of daunorubicin or tamoxifen loaded in the drug carrier. In another embodiment, the synergistic effect may involve other anticancer drugs as previously described. It is envisioned that this synergistic effect allows lower doses of drugs for an equivalent therapeutic effect of free drugs, thus reducing the toxicity to normal, noncancerous cells.

According to a third aspect, the present disclosure relates to a method for making the microparticle drug carrier of the first aspect. The method involves contacting a mesoporous silica microparticle with an aqueous solution of a $Fe^{3+}$ salt and a reducing agent to produce an iron loaded silica particle. The iron loaded silica particle is dried and heated at 300-400° C. under an inert atmosphere to produce an iron oxide impregnated silica particle having an iron oxide within its pores. The iron oxide impregnated silica particle is reacted with a base to remove the silica template, thus producing the microparticle drug carrier.

In one embodiment, the mesoporous silica microparticle has an average diameter in a range of 1.0-2.0 μm, preferably 1.2-1.8 μm, more preferably 1.3-1.7 μm, or about 1.5 μm. The mesoporous silica particle may be substantially spherical, with a Wadell sphericity value of at least 0.90, or at least 0.95. The mesoporous silica microparticle may have a BET surface area in a range of 400-800 $m^2/g$, preferably 450-750 $m^2/g$, more preferably 500-700 $m^2/g$, even more preferably 575-675 $m^2/g$, 600-650 $m^2/g$, or about 625 $m^2/g$. In one embodiment, the mesoporous silica microparticle may have a pore volume in a range of 0.75-1.00 $cm^3/g$, preferably 0.80-0.90 $cm^3/g$, or 0.82-0.88 $cm^3/g$. In one embodiment, the mesoporous silica particle has an average pore diameter in a range of 2-10 nm, preferably 3.5-7.5 nm, more preferably 4.0-6.0 nm, or about 5 nm.

In one embodiment, the mesoporous silica particle is similar to three-dimensional (3D) and/or two-dimensional (2D) mesoporous silica (i.e. KIT-6, SBA-15, MSU-H, MCM-41, TUD-1, HMM-33, FSM-16, etc.). In one embodiment, the mesoporous silica particle comprises amorphous silica. In another embodiment, the mesoporous silica particle comprises crystalline silica of one or more polymorphs, or the mesoporous silica particle comprises a mixture of amorphous and crystalline silica.

The mesoporous silica particle is contacted with the solution of the $Fe^{3+}$ salt and the reducing agent, where the silica particle is present at a concentration in a range of 5-50 mg, preferably 10-40 mg, more preferably 15-30 mg, or 15-20 mg per mL solution. In one embodiment, the $Fe^{3+}$ salt is present in the solution at a concentration in a range of 0.1-1.0 M, preferably 0.2-0.8 M, more preferably 0.3-0.7 M, or about 0.5 M. The $Fe^{3+}$ salt may be iron(III) acetate, iron(III) bromide, iron(III) chloride, iron(III) chromate, iron (III) citrate, iron(III) fluoride, iron(III) nitrate, iron(III) phosphate, iron(III) sulfate, or some other iron salt. Preferably the $Fe^{3+}$ salt is iron(III) chloride. In one embodiment, the reducing agent is zinc or magnesium, and is present in the solution at a concentration in a range of 0.001-0.02 wt %, preferably 0.005-0.01 wt % relative to a total weight of the solution.

In one embodiment, the solution consists of water, the $Fe^{3+}$ salt, and the reducing agent. In another embodiment, the solution does not contain a surfactant or a structure directing agent.

In one embodiment, the contacting may be carried out for a time in a range of 12-60 h, preferably 18-48 h, more preferably 20-28 h, or about 24 h, at a temperature in a range of 20–30° C., preferably 20-22° C., or about room temperature, while stirring or agitating the mesoporous silica particle in the solution. This produces the iron loaded silica particle, where $Fe^{3+}$ is located within the pores.

After the contacting, the iron loaded silica particle is removed from the solution and washed with water and/or an organic solvent including but not limited to ethanol, methanol, isopropanol, and acetone. The iron loaded silica particle may then be dried under vacuum or in a desiccator, or at a temperature in a range of 20-100° C., preferably 60-85° C. In one embodiment, following the drying, the iron loaded silica particle may again be contacted with the solution and then washed and dried. In total, the contacting, washing and drying may be repeated one time or two times.

Following the drying, the iron loaded silica particle is heated at 300-400° C., preferably 320-380° C., more preferably 330-370° C., or about 350° C. for a time period in a range of 2-12 h, preferably 4-10 h, more preferably 3.5-6 h, or about 7 h. This produces the iron oxide impregnated silica particle having iron oxide within its pores. In one embodiment, the iron oxide may be a continuous phase, where at least 70 wt %, preferably at least 80 wt %, more preferably at least 90 wt % of the iron oxide in one iron oxide impregnated silica particle is connected or agglomerated as one piece. The silica may be considered a template or support for the formation of the iron oxide. In one embodiment, the silica may be considered a hard template. Preferably the iron oxide is $Fe_2O_3$, more preferably $\gamma$-$Fe_2O_3$. In one embodiment, the iron oxide phase may be in the form of nanoparticles of iron oxide. In one embodiment, the iron oxide impregnated silica particle has a Fe to Si mass ratio in a range of 0.90-1.20, preferably 0.92-1.15, more preferably 0.95-1.05, or about 1.0.

In one embodiment, the iron oxide impregnated silica particle has a BET surface area in a range of 50-300 $m^2/g$, 250-360 $m^2/g$, preferably 80-240 $m^2/g$, more preferably 90-190 $m^2/g$, even more preferably 300-320 $m^2/g$, or about 240 $m^2/g$. In one embodiment, the iron oxide impregnated silica particle has an average pore diameter in a range of 2-10 nm, preferably 2.5-6.5 nm, more preferably 3.0-6.0 nm, or about 4-5 nm. In one embodiment, the iron oxide impregnated silica particle has an average diameter and/or sphericity that is substantially similar to the mesoporous silica particle. In another embodiment, the iron oxide impregnated silica particle and the mesoporous silica particle have average diameters that have a percent difference of less than 10%, preferably less than 5%. In another embodiment, the iron oxide impregnated silica particle has an average diameter in a range of 0.5-2.0 μm, preferably 1.0-1.9 μm, more preferably 1.5-1.9 μm, or about 1.7 μm.

In the method of making the microparticle drug carrier, the iron oxide impregnated silica particle is reacted with a base to remove the silica template, thus producing the microparticle drug carrier, which is free of silica. In this process, the average diameter of the particle, going from an iron oxide impregnated silica particle to the microparticle drug carrier, may be reduced by 20-70%, preferably 30-60%, more preferably 40-50% relative to the diameter of the iron oxide impregnated silica particle. In this step, the iron oxide impregnated silica particle may be contacted or mixed with a base, such as an inorganic base including but not limited to NaOH, KOH, LiOH, $Mg(OH)_2$, $Ca(OH)_2$, $Ba(OH)_2$, $NH_4OH$, or some other inorganic base. In alternative embodiments, an organic base may be used, such as sodium carbonate or sodium acetate. Preferably the base is NaOH or KOH, more preferably NaOH. The base may have a concentration in a range of 0.5-10 M, preferably 1-5 M, more preferably 2-7 M, or about 5 M, and may have a temperature in a range of 25-80° C., preferably 35-65° C., or about 50° C. The iron oxide impregnated silica particle may be present at a concentration in a range of 0.1-500 mg, preferably 1-400 mg per mL, and may be mixed or contacted with the base for a time in a range of 1-48 h, preferably 24 h. In one embodiment, the iron oxide impregnated silica particle may be removed and contacted with fresh base one or more additional times.

The microparticle drug carrier produced after the reaction with the base may be removed from the base and washed with water and/or an organic solvent, including but not limited to ethanol, methanol, isopropanol, or acetone. The microparticle drug carrier may be dried under vacuum or dried at 50-120° C., preferably 70-110° C., more preferably 80-105° C. for a time in a range of 1-24 h, 2-20 h, or 3-18 h.

The examples below are intended to further illustrate protocols for preparing, characterizing the microparticle drug carrier, and uses thereof, and are not intended to limit the scope of the claims.

Example 1

Results and Discussion
Preparation and Characterization of IO-MMMs

Fabrication of IO-MMMs was achieved based on a modified reverse hard-templating nanocasting methodology as outlined in FIG. 1. The first steps involve the production of the hard silica APMS template containing unique 3D pore-connected network and average pore size diameters of ~4-6 nm prepared according to previous work. See El-Boubbou, K., Schofield, D. A. & Landry, C. C. Enhanced Enzymatic Activity of OPH in Ammonium-Functionalized Mesoporous Silica: Surface Modification and Pore Effects. *J. Phys.*

*Chem. C* 116, 17501-17506 (2012); and El-Boubbou, K., Schofield, D. A. & Landry, C. C. Enhanced Enzymatic Thermal Stability and Activity in Functionalized Mesoporous Silica Monitored by 31P NMR. *Adv. Healthc. Mater.* 1, 183-188 (2012), each incorporated herein by reference in their entirety.

In situ reduction of iron(III) precursors during the impregnation process, followed by thermal treatment under an inert atmosphere, and finally removal of the silica template was done to generate the desired mesoporous material. In particular, iterative incorporation of APMS silica by aqueous solutions of iron (III) salt (i.e. FeCl$_3$) in the presence of a reducing agent, followed by a thermal sintering step produced the continuous iron oxide phase within the pores. Treatment with basic NaOH solution etched away the silica template affording IO-MMM constructs. Repeated impregnation allows maximal incorporation of the aggregated iron precursors filling the continuous mesopore system, which are turned to spherical iron oxide nanoclusters within the silica template during the reduction and heating treatments.

Figures 2A, 2B:
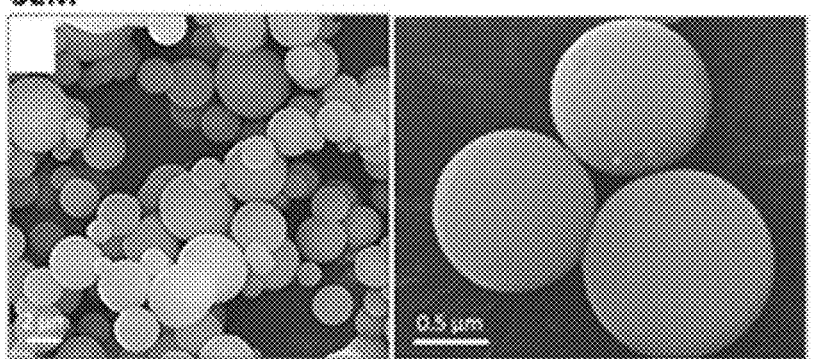
FIG. 2A is an SEM image of mesoporous silica microparticles, or acid-prepared mesoporous spheres (APMS).
FIG. 2B is a zoomed in SEM image of mesoporous silica microparticles, or APMS
Figures 2C, 2D:
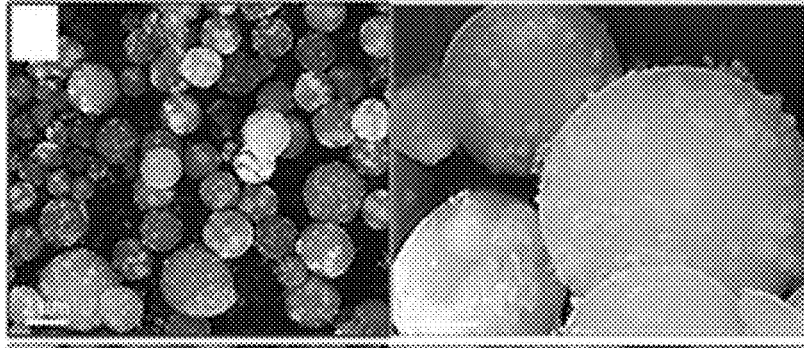
FIG. 2C is an SEM image of iron oxide impregnated silica particles, or APMS iron oxide intermediate (APMS-IO).
FIG. 2D is a zoomed in SEM image of iron oxide impregnated silica particles (APMS-JO).
Figures 2E, 2F:
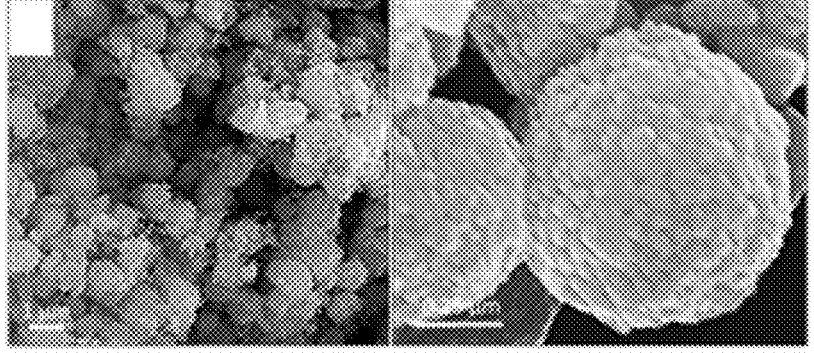
FIG. 2E is an SEM image of microparticle drug carriers, or iron oxide mesoporous magnetic microparticles (IO-MMM).
FIG. 2F is a zoomed in SEM image of microparticle drug carriers (IO-MMM).
Figure 2G:
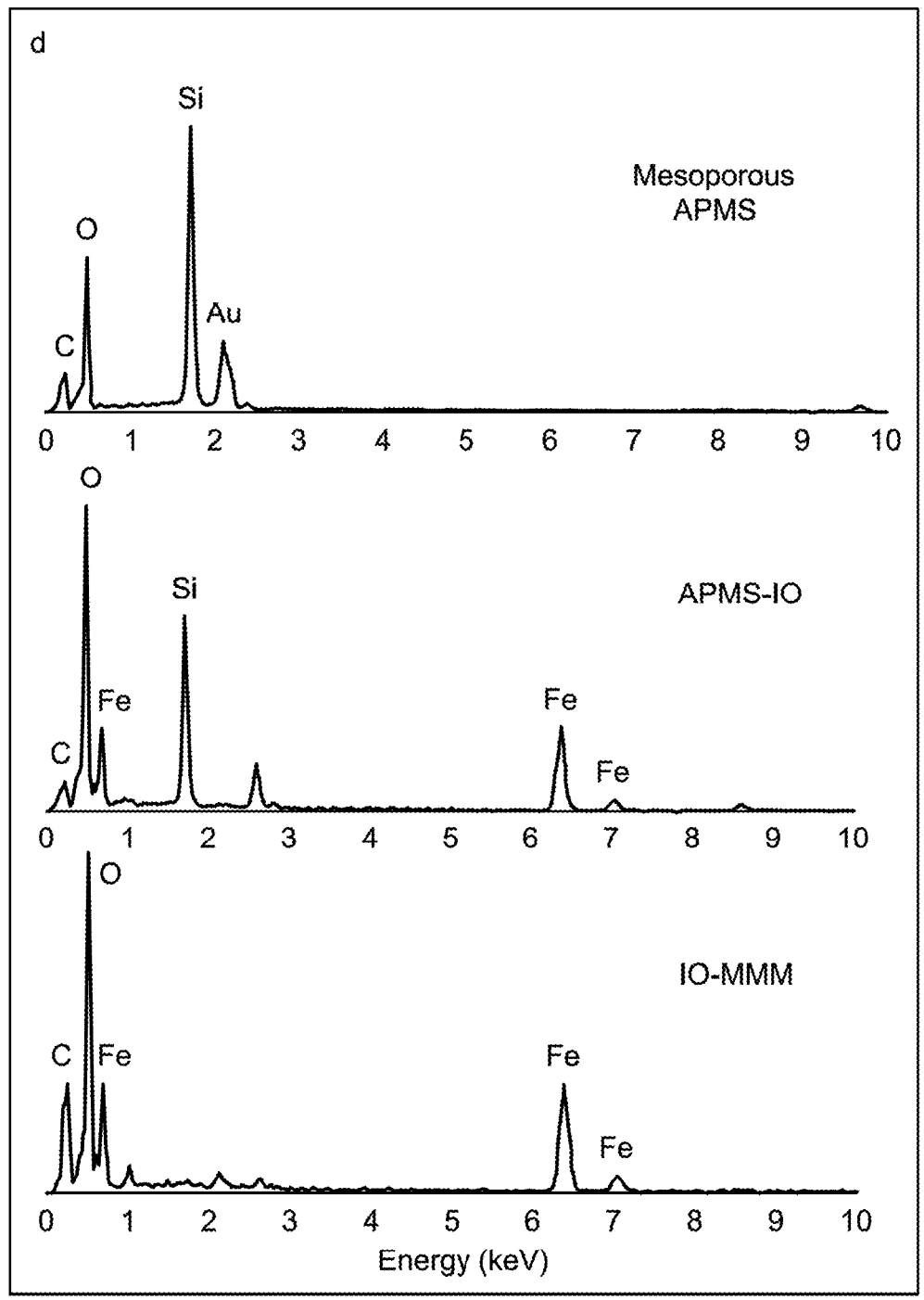
FIG. 2G shows EDX patterns of APMS, APMS-IO, and IO-MMM.
Figure 2H:
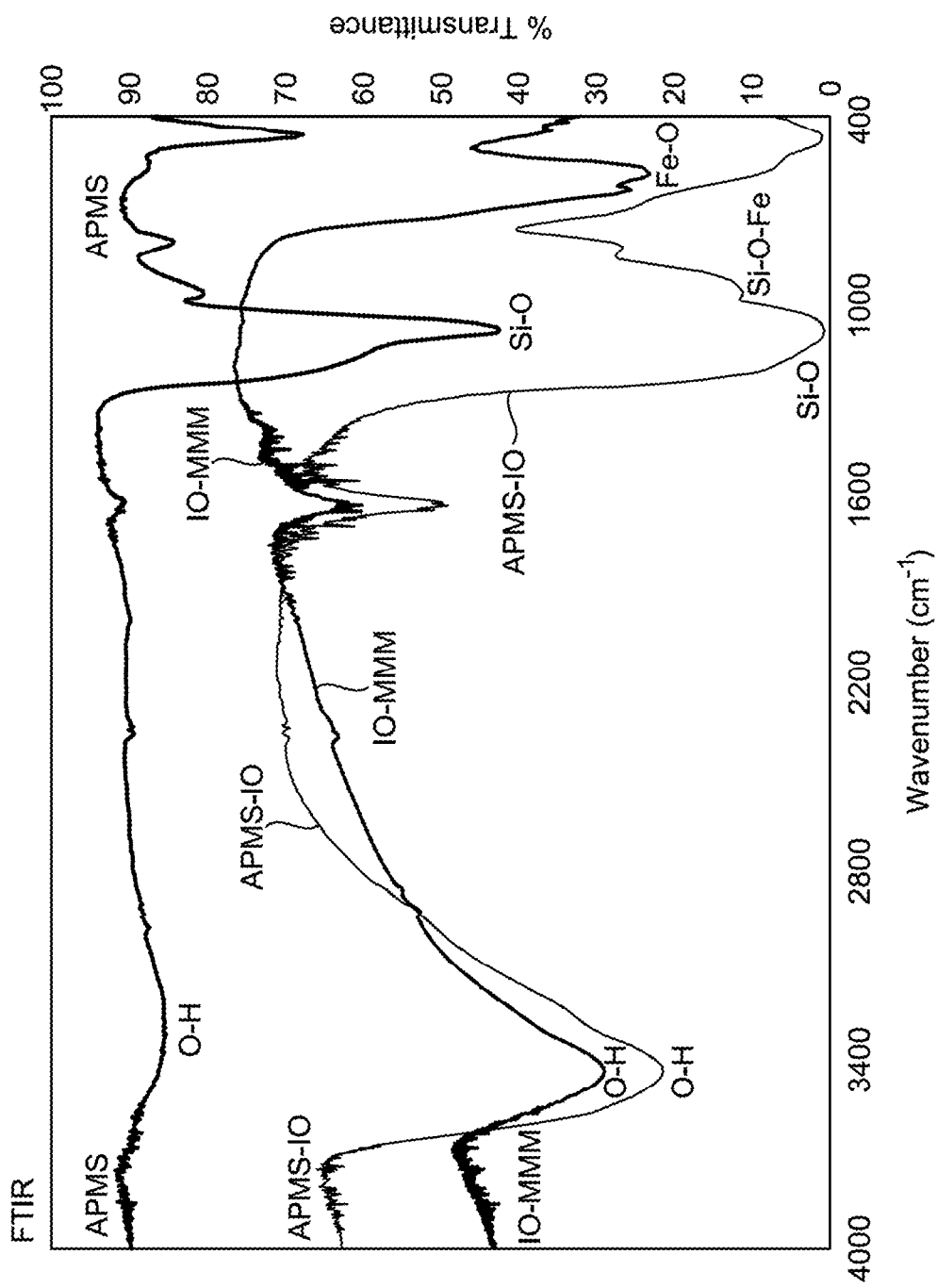
FIG. 2H shows FTIR spectra of APMS, APMS-IO, and IO-MMM.

The as-prepared IO-MMM mesoconstructs were thoroughly characterized by different spectroscopic techniques including scanning and transmission electron microscopy (SEM and TEM), energy-dispersive X-ray spectroscopy (EDX), nitrogen (N$_2$) physisorption porosimetry, X-ray diffraction (XRD), Fourier-transform infrared (FTIR), and dynamic light scattering (DLS). SEM images of the APMS silica host, the APMS-IO intermediate, and the templated IO-MMMs at different magnifications are shown in FIG. 2A-2F. Typical average APMS sizes of ~1.5 µm with a spherical morphology and practically uniform distribution was observed. While the surface of APMS seems to be clear, smooth, and free of surface cracks, APMS-IO intermediate appeared as IO-dotted architectures, and the final IO-MMM exhibited porous bumpy-like structures. EDX elemental analysis performed on selected SEM areas confirmed the presence of only Fe and O without any other element as impurity in the final replicated mesoporous material (FIG. 2G). EDX measurements on the intermediate samples reveal average atomic Fe/Si ratios of 0.5:1 corresponding to almost equal weight percentages of Fe to Si. This range fits with the relative iron quantities used for impregnation, indicating that iron is distributed quite homogeneously within the samples. FTIR spectroscopy for IO-MMMs showed the distinctive characteristic absorption stretching bands of iron oxide Fe—O (~500-600 cm$^{-1}$) and O—H (~3200-3600 cm$^{-1}$), with the disappearance of peaks in the region 960-1100 cm$^{-1}$ corresponding to Si—O (1100 cm$^{-1}$) and Si—O—Fe (960 cm$^{-1}$) stretching vibrations (FIG. 2H), confirming the EDX results. See Tüysüz, H., Salabaş, E. L., Weidenthaler, C. & Schüth, F. Synthesis and Magnetic Investigation of Ordered Mesoporous Two-Line Ferrihydrite. *J. Am. Chem. Soc.* 130, 280-287 (2008), incorporated herein by reference in its entirety.

Figures 3A, 3B, 3C:
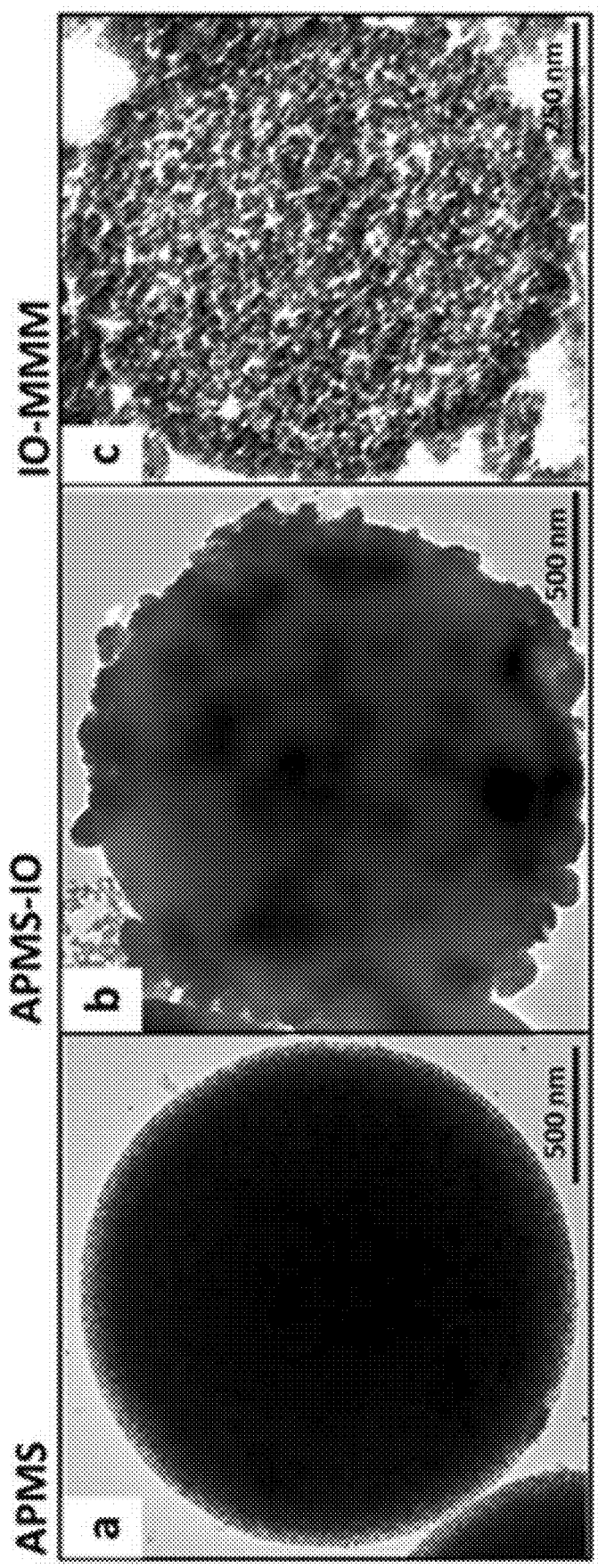
FIG. 3A shows a TEM image of an APMS.
FIG. 3B shows a TEM image of an APMS-IO.
FIG. 3C shows a TEM image of an IO-MMM.
Figures 3D, 3E:
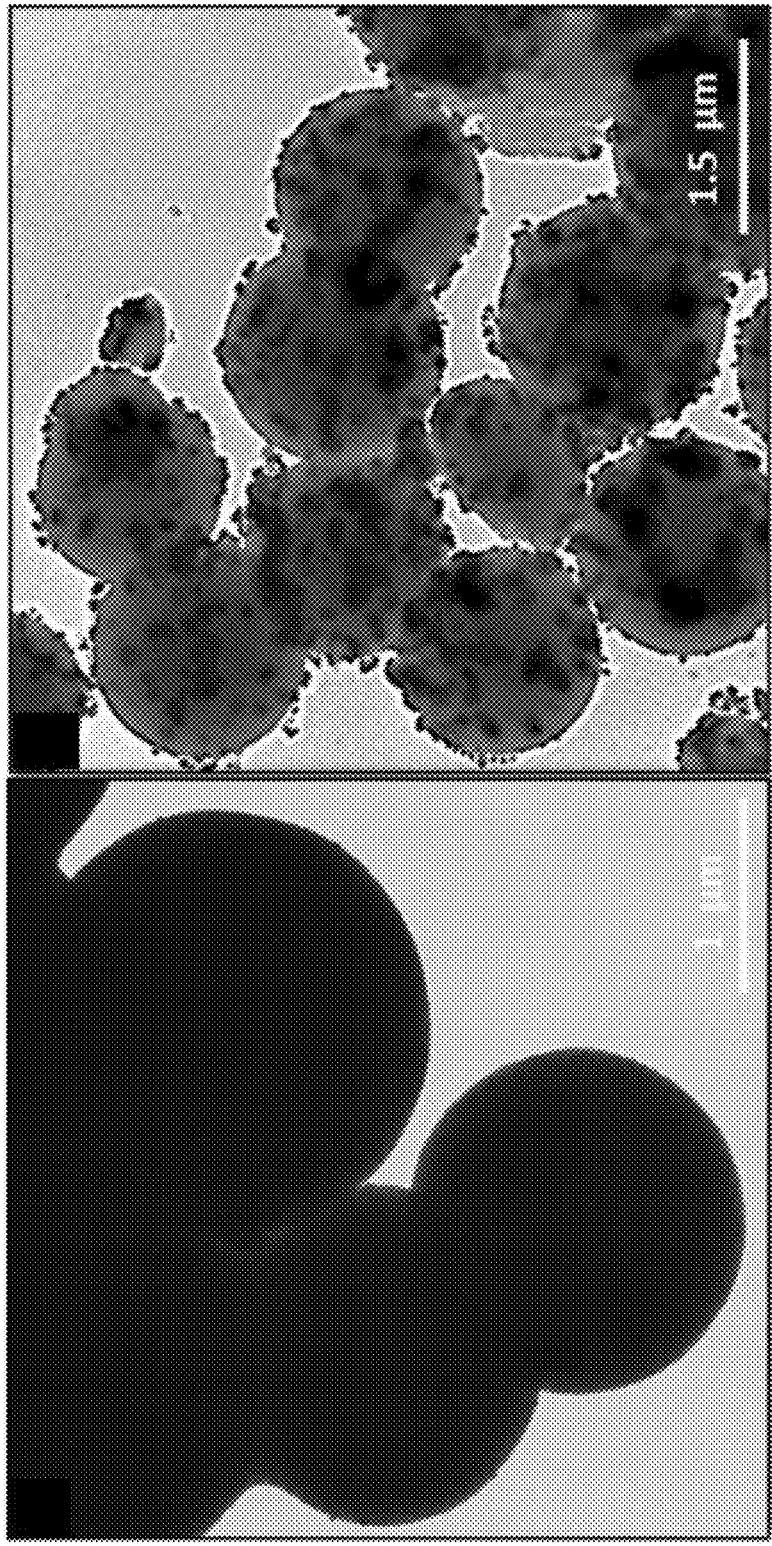
FIG. 3D shows another TEM image of an APMS.
FIG. 3E shows another TEM image of an APMS-IO.
Figures 3F, 3G:
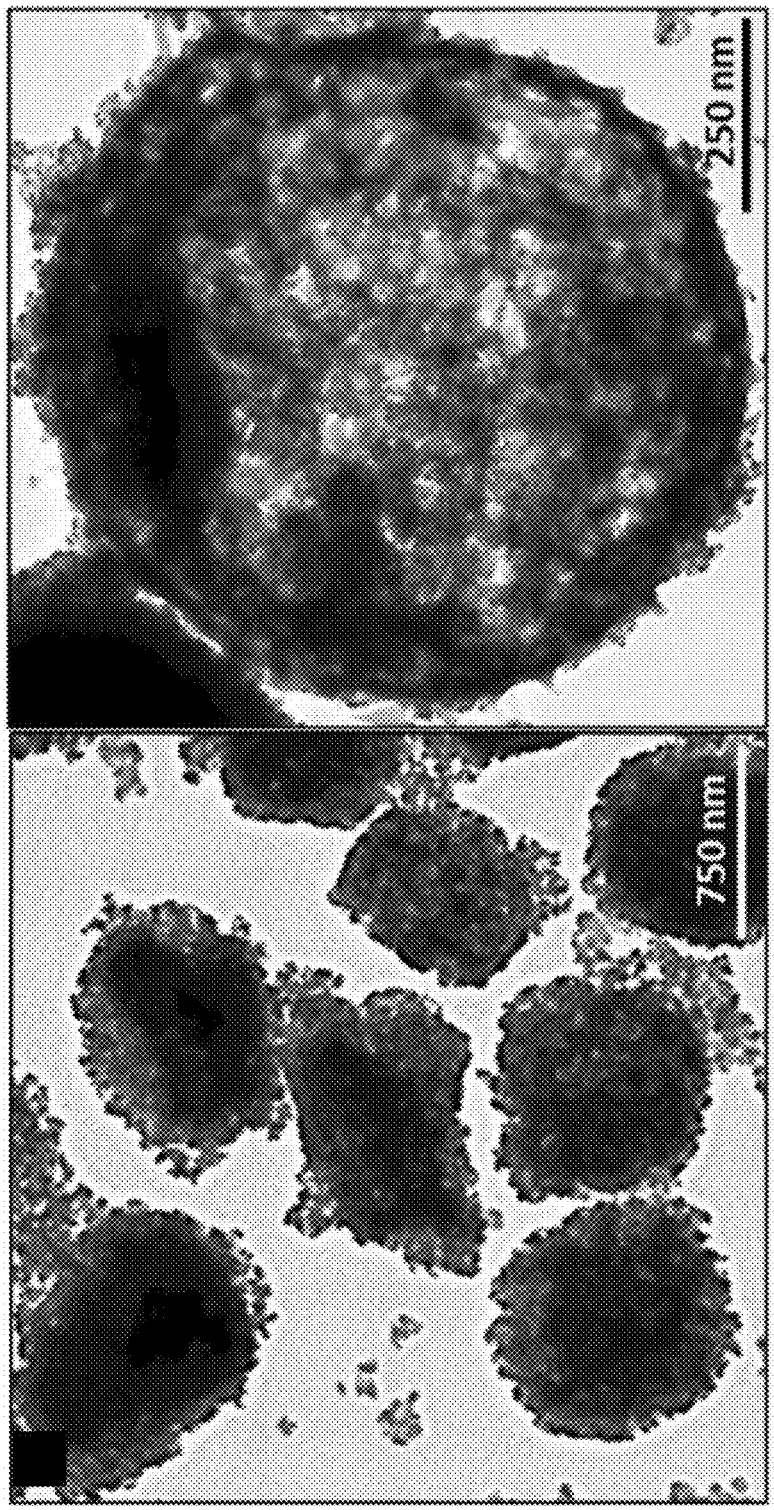
FIG. 3F shows another TEM image of an IO-MMM.
FIG. 3G shows another TEM image of an IO-MMM.
Figure 3H:
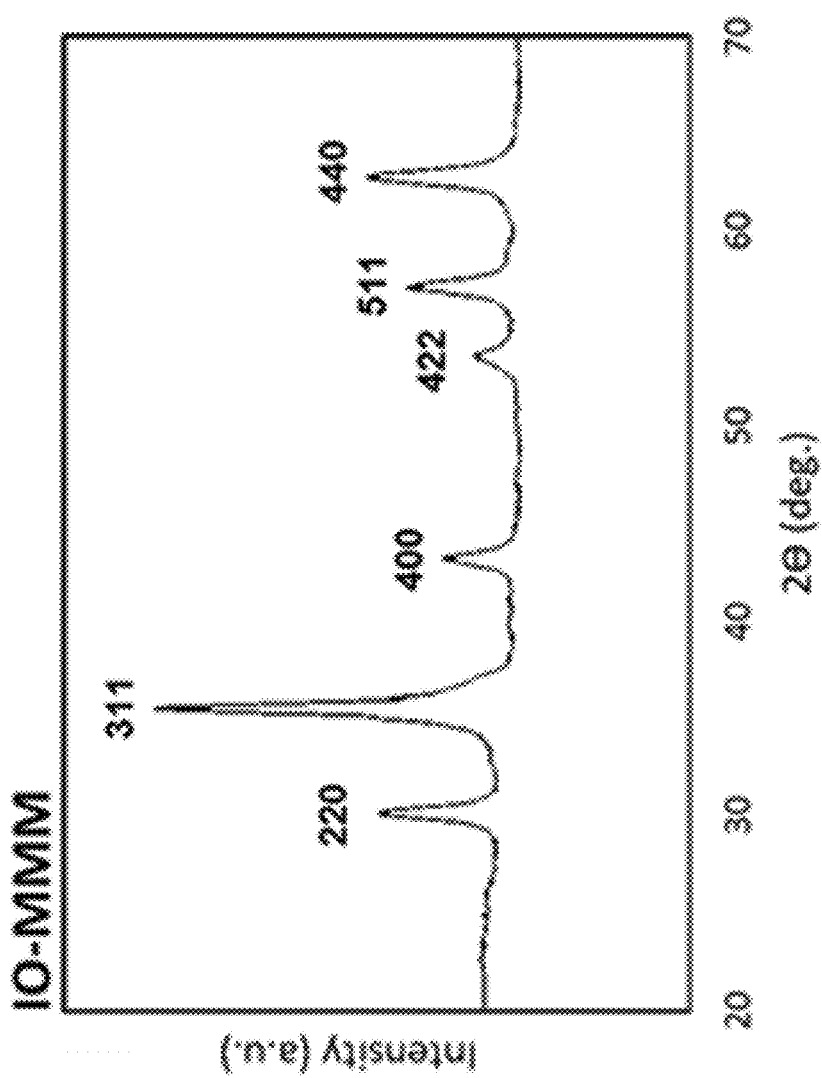
FIG. 3H shows a wide-angle XRD pattern of an IO-MMM.
Figure 3I:
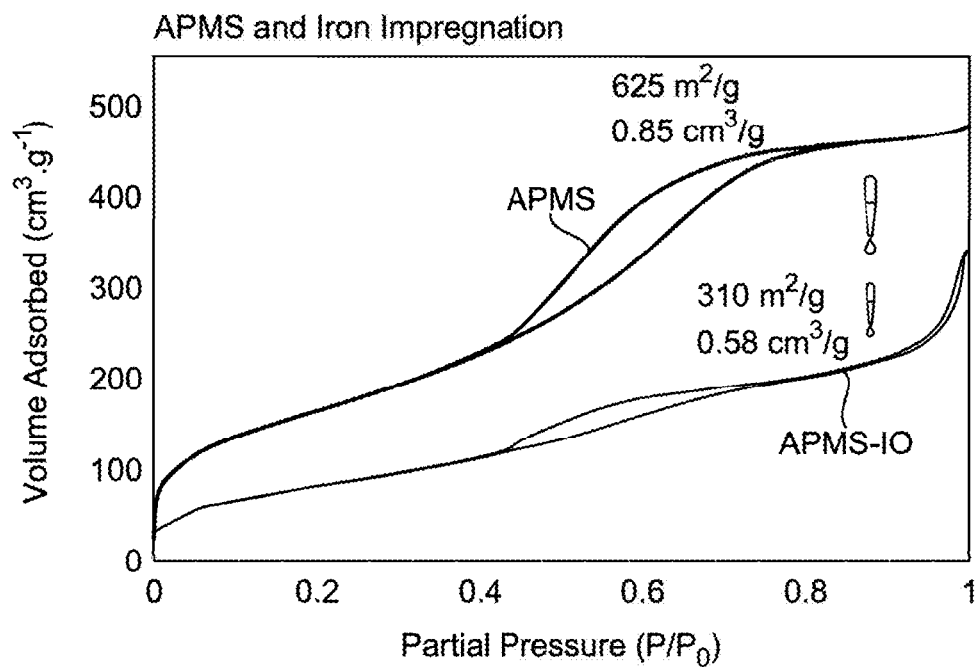
FIG. 3I shows a $N_2$ adsorption/desorption isotherm curve of APMS and APMS-IO.
Figure 3J:
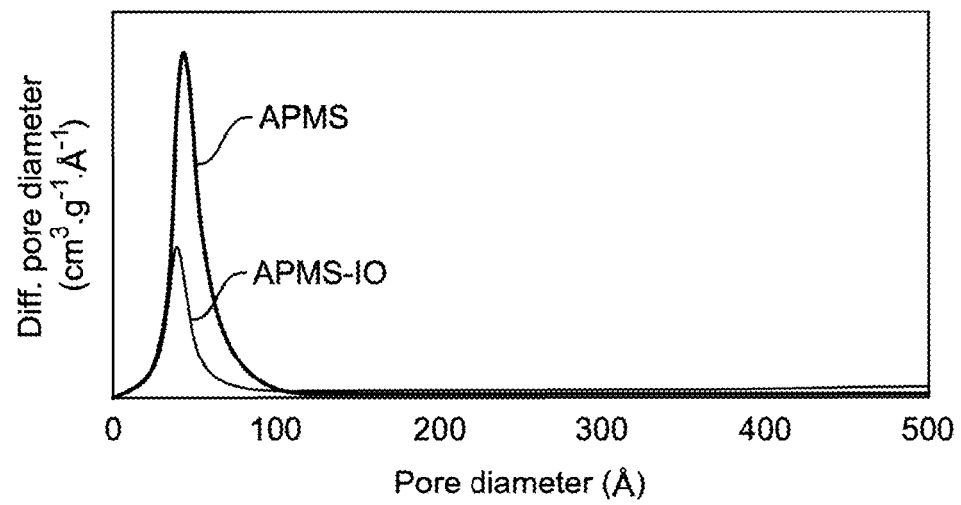
FIG. 3J shows a BJH (Barrett, Joyner, and Halenda) pore size diameter plot of APMS and APMS-IO.
Figure 3K:
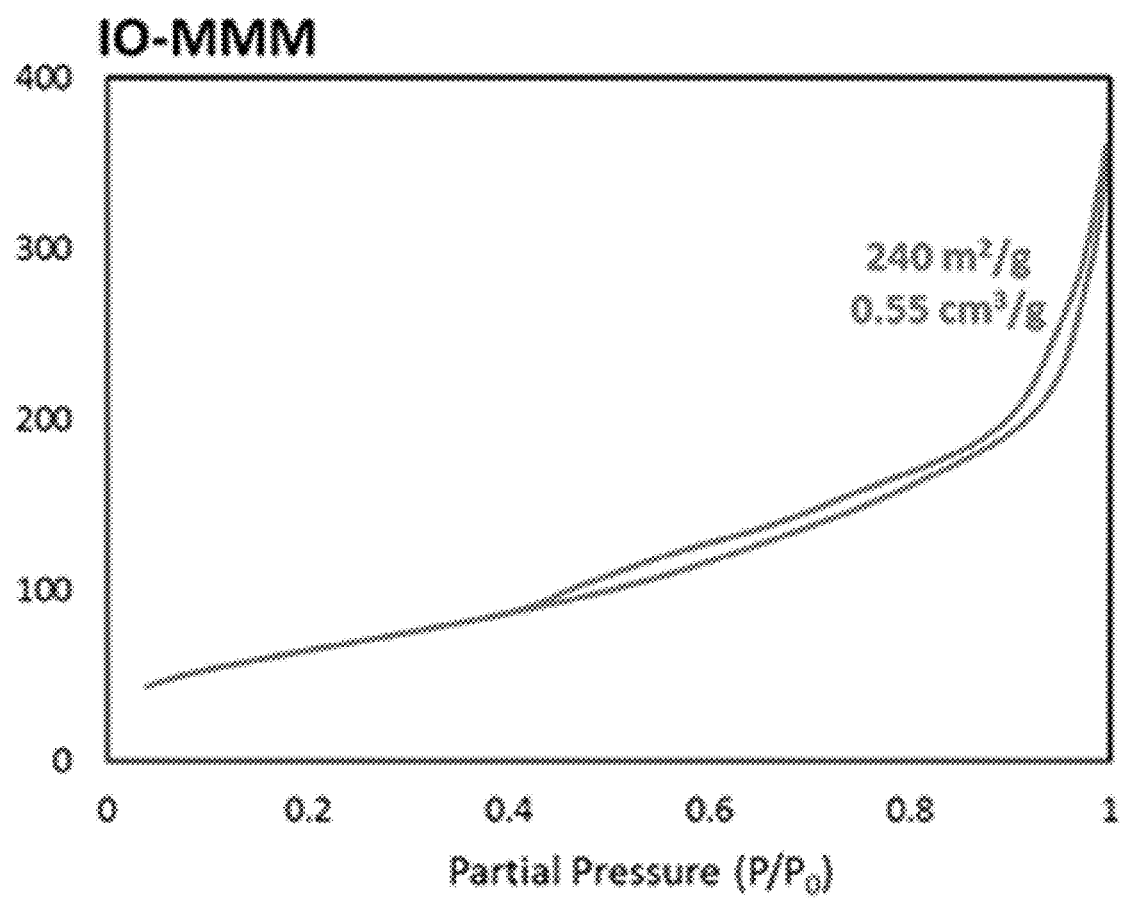
FIG. 3K shows a $N_2$ adsorption/desorption isotherm curve of IO-MMM.
Figure 3L:
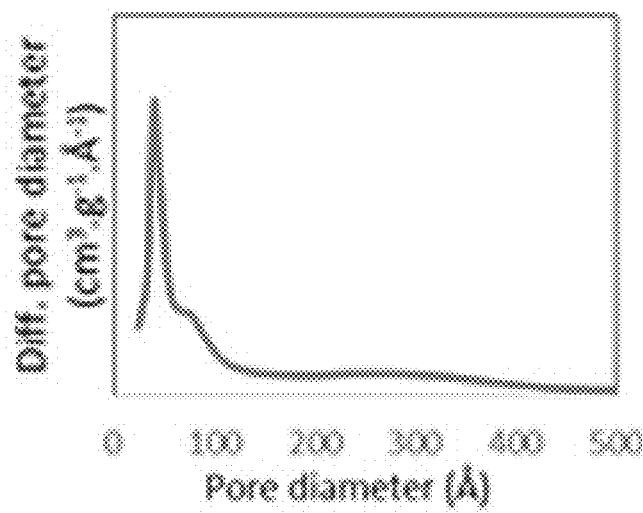
FIG. 3L shows a BJH pore size diameter plot of IO-MMM.

TEM images were then recorded to identify the mesostructure of the obtained IO-MMMs (FIG. 3D-3G). From a TEM image of a single particle, it is indicated that the original mesopore APMS system has been replicated and that the obtained material is composed of interconnected small nanoparticles that possess mesopores (FIG. 3A-3C). For APMS-IO intermediate and due to the electronic density contrast, iron oxide nanoclusters (in black) appear to be homogeneously distributed within the mesopores of APMS (in gray) (FIG. 3B). Very few agglomerated iron oxide species were observed independently, indicating that the impregnation occurred mostly inside the mesopores. In FIG. 3C, the light-contrast areas randomly distributed throughout the microparticle indicate the presence of replicated disordered interconnected porous network and also display the crystallinity of the IO-MMM framework. To further explore the phases and crystalline nature of IO-MMMs, wide-angle powder XRD was performed. XRD data revealed that the produced brown-colored material is $\gamma$-Fe$_2$O$_3$ (maghemite), with observed diffraction patterns in excellent agreement with previously published data for maghemite (JCPDS #039-1346) (FIG. 3H). See Lu et al. (2010); Kong, A., Wang, H., Li, J. & Shan, Y. Preparation of super paramagnetic crystalline mesoporous $\gamma$-Fe$_2$O$_3$ with high surface. *Mater. Lett.* 62, 943-945 (2008); and Shen, W., Qi, Z. & Naito, S. Unique preparation method for mesoporous $\gamma$-Fe$_2$O$_3$ simplified by using surfactant contained mesoporous silica as a hard template. *Mater. Res. Innov.* 19, 51-53 (2015), each incorporated herein by reference in their entirety. A d-value of 2.96 Å corresponding to the spacing of (220) planes confirmed the presence maghemite. See Yuan, S. M., Zhou, Z. & Li, G. Structural evolution from mesoporous $\alpha$-Fe$_2$O$_3$ to Fe$_3$O$_4$@C and $\gamma$-Fe$_2$O$_3$ nanospheres and their lithium storage performances. *Crystengcomm* 13, 4709-4713 (2011), incorporated herein by reference in its entirety. The diffraction peaks are quite low in intensity, signifying that the mesoporous walls are composed of crystalline framework. Most imperious, the porous nature of IO-MMMs was examined by N$_2$ adsorption/desorption experiments. As shown in FIG. 3I, successive iron loading (i.e. repetitive iron-impregnation to ensure maximal loading) indicated significant decrease in the surface area and pore volume of APMS-IO compared to the original calcined APMS silica host having Brunauer-Emmett-Teller, surface area (S$_{BET}$)=625 m$^2$/g and pore volume (V$_{pore}$)=0.85 cm$^3$/g, both indications of iron oxide incorporation/coating of the inner pore surfaces of the silica walls. The pore size distribution plots revealed a sharp average pore diameters (d$_{pore}$) centered at ~5 nm (FIG. 3J). Remarkably, N$_2$ physisorption isotherm of the final replicated IO-MMM (after thermal treatment and etching) showed that the obtained mesostructured iron oxides exhibit relatively high S$_{BET}$ of 240 m$^2$/g and V$_{pore}$ of 0.55 cm$^3$/g, with broad pore-size distribution having a major d$_{pore}$ at ~4 nm (FIGS. 3K-3L). The isotherm demonstrates a typical Type IV curve characteristic with a well-defined hysteresis loop, indicative of the presence of mesopores and consistent with the recently reported porosities for mesoporous iron oxides. See Jiao et al. (2006). Because of the disordered, interconnected nature of channels in APMS, the pore size distribution of the product is somehow broad as a result of random growth and orientation of iron oxide crystals within the APMS template during impregnations and subsequent thermal treatments. The obtained pore-size distributions, however, are in good agreement with the pore diameters understood for a replica structure of APMS. Also, the as-prepared IO-MMMs obtained here have higher surface areas than any other mesoporous iron oxide material reported in the literature, which is typically between 86 to 187 m$^2$/g. See Jiao et al. (2006); Shon et al. (2008); Kong et al. (2008); and Yuan et al. (2011), each incorporated herein by reference in their entirety and cited previously.

Hydrodynamic particle sizes and zeta potentials were then measured by DLS (FIGS. 4A-4E). Aqueous dispersion of IO-MMM in water depicted an average hydrodynamic size (D$_H$)=765 nm, which is approximately two-fold smaller than the average D$_H$ (~1500 nm) for APMS. This agrees well with the N$_2$ physisorption results, as replicated mesoporous materials should typically have smaller sizes than their templates. The relatively sharp peaks obtained further confirm the core size obtained by electron microscopy and pinpoints the uniform size distribution and stable dispersity of the as-synthesized IO-MMMs (PDI~0.5) in water. The intermediate APMS-IO revealed similar hydrodynamic sizes compared to APMS, showing major deposition of iron oxide nanoclusters inside the pores. However, a smaller population at ~190 nm corresponding to 20% of the total intensity was observed due to iron oxide agglomerates forming independently outside the pores, consistent with TEM results. Notably, zeta potential measurements indicated average zeta potential ($\xi$)=−12.03±4.62 mV for APMS template, $\xi$=−45.35±3.07 mV for intermediate APMS-IO, and $\xi$=−32.5±1.87 mV for IO-MMM, further corroborating successful incorporation of iron oxide and etching of the silica template. All these data combined show the formation of high surface area and large pore volume IO-MMM mesostructures. Moreover, the high density of hydroxyl groups on IO-MMM surfaces renders them water dispersible and suitable for biological assays.

It is worth noting that the synthesis of the iron oxide mesoporous constructs by incipient wetting of the APMS template via polyacrylic acid-stabilized iron oxide MNPs (PAA-MNPs) was previously attempted. Taken into account the strong chelating effect of PAA to the iron oxide surfaces and its previous successful use in the formation of mesoporous iron oxide nanospheres, it was believed that this may be an effective approach to prepare IO-MMMs. See Xuan et al. (2011). PAA-MNPs were synthesized using the "Ko-precipitation Hydrolytic Basic (KHB)" methodology resulting in uniform, stable, and colloidal ultrasmall MNPs of ~5 nm core diameter. See El-Boubbou, K. et al. Ultra-Small Fatty Acid-Stabilized Magnetite Nanocolloids Synthesized by In Situ Hydrolytic Precipitation. *Journal of Nanomaterials*, Article ID 620672, (2015); and El-Boubbou, K. Acid-Stabilized Iron-based Metal Oxide Colloidal Nanoparticles, and Methods Thereof. U.S. Pat. No. 10,629,339 B2 (2020), each incorporated herein by reference in their entirety. APMS was then impregnated with PAA-MNPs, followed by thermal treatment to facilitate decomposition of PAA polymer and fusion of IONPs. However, it seems that the pore diameters of APMS template are not able to host PAA-MNPs, which appear to mainly cluster and aggregate on the APMS surface rather than fill the pores. Nevertheless, TEM and $N_2$ physisoprtion isotherms confirmed the presence of some iron oxide mesoporous magnetic nanoclusters (IO-MMNs) with lower surface areas ($S_{BET}$=88.6 m$^2$/g and $V_{pore}$=0.157 cm$^3$/g) and smaller hydrodynamic sizes ~300 nm.

Example 2

Magnetic Behavior of IO-MMMs

Figure 4A:
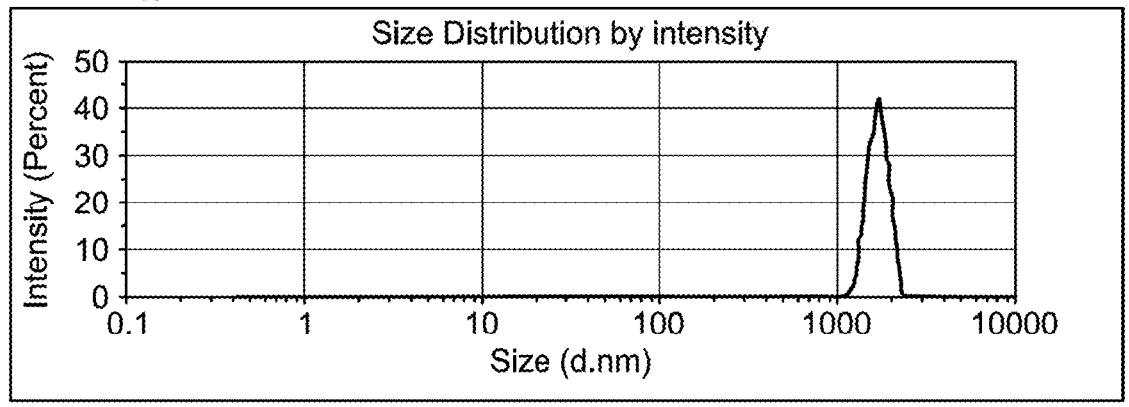
FIG. 4A shows the hydrodynamic size distribution of APMS.
Figure 4B:
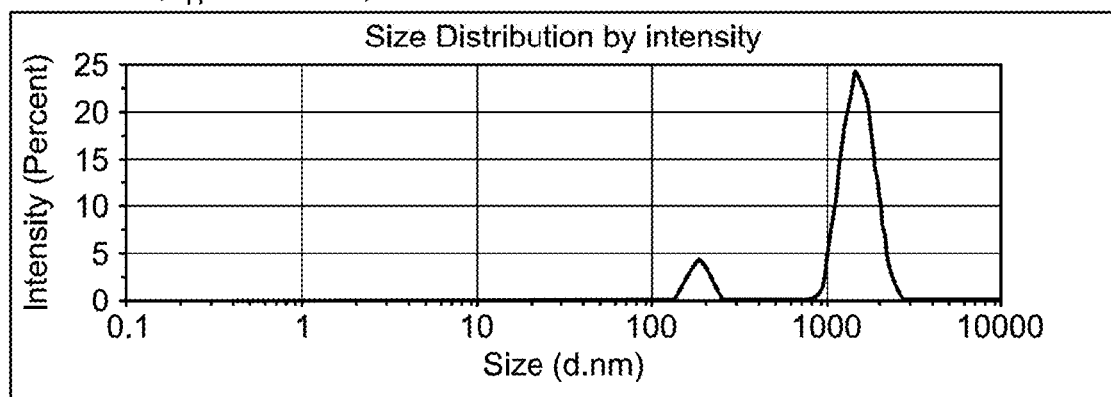
FIG. 4B shows the hydrodynamic size distribution of APMS-IO.
Figure 4C:
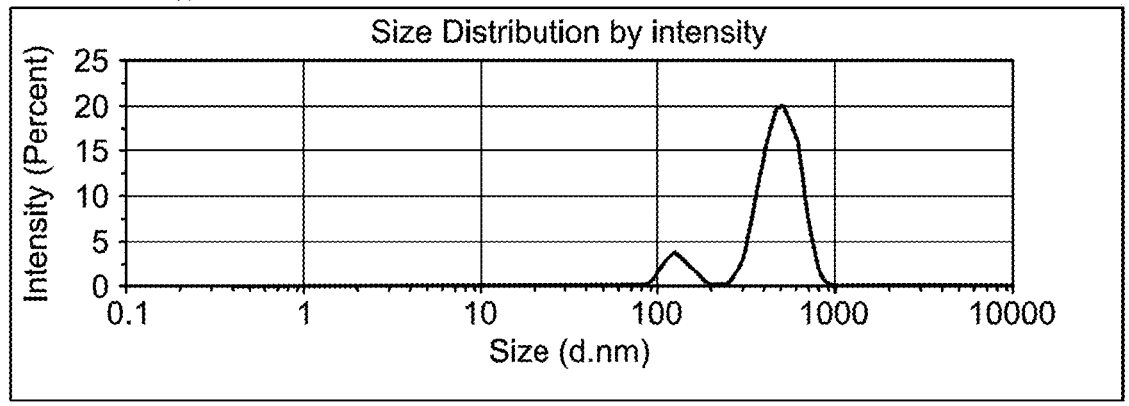
FIG. 4C shows the hydrodynamic size distribution of IO-MMM.
Figure 4D:
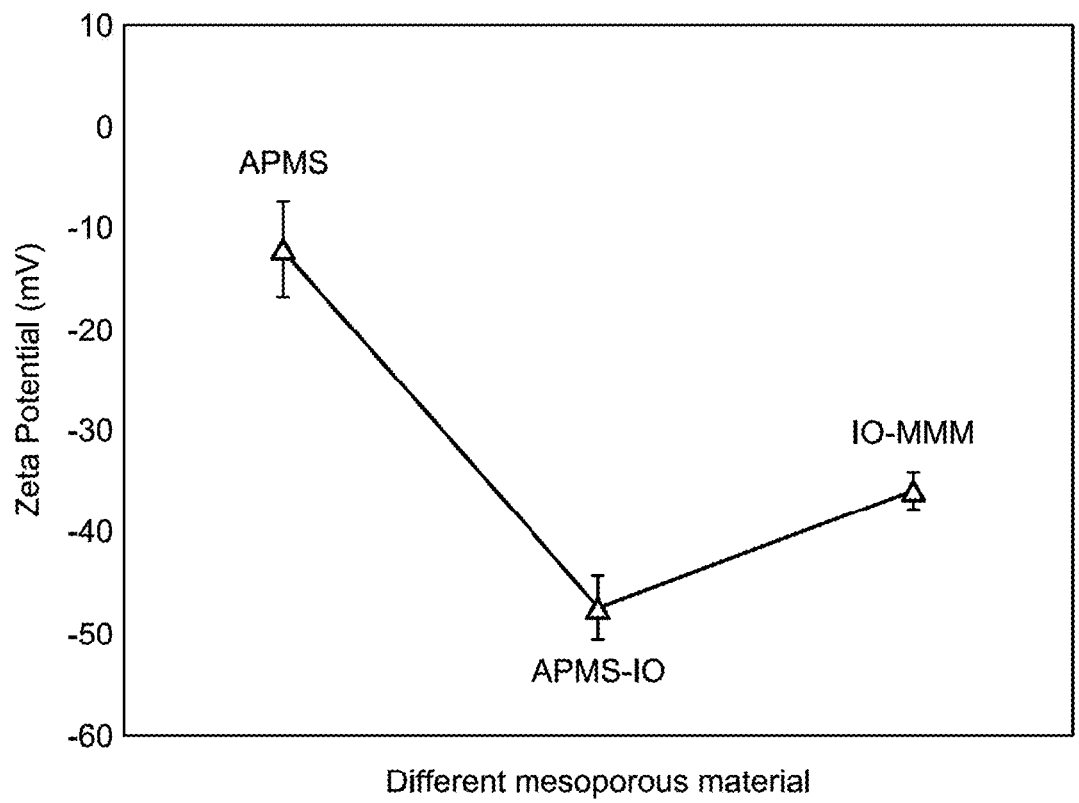
FIG. 4D shows the average zeta potential measurements of APMS, APMS-IO, and IO-MMM.
Figure 4E:
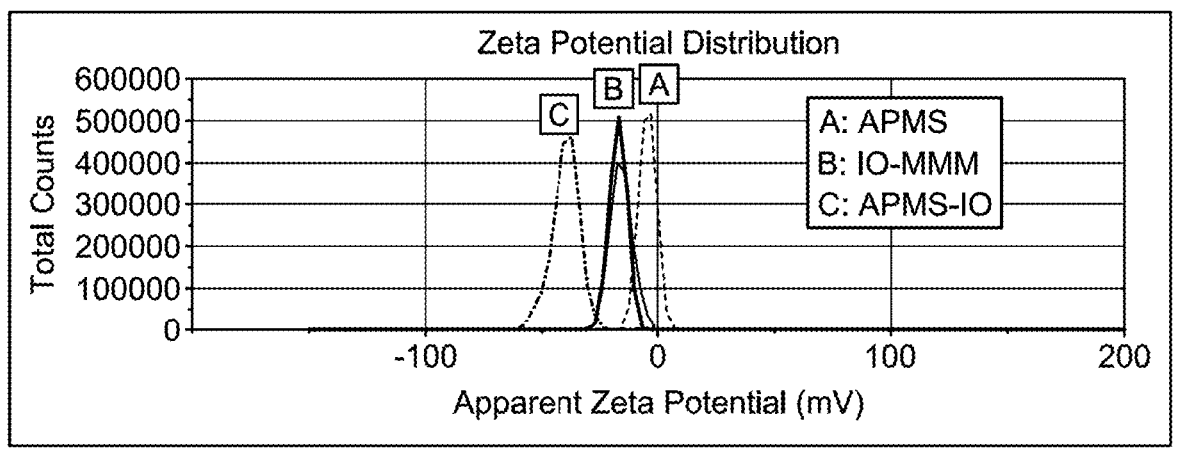
FIG. 4E shows the zeta potential distributions of APMS, APMS-IO, and IO-MMM.
Figure 4F:
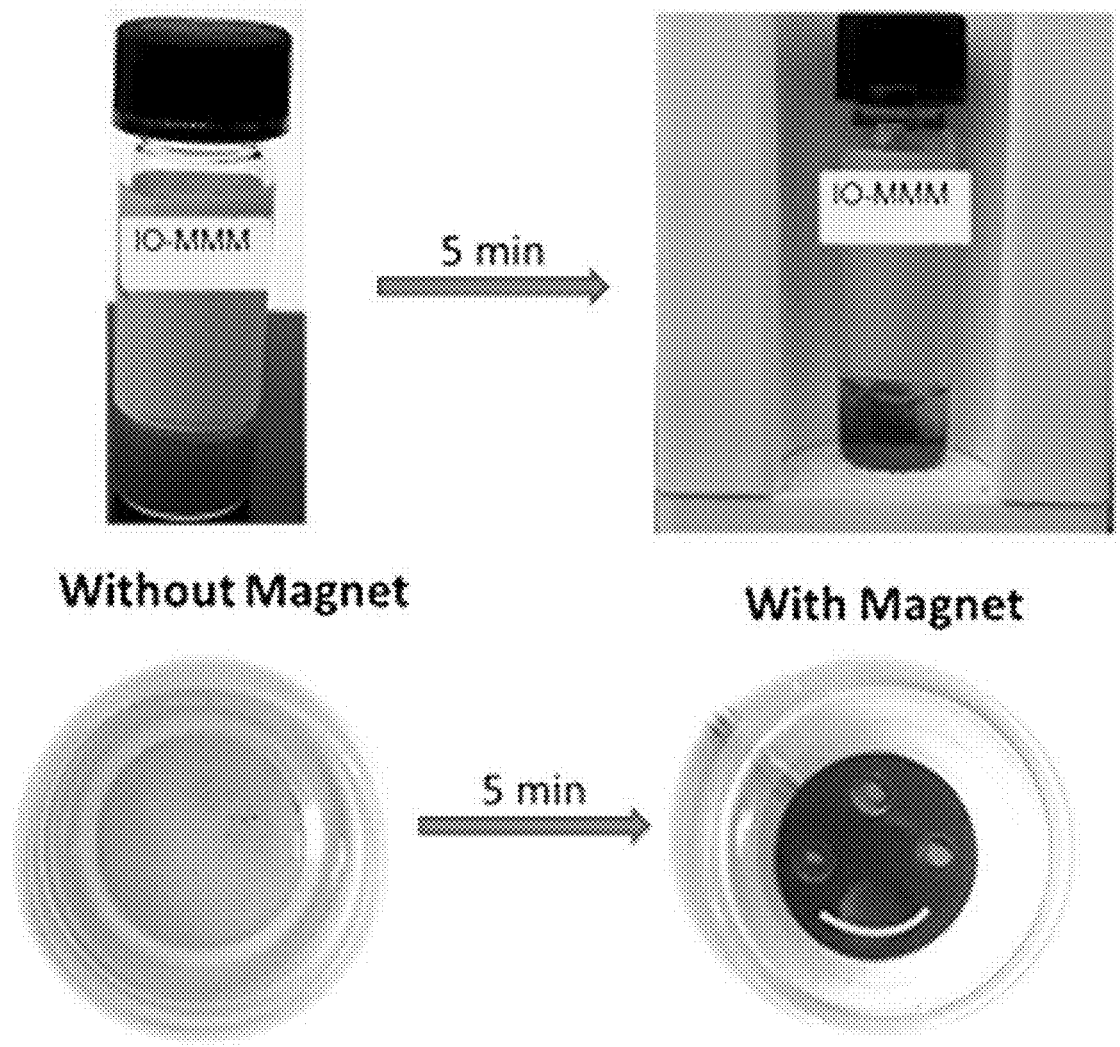
FIG. 4F shows the magnetic behavior of IO-MMMs being separated by a magnet from their aqueous dispersions.
Figure 4G:
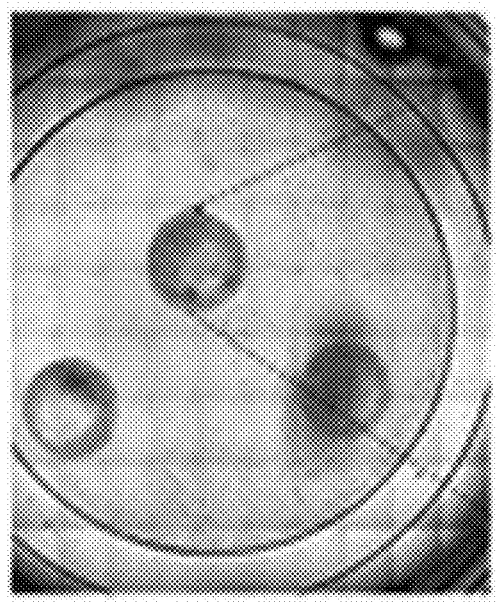
FIG. 4G shows a microscopy image of IO-MMM-treated cells stained with nuclei Hoechst in the presence of magnet.
Figure 4H:
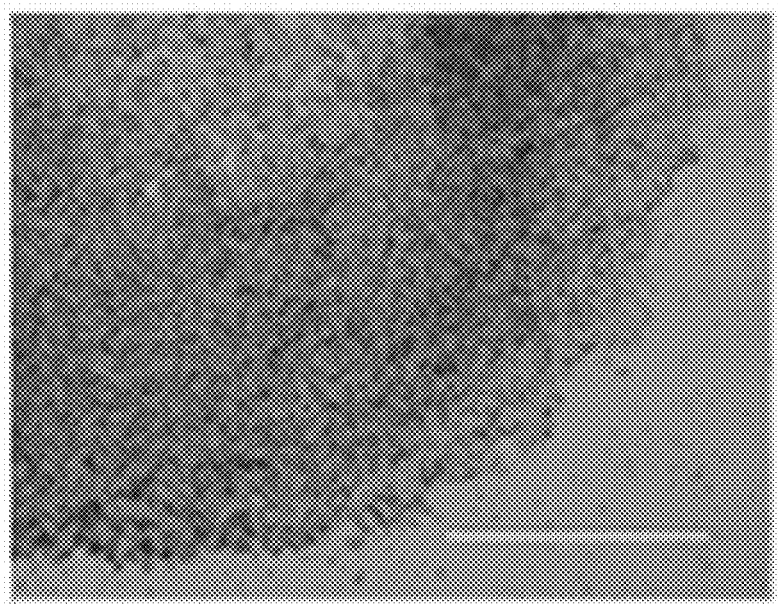
FIG. 4H is a zoomed in view of FIG. 4G.

Due to the intrinsic magnetic properties of iron oxide, one of the key advantages of the designed IO-MMMs is their potential use as magnetic imaging probes, and for magnetically-triggered drug delivery and clinical hyperthermia. See El-Boubbou (2018); Lu et al. (2013); and Benyettou et al. (2016). Magnetic resonance imaging has become the ideal imaging modality to test the biodistribution of magnetically-labeled cells and to monitor their fates noninvasively. Furthermore, human tissues are transparent to magnetic field, making the use of an external magnet an alternative and powerful approach to overcome limitations of light-enhanced or photo-responsive drug delivery. It was found that IO-MMMs can be easily separated by a magnetic force from their water dispersions within a few minutes, signifying the magnetic characteristics of the mesostructures (FIG. 4F). Furthermore, to test the capabilities of IO-MMMs to label cells, the response of IO-MMM-tagged cells was measured to a static magnetic field. As a proof of principle, KAIMRC1 cells were incubated with IO-MMMs, harvested, and transferred to petri dishes, one of which was located within a static magnetic field (FIG. 4G-4H). It was observed that in the presence of the magnet, cells were concentrated and aligned with respect to the magnetic field lines. In the absence of the permanent magnet, cells were rather disseminated in the petri dish. This demonstrates the possibility of concentrating and spatially locating IO-MMM-tagged cells, which is particularly useful for applications such as magnetic cell sorting. This magnetic IO-MMM platform may open new opportunities as promising materials not only for combined chemo/hormonal therapy but also for magnetically-triggered hyperthermia drug delivery applications.

Example 3

Drug Loading and Release

Figure 5A:
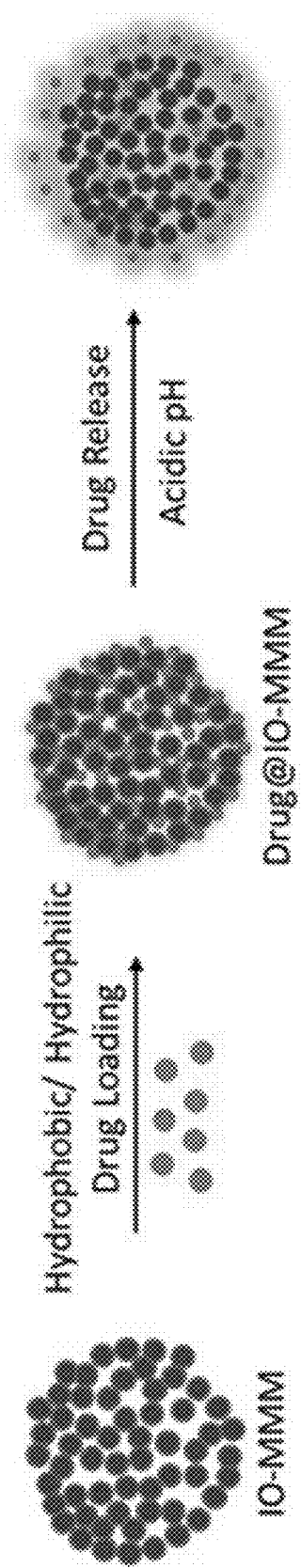
FIG. 5A represents a drug loading into IO-MMM and its pH-dependent release of the drug.
Figure 5B:
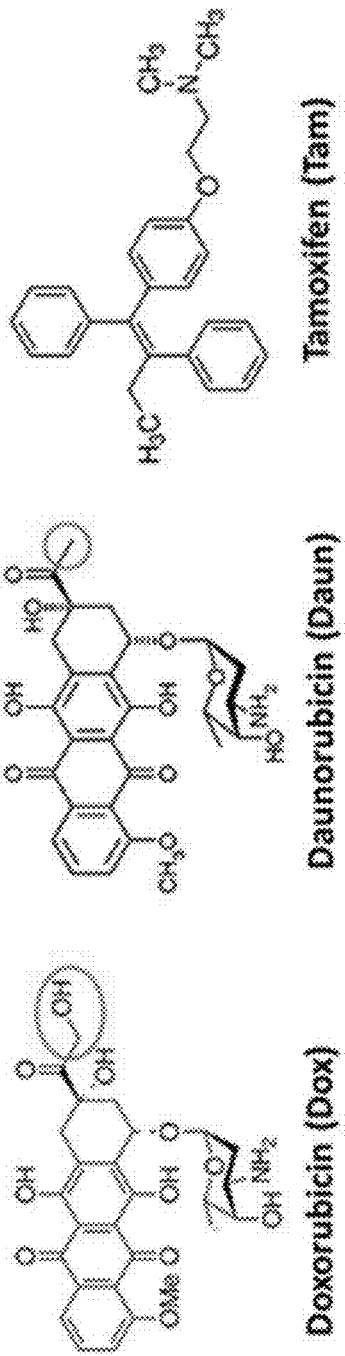
FIG. 5B shows the molecular formulas of anticancer drugs that may be loaded into the IO-MMM.
Figure 5C:
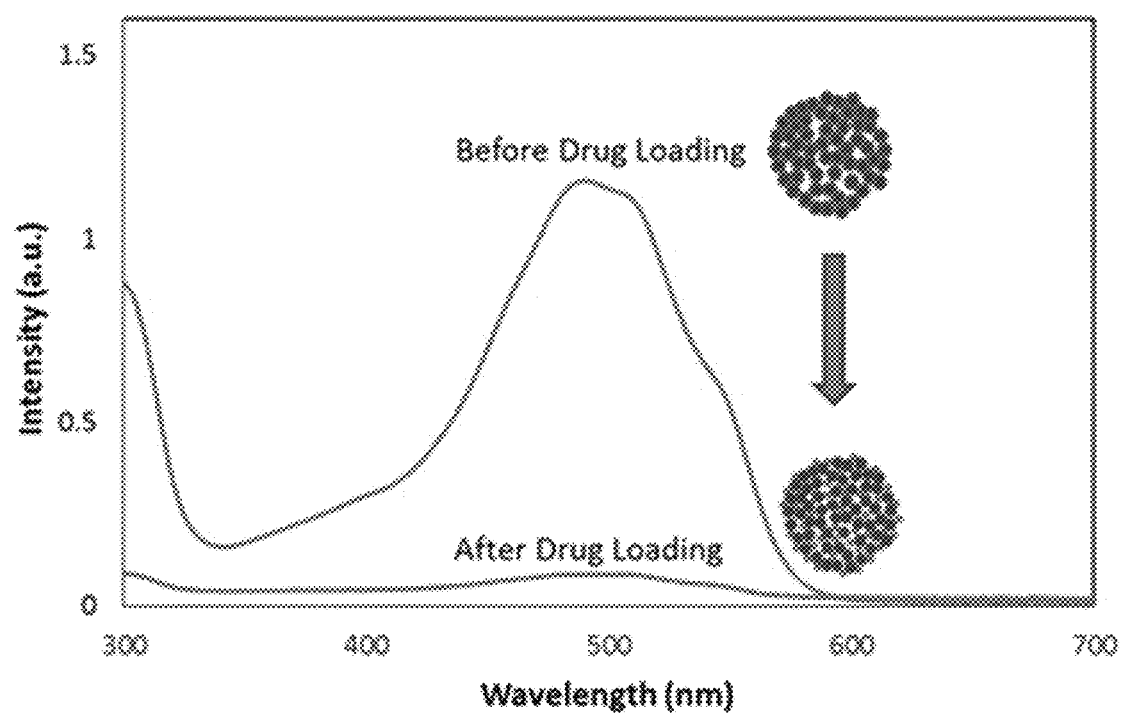
FIG. 5C shows representative UV-vis spectra of a drug solution (Dox) before and after loading into IO-MMMs.
Figure 5D:
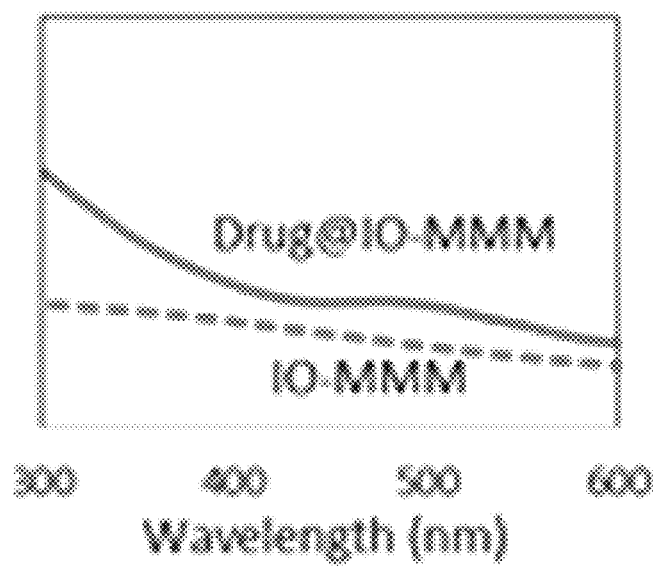
FIG. 5D shows UV-vis spectra of an aqueous dispersion of Dox@IO-MMMs showing the successful incorporation of Dox into the IO-MMM.

To test the utilization of IO-MMMs as drug carriers, the drug loading of two well-known hydrophilic chemotherapeutic drugs Doxorubicin (Dox) and Daunorubicin (Daun), and a hydrophobic hormonal anticancer drug Tamoxifen (Tam) was investigated (FIG. 5B), and their pH-dependent release in vitro was studied (FIG. 5A). Two different drug formulations (i.e. Dox@IO-MMM and Daun@IO-MMM) along with a combinatory Daun/Tam@IO-MMM formulation were employed. Nowadays in clinical practice, combination chemotherapy is emerging as an important protocol to enhance the therapeutic effects and reduce systemic side toxicities. For instance, Tam is typically used as hormonal therapeutic anticancer drug, in combination with other chemotherapeutic drugs, for the treatment of both early and advanced estrogen receptor-positive breast cancer. See O'Regan, R. M. & Jordan, V. C. The evolution of tamoxifen therapy in breast cancer: selective oestrogen-receptor modulators and downregulators. *Lancet Oncol.* 3, 207-214 (2002), incorporated herein by reference in its entirety. Nevertheless, as in the case of many chemotherapeutic drugs, side effects such as increased blood clotting, retinopathy, corneal opacities, and development of endometrial cancer are usually evident with Tam. Moreover, many of the anticancer drugs including Tam are hydrophobic, rising concerns of low solubility, bioavailability, drug toxicity and resistance, thus limiting their tangible clinical outcomes. Ideally for effective therapy, the drug delivery vehicle should carry large amounts of drugs, and then systemically release them to the cancerous cells and diseased tumor tissues in a controlled means. Hence, use of biocompatible systems for efficient delivery of hydrophilic/hydrophobic drugs or even combinatory drugs can provide enhanced therapeutic effects with reduced negligent side effects. While co-delivering systems have been explored by previous works, very few studies examined the use of iron oxide-based magnetic particles as drug delivery carriers for Tam, and none as a combinatory chemo/hormonal therapeutic vehicle. See Tang et al. (2018); Su et al. (2015); Llinàs, M. C. et al. Preparation of a mesoporous silica-based nano-vehicle for dual DOX/CPT pH-triggered delivery. *Drug delivery* 25, 1137-1146 (2018); Fang, J. et al. Quercetin and doxorubicin co-delivery using mesoporous silica nanoparticles enhance the efficacy of gastric carcinoma chemotherapy. *Int. J. Nanomedicine* 13, 5113-5126 (2018); Hu, F. X., Neoh, K. G. & Kang, E. T. Synthesis and in vitro anti-cancer evaluation of tamoxifen-loaded magnetite/PLLA composite nanoparticles. Biomaterials 27, 5725-5733 (2006); Heidari Majd, M. et al. Tamoxifen loaded folic acid armed PEGylated magnetic nanoparticles for targeted imaging and therapy of cancer. *Coll. Surf. B Biointerfaces* 106, 117-125 (2013); and Vivek, R. et al. HER2 Targeted Breast Cancer Therapy with Switchable "Off/On" Multifunctional "Smart" Magnetic Polymer Core-Shell Nanocomposites. *ACS Appl. Mater. Interfaces* 8, 2262-2279 (2016), each incorporated herein by reference in their entirety. Herein, simple adsorption of drugs onto IO-MMM mesostructures was chosen, as it has the advantage to preserve both the structure of the constructs and the loaded drugs. Up to 91% of Dox (227 µg Dox/mg of particles), 94% Daun (235 µg Daun/mg of particles), and 83% (165 µg Tam/mg of particles) can be loaded onto 10-MMMs, as evident from absorption spectroscopy. The loading efficiencies decreased when higher concentrations of the drug solutions were used (between 75-94% for Dox or Daun and 66-83% for Tam depending on the initial drug concentrations used). Representative UV-vis spectrum of Dox loading onto IO-MMMs to yield Dox@IO-MMMs is shown in FIG. 5C. Furthermore, UV-vis spectra of aqueous dispersion of Dox@IO-MMMs show the successful loading of drugs into IO-MMMs (FIG. 5D). Such high loading efficiencies are much greater than drug incorporation onto nonporous polymer-coated iron oxide MNPs (~80-150 µg of Dox/mg of MNPs) reported in previous work. See El-Boubbou, K. et al. Magnetic Fluorescent Nanoformulation for Intracellular Drug Delivery to Human Breast Cancer, Primary Tumors, and Tumor Biopsies: Beyond Targeting Expectations. *Bioconjugate Chem.* 27, 1471-1483 (2016); and El-Boubbou, K., Azar, D., Bekdash, A. & Abi-Habib, R. J. Doxironide Magnetic Nanoparticles for Selective Drug Delivery to Human Acute Myeloid Leukemia. *J. Biomed. Nanotechnol.* 13, 500-512 (2017), each incorporated herein by reference in their entirety. In fact, the high drug loading amounts of IO-MMM is chiefly attributed to its mesoporous nature with high surface area and pore volume packing the different drug molecules. The broad pore size distribution (dominantly at 4 nm) and the large surface areas of the pores could indeed help load plenty of anticancer drugs with suitable molecular sizes such as Dox which has a molecular size estimated to be ~1.37 nm. See Zhang, G. et al. Hydroxylated Mesoporous Nanosilica Coated by Polyethylenimine Coupled with Gadolinium and Folic Acid: A Tumor-Targeted T1 Magnetic Resonance Contrast Agent and Drug Delivery System. *ACS Appl. Mater. Interfaces* 7, 14192-14200 (2015), incorporated herein by reference in its entirety. FTIR spectroscopy was further extended to confirm the loading of drugs into the IO-MMM vehicles. Representative FTIR spectra showed that Dox@IO-MMMs has the same characteristic absorption bands as the free Dox with distinctive peaks at ~3400 cm$^{-1}$ and ~2900 cm$^{-1}$ due to O—H/N—H stretching and C—H stretching vibrations of the incorporated Dox, respectively. Moreover, the IR spectrum also showed the disappearance of the bands at 1730 cm$^{-1}$ (corresponding to C-13 carbonyl of Dox) and at ~3520 cm$^{-1}$ (N—H stretching vibrations of the primary amine), indicating the successful incorporation of Dox into IO-MMMs most probably via the involvement of —NH$_2$, —OH and carbonyl groups of Dox, consistent with previous reports. Daun@IO-MMMs and Daun/Tam@IO-MMMs were also characterized in the same manner and were found to have similar properties. Zeta potential and DLS measurements were also recorded for the three different drug@IO-MMM formulations. Average zeta potential values were found to be $\xi$=−24.9±1.55 mV for Dox@IO-MMMs, $\xi$=−26±1.01 mV for Daun@IO-MMMs, and $\xi$=−7.57±1.65 mV for Daun/Tam@IO-MMMs. Furthermore, size distributions ($D_H$~830 nm) revealed no significant change in the hydrodynamic sizes, pinpointing the narrow size distribution, homogeneity, and uniformity of the as-synthesized particles after drug loading. In brief, mild shifts in FTIR and lack of new unidentified peaks upon drug loading, along with UV-vis, size, and zeta measurements prove that the drugs are indeed incorporated in the pores of the mesostructures with no significant structural changes occurring to either the drugs or the mesoconstructs upon loading.

Figure 5E:
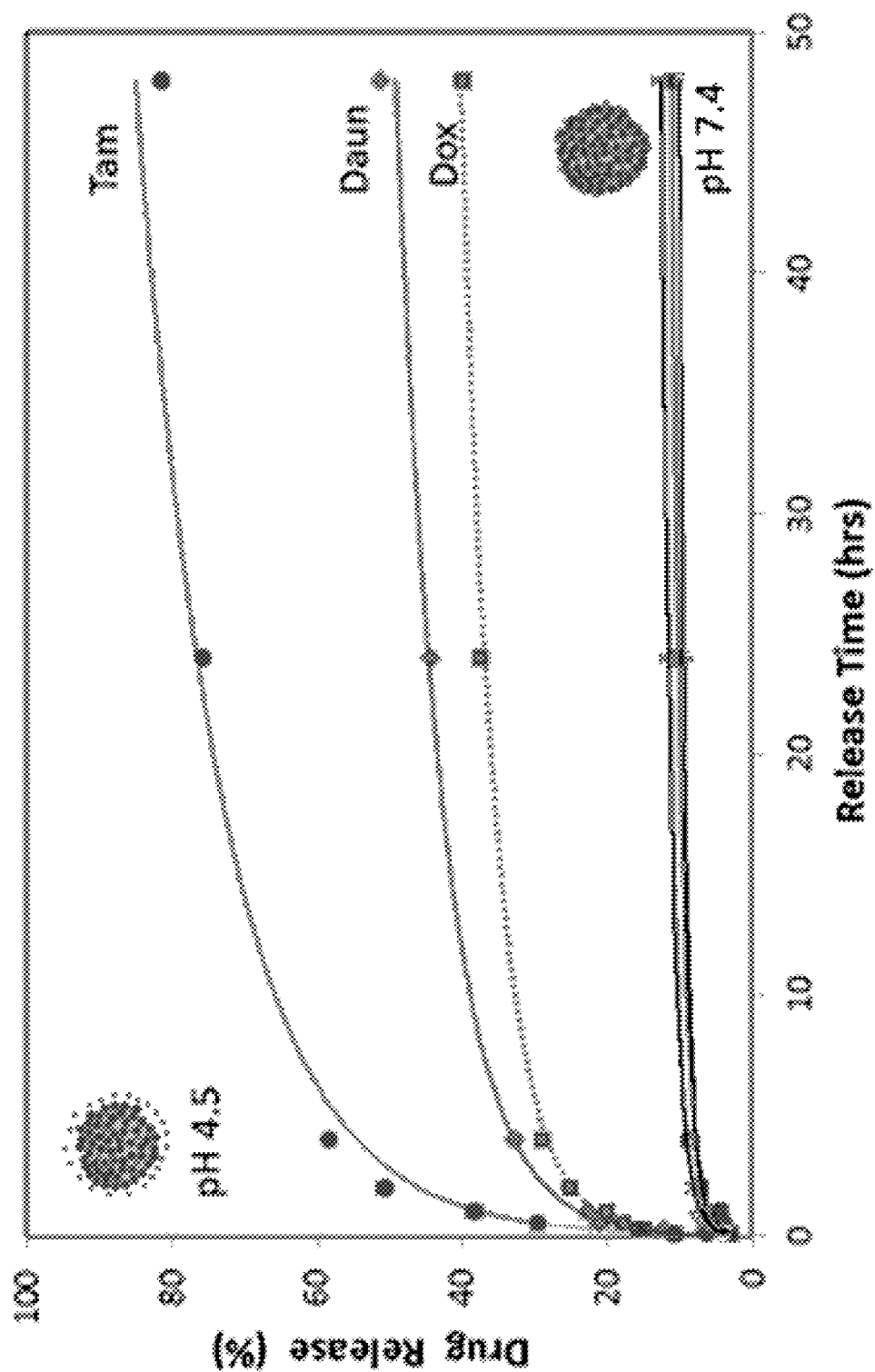
FIG. 5E shows drug release profiles of Tam, Daun, and Dox after loading into IO-MMM and at physiological and slightly acidic pH values.

With the drug@IO-MMMs in hand, their in vitro drug release profiles were first investigated in PBS buffer at two different pH values (FIG. 5E). Release of drugs from the IO-MMM mesostructures was found to be pH-dependent, allowing the drugs to be selectively released within the slightly acidic environments, but not at physiological neutral conditions. The total drugs released from IO-MMM constructs were about 40% Dox, 50% Daun, and 80% Tam at slightly acidic pH of 4.5 after 48 h, which is remarkably higher than that at physiological pH of 7.4 (only 7-10% after 48 h). In the case of the hydrophobic drug Tam, faster release at low acidic pH was observed compared to a more sustained Dox and Daun release, which might be ascribed to the physical absorption of the drugs inside the nanochannels. The initial burst release in the first hours is typical and is attributed to the rapid diffusion of drug molecules which interact weakly with the outer surfaces or near the pore entrances of the channels. From the release studies, it is evident that at neutral pH the drugs are tightly captured within the large surface areas of IO-MMM pores mainly due to electrostatic, hydrogen bonding, and van der Waals interactions between the drug molecules and particle/pore surfaces containing large number of hydroxyl groups. Due to the protonation of the hydroxyl groups on IO-MMM with the decrease in pH, electrostatic interactions between drugs and IO-MMM will be decreased, causing their release from the IO-MMM surface and mesoporous channels, consistent with previous observations. See Lu et al. (2013); and Chen, F. et al. Engineering of Hollow Mesoporous Silica Nanoparticles for Remarkably Enhanced Tumor Active Targeting Efficacy. *Scientific Reports* 4, 5080 (2014), each incorporated herein by reference in their entirety. For instance, Dox (pKa=8.25) is positively charged at neutral pH and can be adsorbed onto the negatively charged IO-MMMs. See Peng, M. et al. Dextran-coated superparamagnetic nanoparticles as potential cancer drug carriers in vivo. *Nanoscale* 7, 11155-11162 (2015), incorporated herein by reference in its entirety. Meanwhile, hydrogen bonding between the hydroxyl groups of IO-MMM and the corresponding groups of Dox could be disrupted by adjusting proton amounts at different pH values. See Guo et al. (2009); Peng et al. (2015); Huang, Y., Mao, K., Zhang, B. & Zhao, Y. Superparamagnetic iron oxide nanoparticles conjugated with folic acid for dual target-specific drug delivery and MRI in cancer theranostics. *Mater. Sci. Eng. C* 70, 763-771 (2017); and Yu, M. K. et al. Drug-loaded superparamagnetic iron oxide nanoparticles for combined cancer imaging and therapy in vivo. *Angew. Chem., Int. Ed.* 47, 5362-5365 (2008), each incorporated herein by reference in their entirety. A recent report attributed that Dox release at lower pH is due to the competitive binding of hydronium ions ($H_3O^+$) to the pores of mesoporous iron oxide. See Benyettou et al. (2016). Moreover, it has been shown that the coordination between Dox and Fe(III) is more labile at acidic pH, which is also consistent with the observed release at lower pH. See Mjos, K. D., Cawthray, J. F., Jamieson, G., Fox, J. A. & Orvig, C. Iron(III)-binding of the anticancer agents doxorubicin and vosaroxin. *Dalton Transactions* 44, 2348-2358 (2015), incorporated herein by reference in its entirety. All this proves that the drug release is faster at mildly acidic pH values as a consequence of the overall weakened interactions between the drugs and the particle/pore surfaces. This contained drugs at neutral pH with higher but smoother release rates at low pH is especially beneficial for combination therapeutic drug delivery, where the acidic environment in the tumor tissues and late endosomes/lysosomes in cells facilitates drug release from IO-MMMs, while the release in blood and other normal tissues are slow, reducing unwanted side effects. Furthermore, the initial burst release of drugs is preferable to achieve a sufficient initial drug dosage in tumor treatment, with the sustained release necessary to prevent further cancer proliferation. Similar pH-dependent drug release profiles with various nanomedicines have demonstrated better therapeutic and antitumor effectiveness in delivering chemotherapeutic drugs when tested both in vitro and in vivo. See Lu et al. (2013); Peng et al. (2015); Yu et al. (2008); and Gai, S. et al. Fibrous-structured magnetic and mesoporous $Fe_3O_4$/silica microspheres: synthesis and intracellular doxorubicin delivery. *J. Mater. Chem.* 21, 16420-16426 (2011), each incorporated herein by reference in their entirety. It is worth noting that particles where drug molecules are covalently conjugated to their surfaces usually exhibit much lower drug loading efficiencies and more difficulty in drug release due to the covalent binding. Thus, the prepared drug@IO-MMMs with the high drug payload capacity and the excellent pH-dependent drug release properties provide a notable level of therapeutic dose at the target cancerous cells and tumor tissues, resulting in effective cancer therapy.

Example 4

Biological and Cytotoxicity Assays

The cytotoxic effects of IO-MMM and drug@IO-MMM formulations towards different types of human breast (MCF7 and KAIMRC1) and colorectal (HCT8) cancerous cells, as well as normal primary cells were then examined using the thiazolyl blue tetrazolium bromide (MTT) cell viability assay. First, to demonstrate the potential utility of IO-MMMs as biocompatible delivery vehicles, the as-prepared IO-MMMs were tested against the different cancerous cells. IO-MMMs elicited no cytotoxic effects to any of the tested cells, even at high concentrations up to 100 μg/mL particles (FIG. 6A). Importantly, the different drug-loaded IO-MMM formulations (30 μg/mL particles; 7.5 μg/mL for Dox or Daun and 5.25 μg/mL for Tam) were found to be highly toxic to MCF7 and KAIMRC1 breast cancer cells as well as to HCT8 colorectal, with the least potency towards the normal primary cells (FIG. 6B). Interestingly, the combinatory Daun/Tam@IO-MMM formulation showed the most potent effects on the different cancerous cells tested with 10-fold and 5-fold enhanced cytotoxicities against the metastatic breast cancer and colorectal cancer cells in comparison to normal cells, respectively. It is believed that upon internalization, IO-MMMs release both Daun and Tam inside the cells, and, hence, enhance the cytotoxic effect through exhibiting synergistic anti-proliferative activities on the different cancerous cell lines. On the other hand, the free drugs, at equivalent concentrations, were found to be concurrently toxic to all the tested cells. This is in agreement with previously published reports. See El-Boubbou et al. (2016); and Ali, R. et al. Isolation and characterization of a new naturally immortalized human breast carcinoma cell line, KAIMRC1. *BMC Cancer* 17, 803 (2017), each incorporated herein by reference in their entirety. While the potency of drug@IO-MMMs towards the different cancerous cell lines was comparable to the potency of free drugs, it significantly decreased against the normal primary cells. This observed enhanced cytotoxicities of drug@IO-MMMs compared to free drugs towards cancerous cells, with the least sensitivity towards the normal cells, shows huge potential for IO-MMMs as efficient and selective drug delivery vehicles.

Figure 7A:
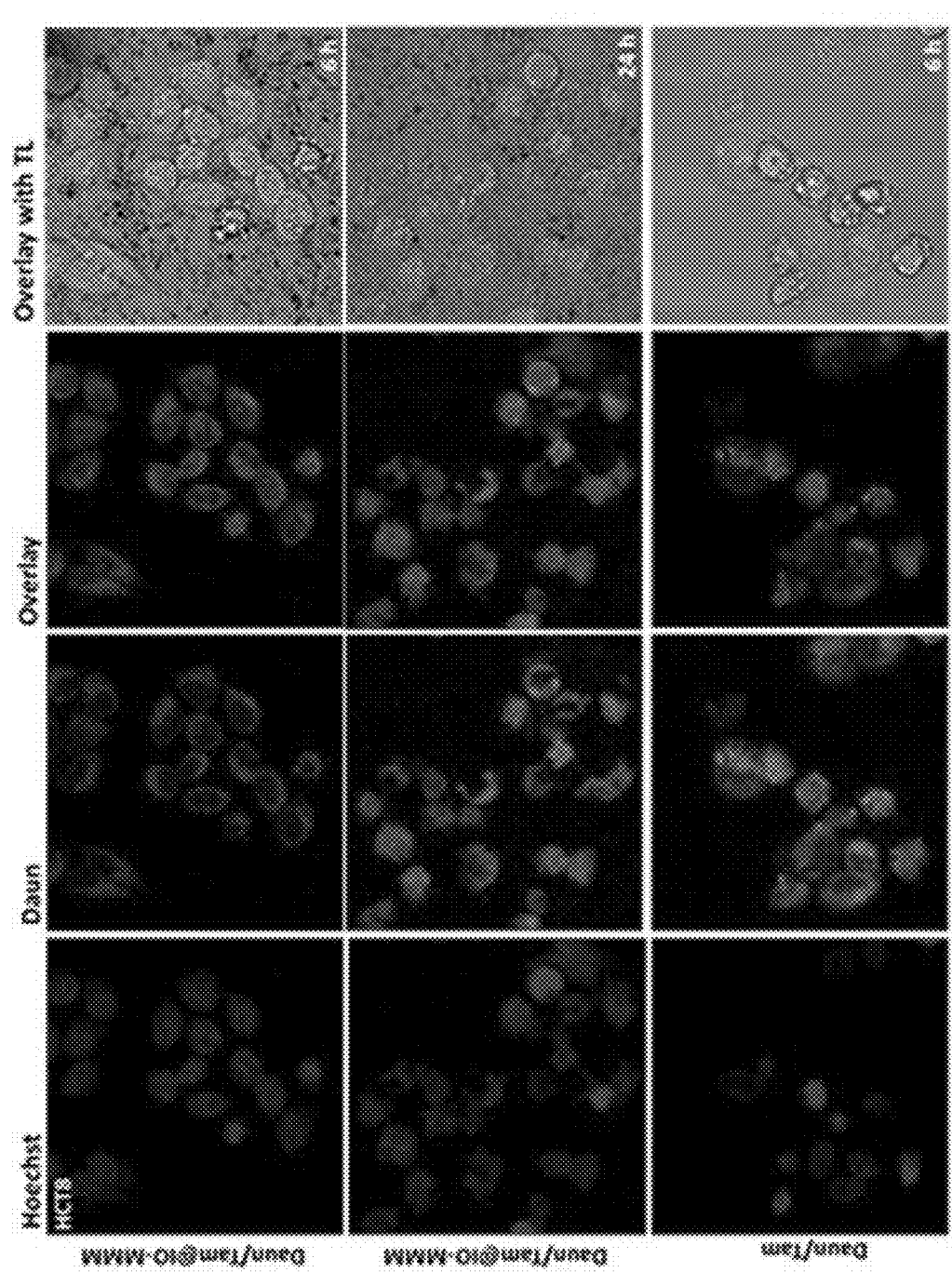
FIG. 7A shows live confocal microscopy images of colorectal HCT8 being treated with Daun/Tam@IO-MMMs (10 µg/mL particles; 2.50 µg/mL Daun; 1.75 m/mLTam) after 6 and 24 h, and HCT8 being treated with equivalent concentrations of free Daun/Tam after 6 h.
Figure 7B:
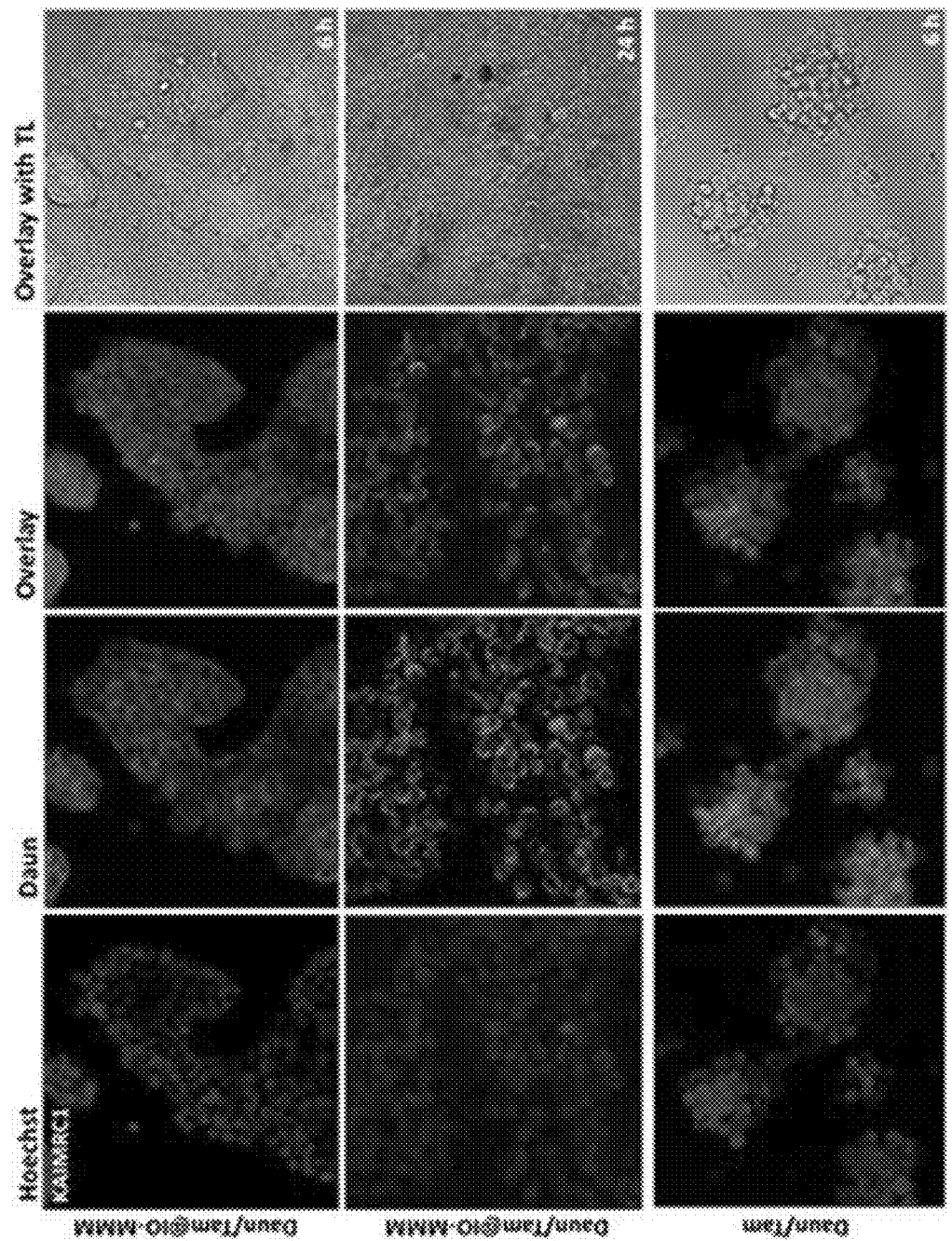
FIG. 7B shows live confocal microscopy images of breast KAIMRC1 being treated with Daun/Tam@IO-MMMs (10 µg/mL particles; 2.50 µg/mL Daun; 1.75 µg/mLTam) after 6 and 24 h, and breast KAIMRC1 being treated with equivalent concentrations of free Daun/Tam after 6 h.
Figure 7C:
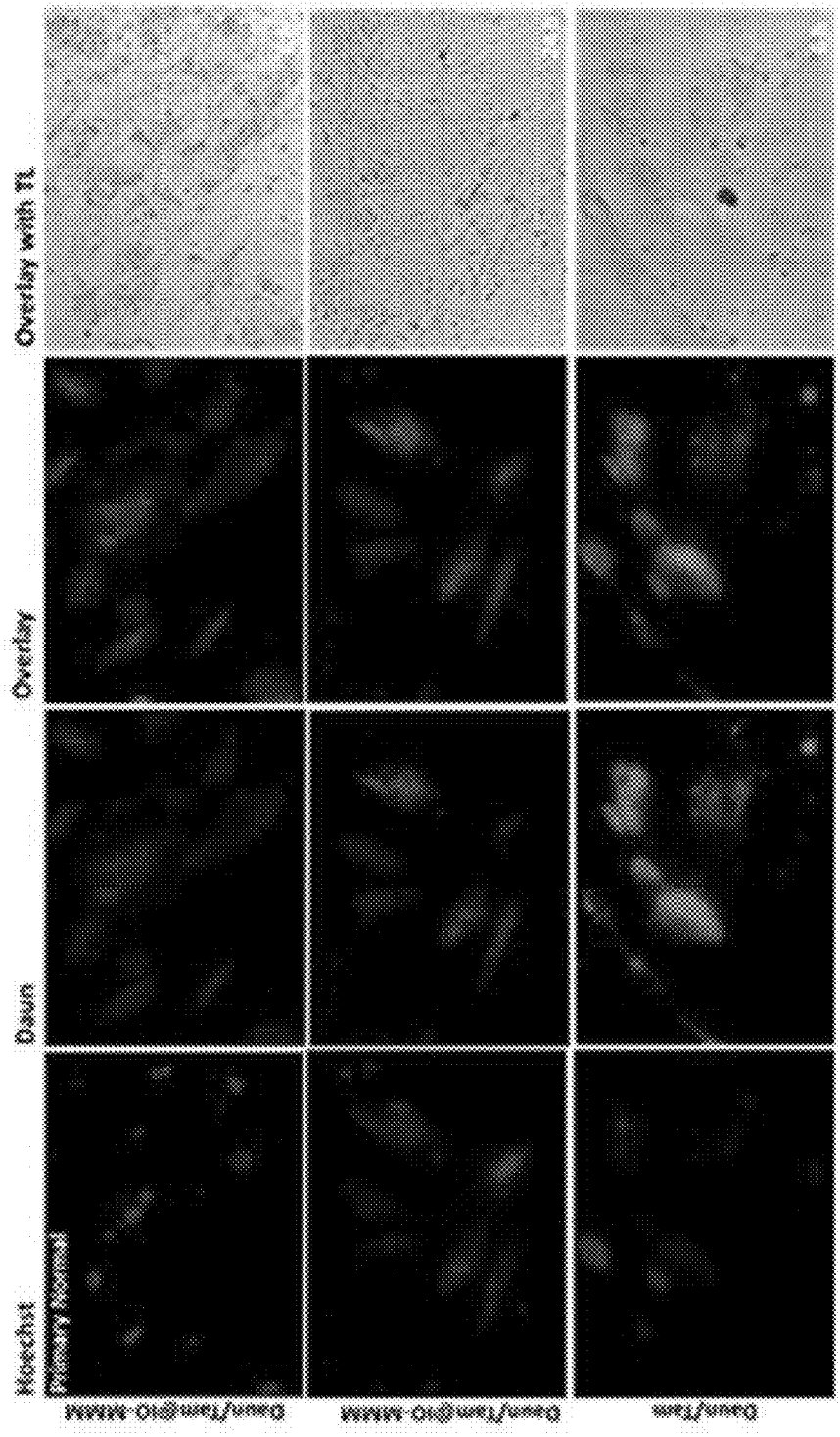
FIG. 7C shows live confocal microscopy images of primary normal cells being treated with Daun/Tam@IO-MMMs (10 µg/mL particles; 2.50 µg/mL Daun; 1.75 µg/mL-Tam) after 6 and 24 h, and primary normal cells being treated with equivalent concentrations of free Daun/Tam after 6 h.

To explore the route and intracellular drug delivery of the drug@IO-MMM constructs to the different cell lines, confocal laser scanning microscopy (CLSM) was performed. To mimic physiological conditions, live confocal imaging with no fixation of cells was conducted. Two different types of cancerous cells (i.e. colorectal HCT8 and breast KAIMRC1) were treated along with primary normal cells with IO-MMMs, Daun/Tam@IO-MMMs or equivalent concentrations of the respective free drugs. All the cells treated with control IO-MMMs appear healthy with clear blue Hoechst nuclei stains and no apoptotic features or death observed. In the drug-treated cells, however, the distribution of the red Daun fluorescence showed a pattern that varied for the different cells exposed to free Daun/Tam vs Daun/Tam@IO-MMMs. In Daun/Tam@IO-MMMs-treated cancerous cells, confocal images confirmed that Daun delivered by Daun/Tam@IO-MMMs is entering the cells gradually as time elapses causing apoptotic cell death after 24 h (FIG. 7A-7D). The intensity of red fluorescence increased progressively in cells with incubation time, resulting from the sustained drug release property of drug@IO-MMMs. While typical apoptotic features were evident for HCT8 and KAIMRC1 cells, the primary cells appeared to be healthy even after 24 h of treatment. Head-to-head comparison between the three cell lines treated with Daun/Tam@IO-MMMs after 24 h showed that Daun was translocated to the nucleus in cancerous cells, with more killing observed for HCT8 compared to KAIMRC1 cells, confirming the cell viability cytotoxicity results (FIG. 7A-7B). On the other hand, normal primary cells showed the least florescence intensities, where Daun was found to be mainly in the cytoplasm, with no prominent red nuclear staining or apoptotic features detected (FIG. 7C). Importantly, when incubating the same cell lines with free Daun/Tam at equivalent concentrations, the red fluorescence was found to be directly localized in the nucleus of all cells concurrently with minimal detectable presence in the cytoplasm, even after only 6 h of incubation.

Example 5

Cellular Internalization of IO-MMMs

Figure 7D:
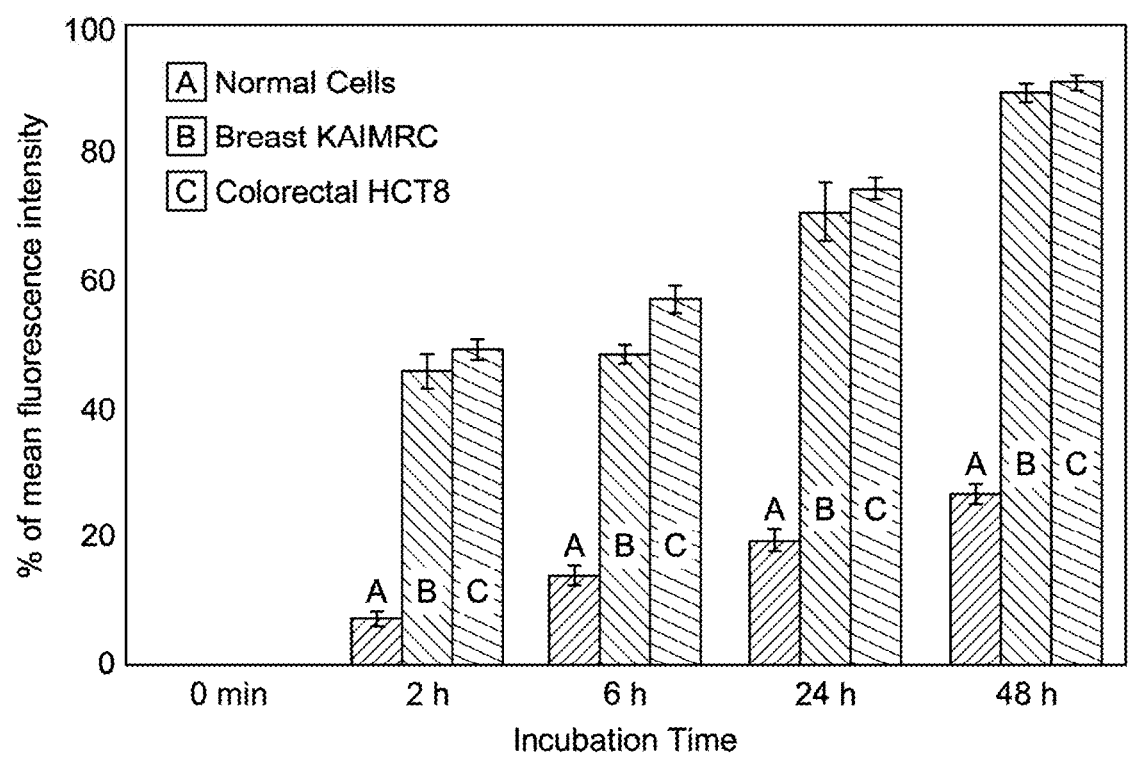
FIG. 7D shows the cellular uptake of IO-MMM as measured by flow cytometry after different incubation times.

Next, in order to gain insights into how the IO-MMMs interacted with the cells, their uptake with the different tested cell lines was examined by flow cytometry. Upon incubation of the cells with fluorescent-labeled IO-MMMs (10 μg/mL), all cell types showed significant cellular uptake gradually increasing with time, but slowly declining after 24 h (FIG. 7D). Interestingly, the fluorescence signals of cancerous cells demonstrated an uptake approximately 7-fold and 4-fold higher at 2 h and 24 h of incubation, respectively, compared to the primary normal cells with the least uptake. This confirmed and explained the confocal microscopy results obtained. These findings are consistent with the results of previous studies, reporting on the increased uptake of IONPs by human breast, leukemia and cervical cancer cells compared to normal cells. See El-Boubbou (2016); El-Boubbou (2017); Chaves, N. L. et al. Exploring cellular uptake of iron oxide nanoparticles associated with rhodium citrate in breast cancer cells. *Int. J. Nanomedicine* 12, 5511-5523 (2017); and Kohler, N., Sun, C. & Wang, J. & Zhang, M. Methotrexate-Modified Superparamagnetic Nanoparticles and Their Intracellular Uptake into Human. *Cancer Cells*. Langmuir 21, 8858-8864 (2005), each incorporated herein by reference in their entirety. While this may benefit from mechanistic studies, it is mostly attributed to differences in cell-membrane compositions, characteristics, morphologies, immunoprofiles, and metabolic activities between the tested cancerous and normal cells. See Chaves et al. (2017); Kohler et al. (2005); Kettler, K., Veltman, K., van de Meent, D., van Wezel, A. & Hendriks, A. J. Cellular uptake of nanoparticles as determined by particle properties, experimental conditions, and cell type. *Environ. Toxicol. Chem.* 33, 481-492 (2014); and Holliday, D. L. & Speirs, V. Choosing the right cell line for breast cancer research. *Breast Cancer Res.* 13, 215-215 (2011), each incorporated herein by reference in their entirety. The high metabolic activity of tumor cells along with the low metabolic activity of primary normal cells may contribute to the observed increase in IO-MMMs' uptake. Even when the normal primary cells were grown in a culture dish, they required much more time to become confluent with double the amounts of growth factors added.

Figure 8A:
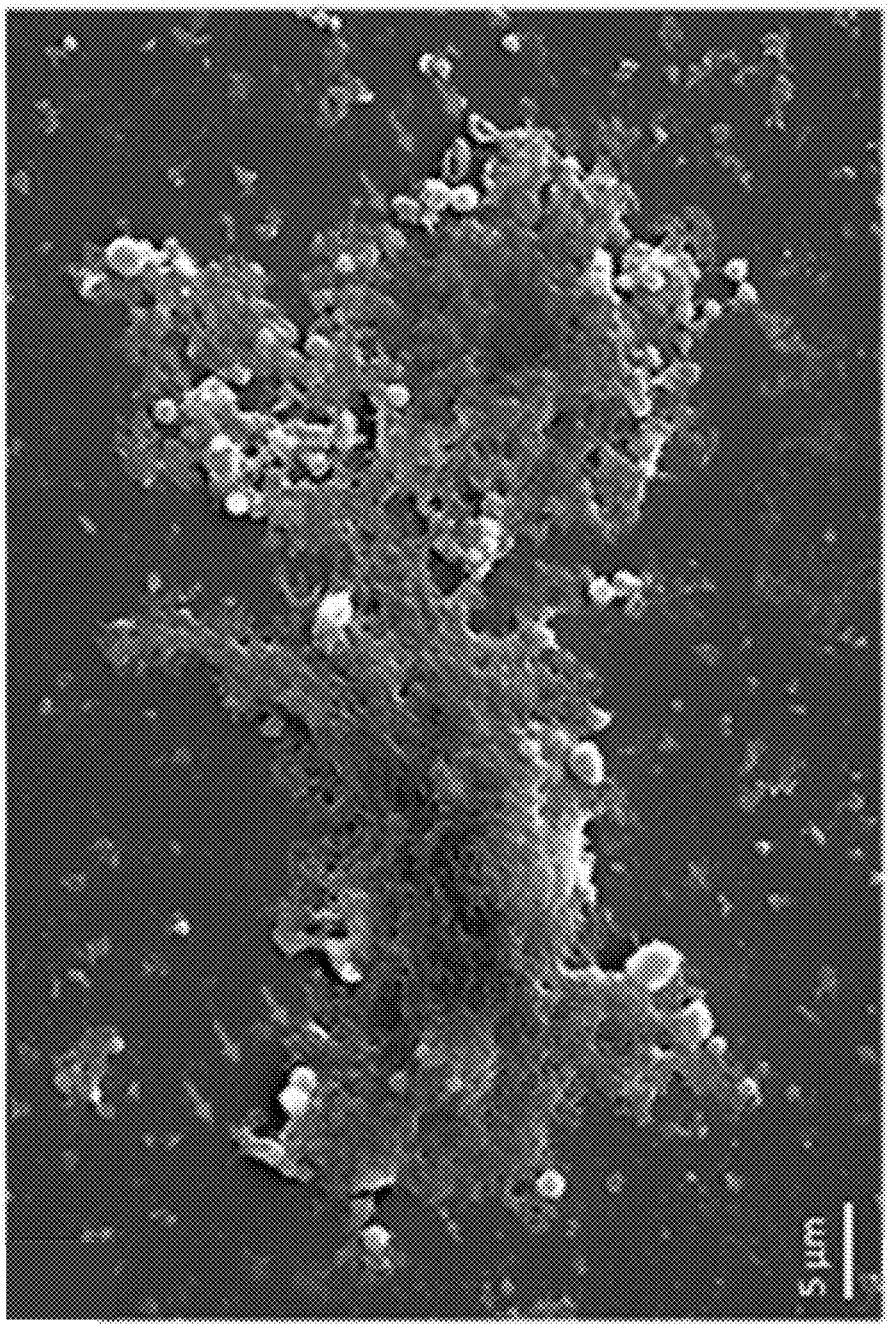
FIG. 8A is an SEM micrograph of colorectal cancer HCT8 cells after treatment with IO-MMMs, where arrows indicate some of the IO-MMMs.
Figure 8B:
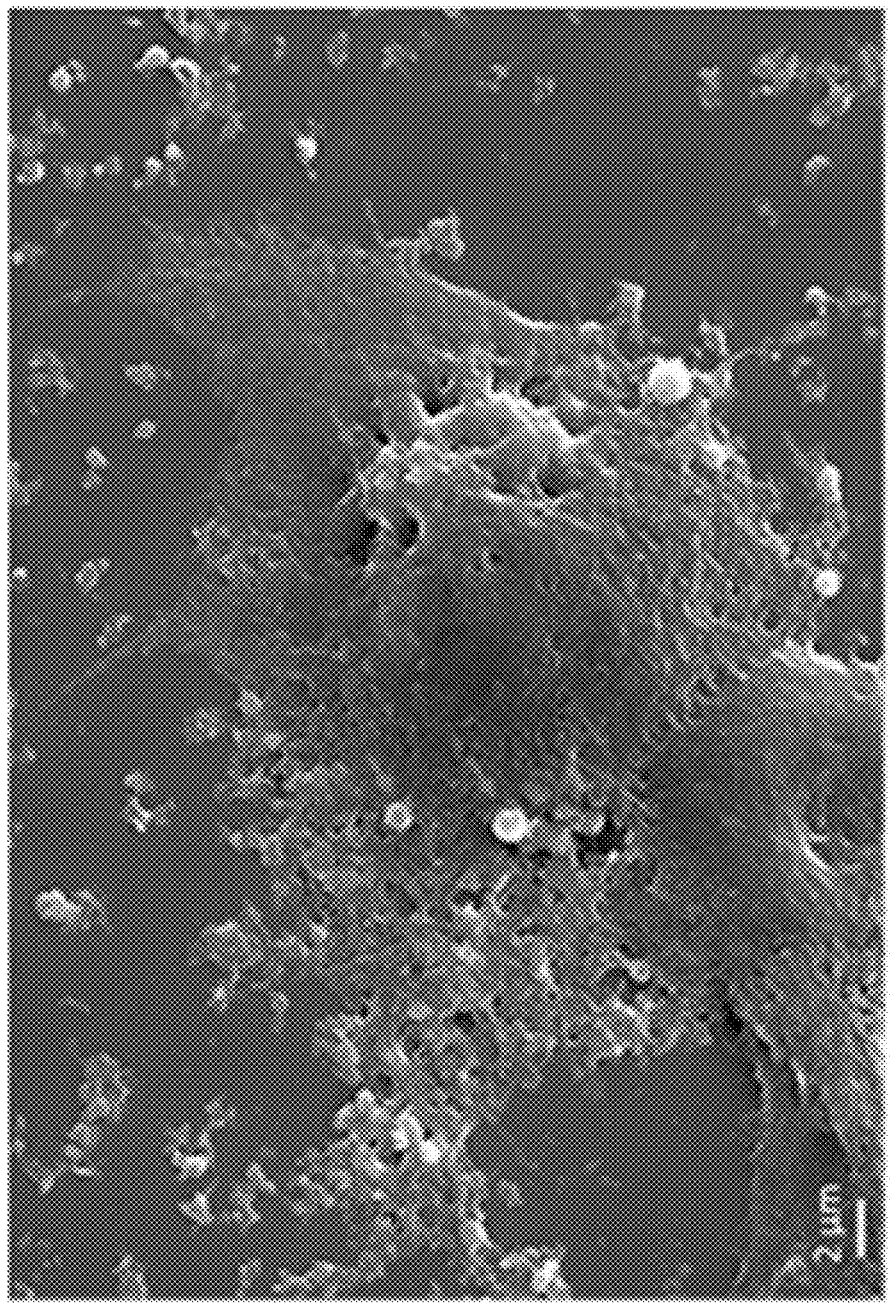
FIG. 8B is another SEM micrograph of colorectal cancer HCT8 cells after treatment with IO-MMMs.
Figure 8C:
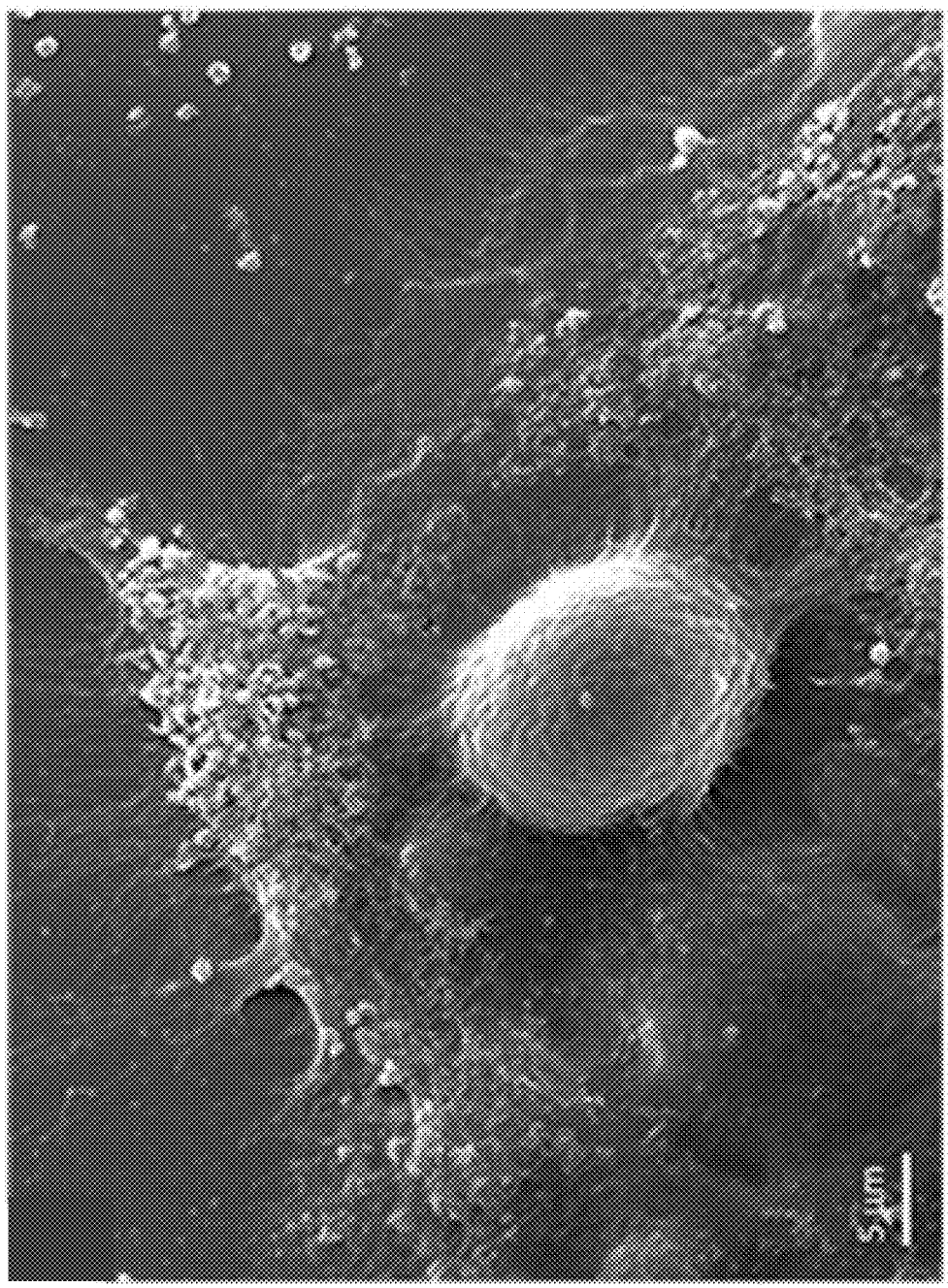
FIG. 8C is an SEM micrograph of breast cancer KAIMRC1 cells after treatment with IO-MMMs, where arrows indicate some of the IO-MMMs.
Figure 8D:
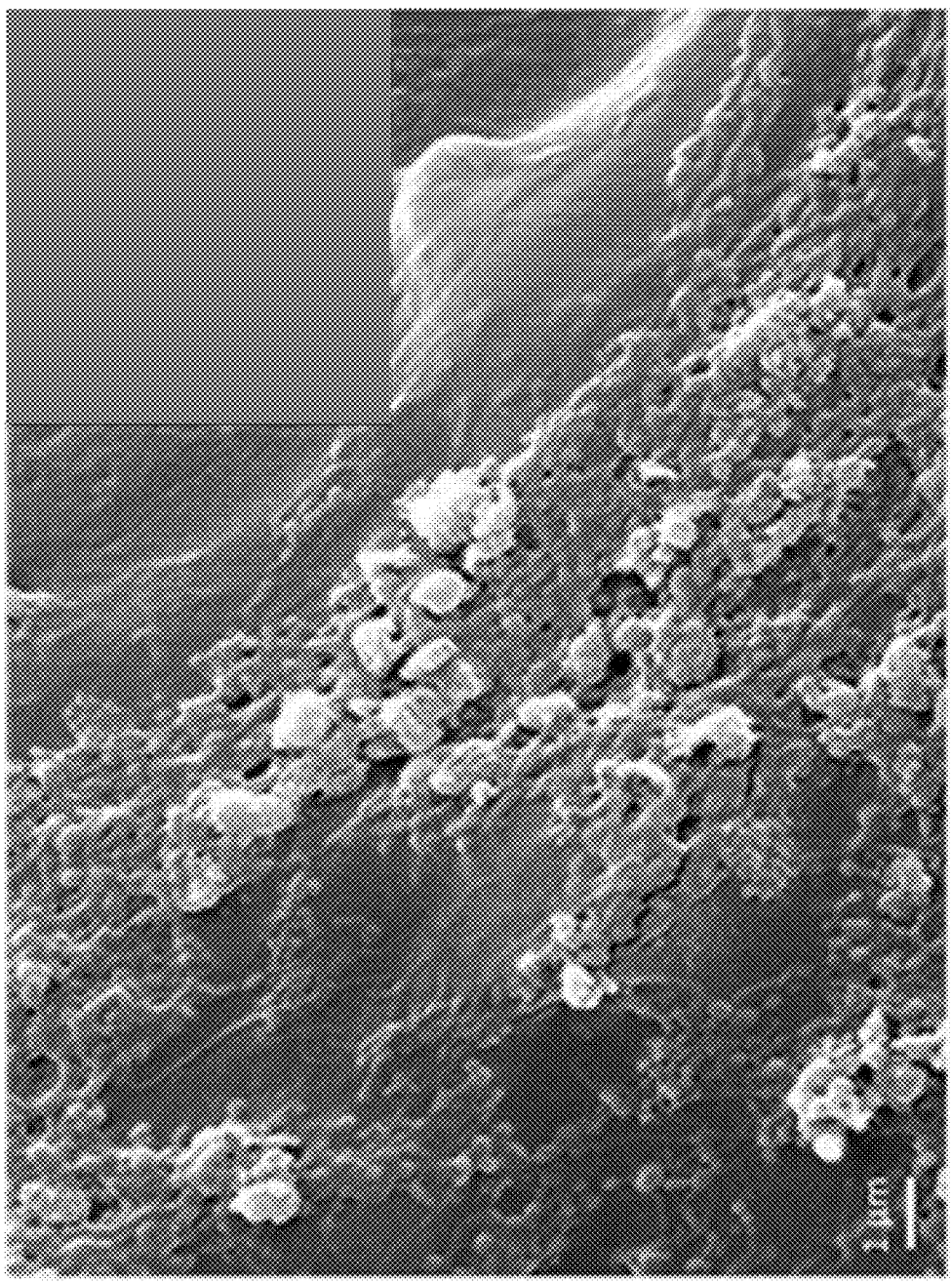
FIG. 8D is another SEM micrograph of breast cancer KAIMRC1 cells after treatment with IO-MMMs.
Figure 8E:
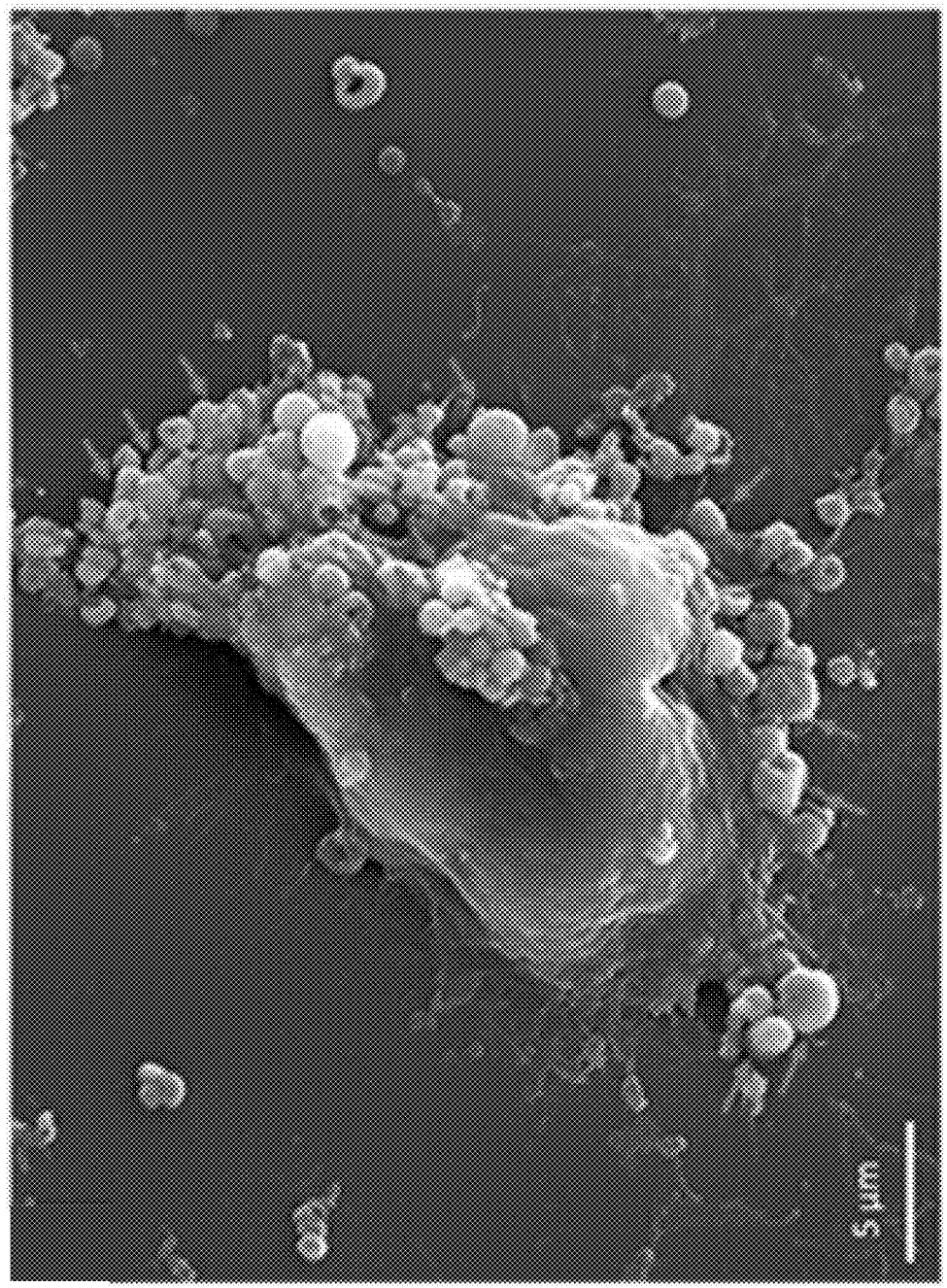
FIG. 8E is an SEM micrograph of breast cancer MCF7 cells after treatment with IO-MMMs, where arrows indicate some of the IO-MMMs.
Figure 8F:
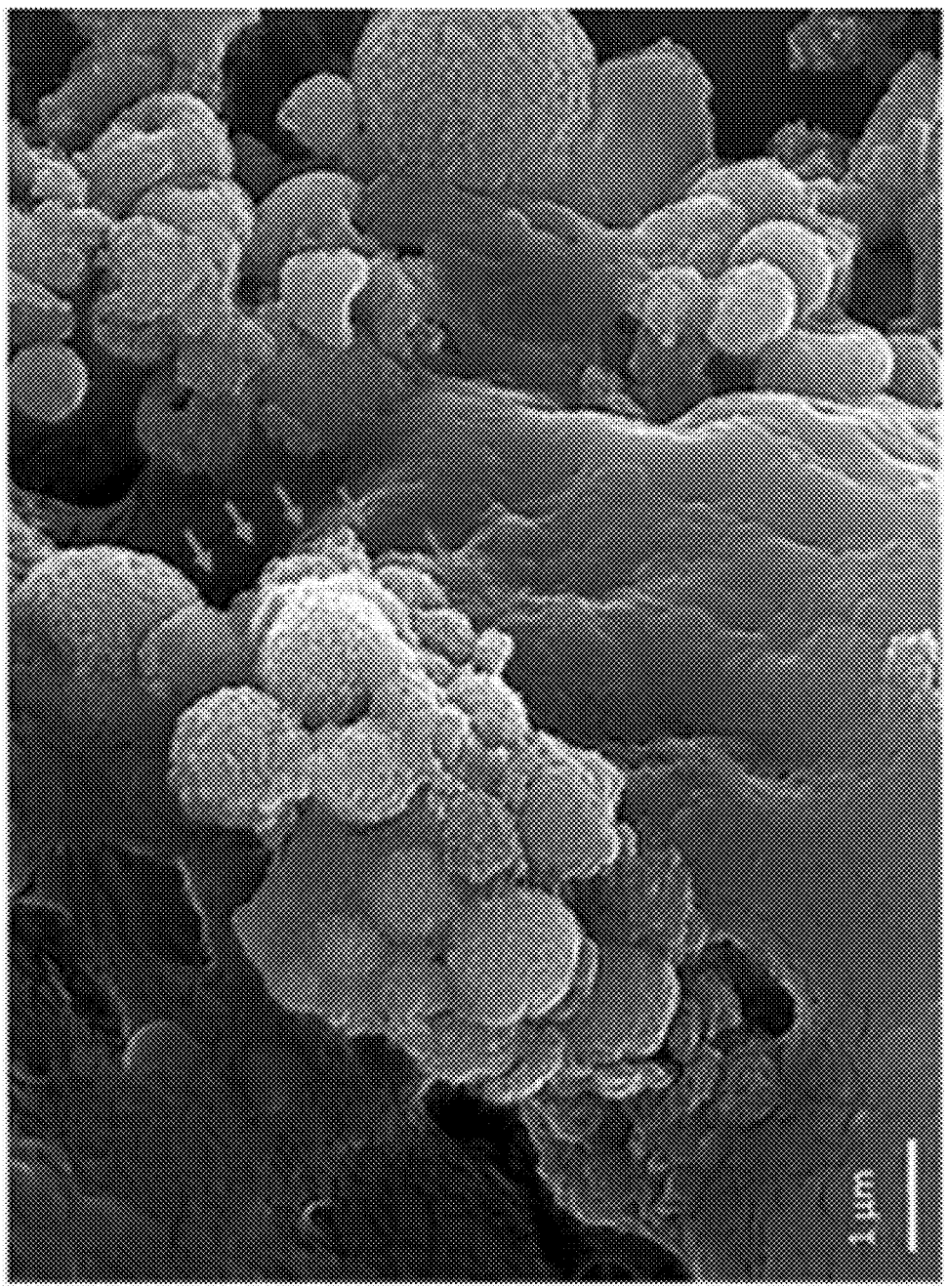
FIG. 8F is another SEM micrograph of breast cancer MCF7 cells after treatment with IO-MMMs.
Figure 8G:
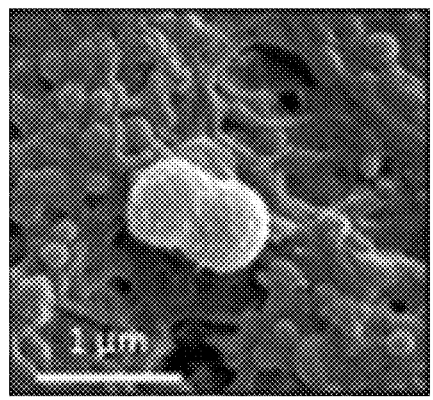
FIG. 8G is another SEM micrograph of breast cancer KAIMRC1 cells after treatment with IO-MMMs.
Figure 9A:
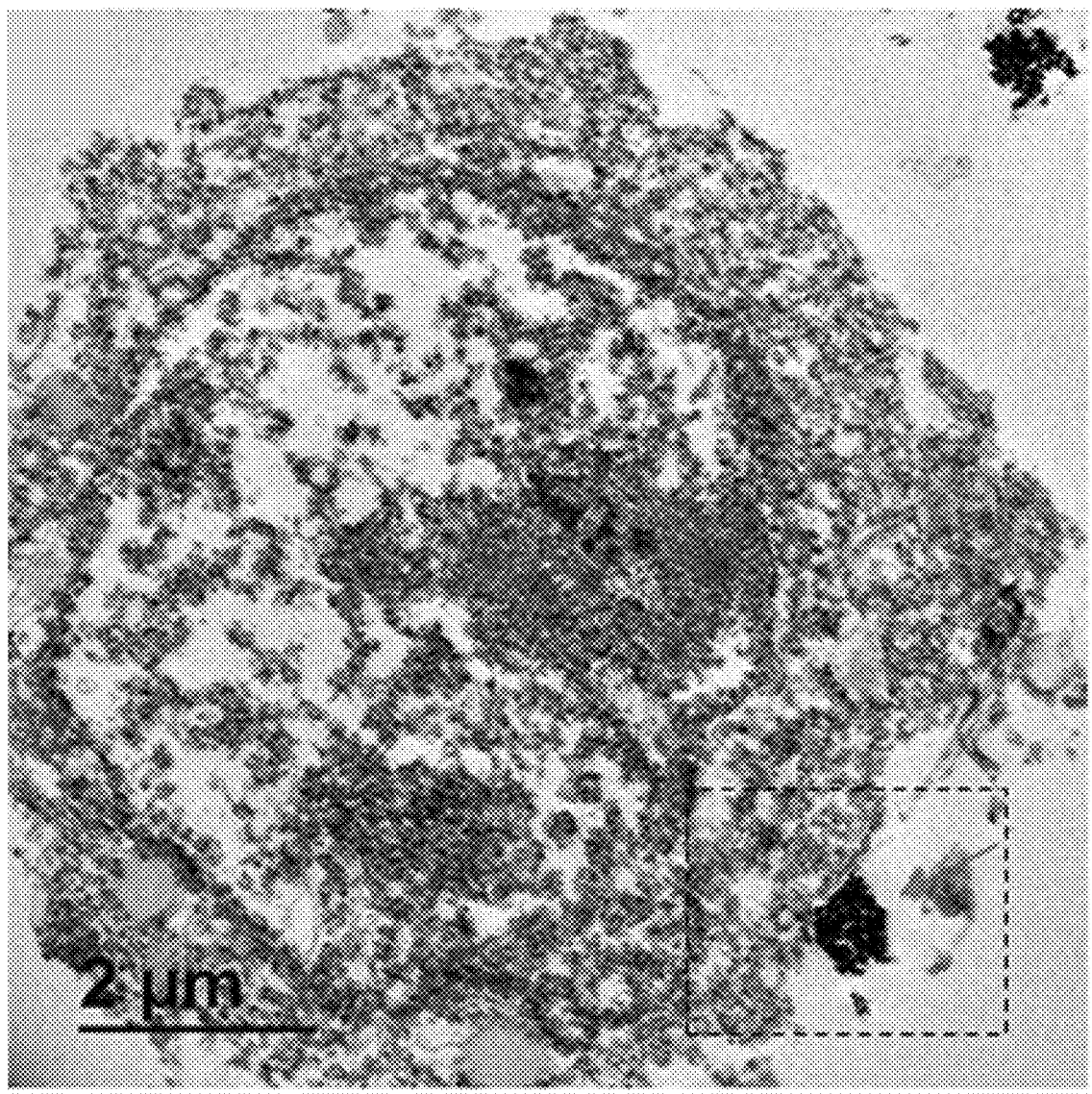
FIG. 9A is a TEM image of a representative cancer cell treated with IO-MMMs and showing attachment of the particles (at the arrows) to the plasma membrane.
Figure 9B:
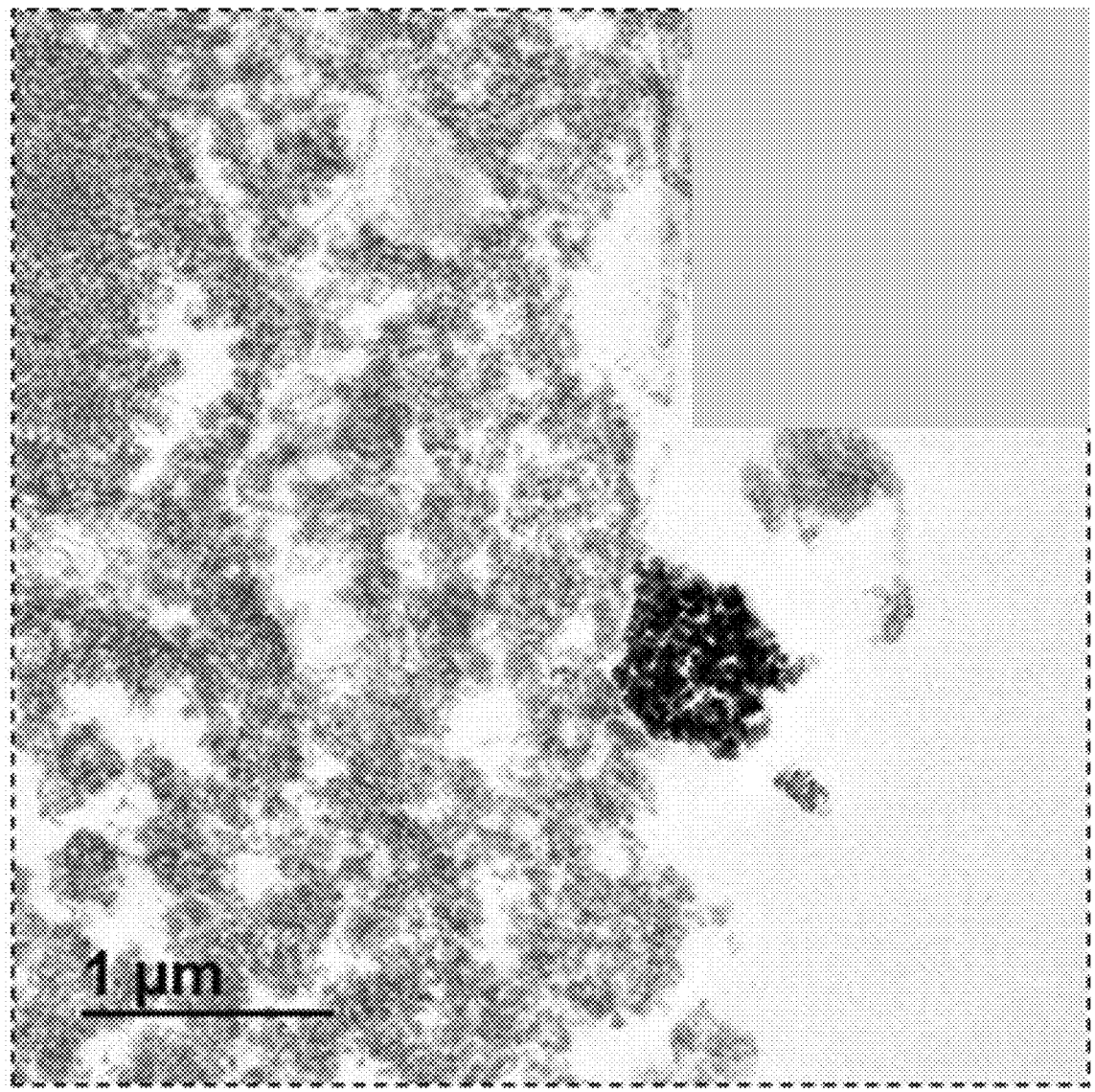
FIG. 9B is a zoomed in view of FIG. 9A.
Figure 9C:
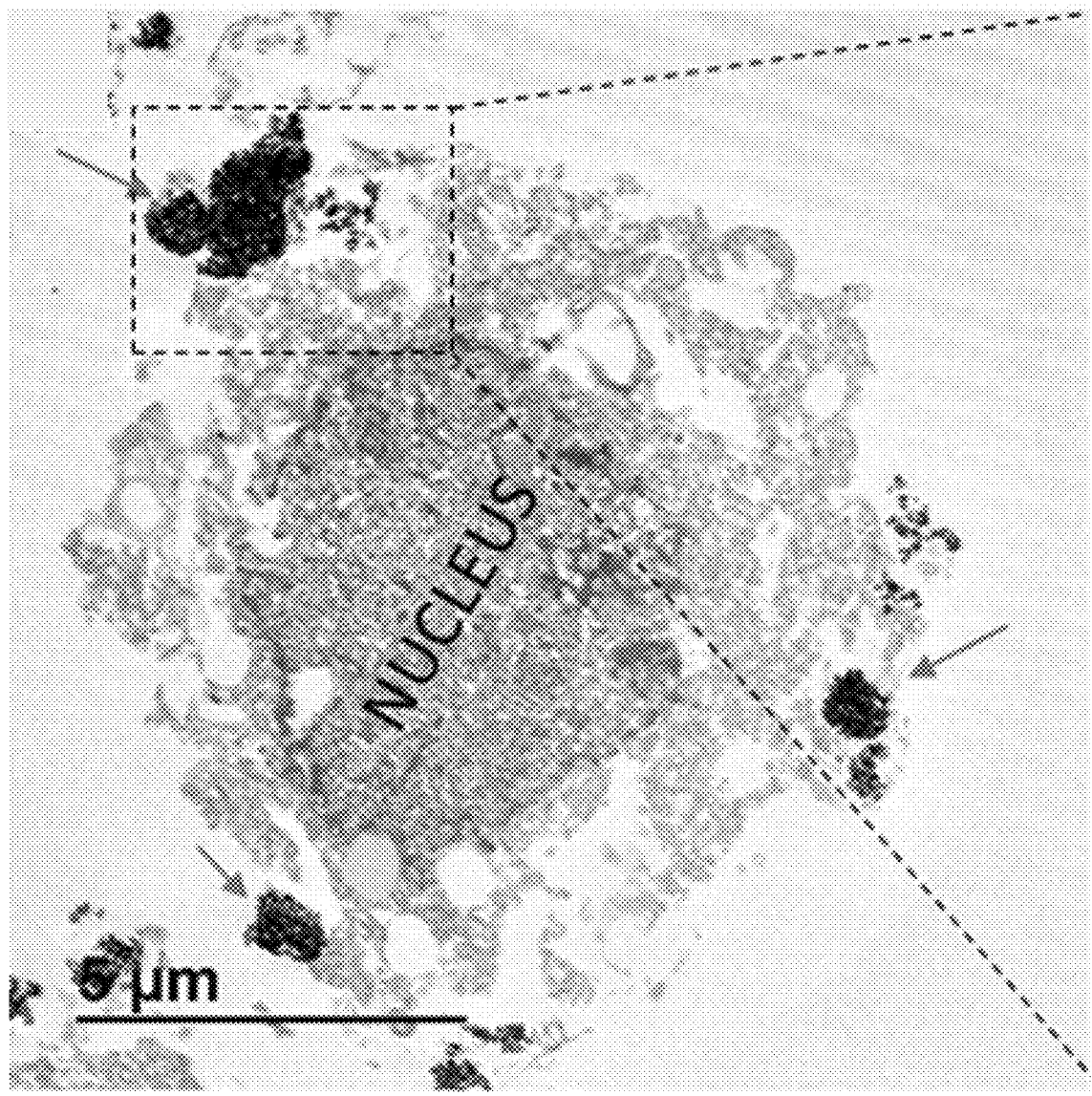
FIG. 9C is a TEM image of a representative cancer cell treated with IO-MMMs and showing internalization of the particles (at the arrows) inside the cytoplasm.
Figure 9D:
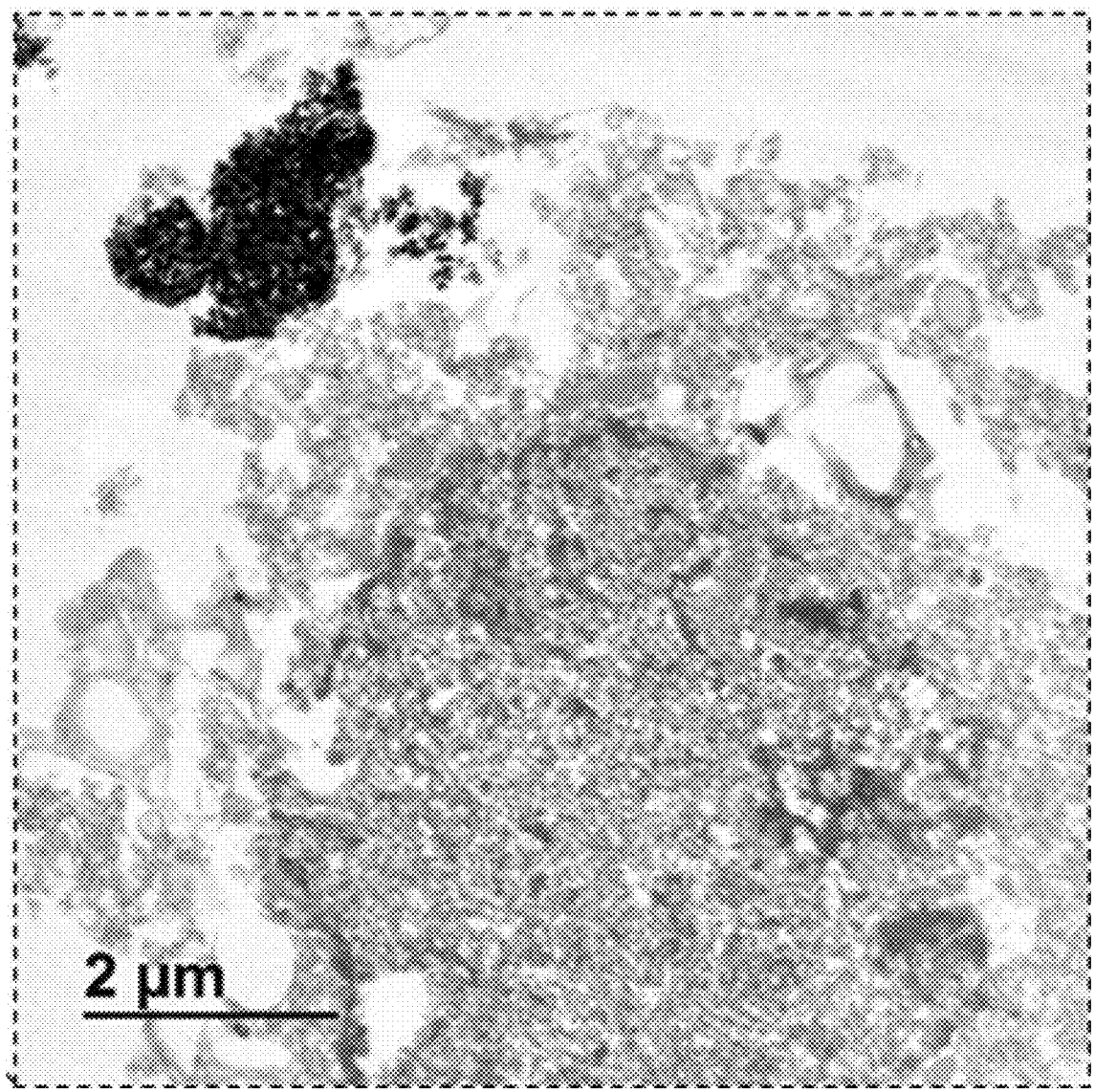
FIG. 9D is a zoomed in view of FIG. 9C.
Figure 9E:
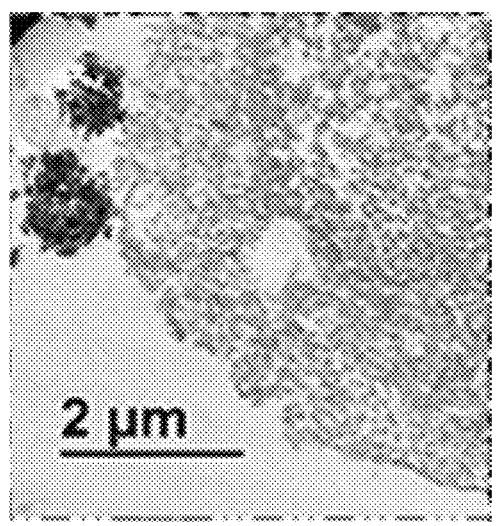
FIG. 9E is another TEM image of a representative cancer cell treated with IO-MMMs and showing attachment of the particles to the plasma membrane.

To further verify the uptake of the IO-MMM-treated cells at the sub-cellular level, the intracellular distribution was evaluated by electron microscopy imaging. SEM images indicate that the tested cells uptake the particles mainly found to be attached to the cellular membranes and consequently internalized inside (FIG. 8A-8B). Some IO-MMMs were found to be located on the periphery of the cells attached to their surfaces (FIG. 8C-8D, 8G). However, wrapping of the cellular membrane around the particles is evident (FIG. 8E-8F), proving that the IO-MMMs are cell-associated, interact with the plasma membrane, and are subsequently internalized in clusters. To validate the intracellular location, TEM imaging was also employed. After only 2 h of IO-MMM cell incubation, particles were seen interacting with plasma membrane, microvilli, and within cells (FIG. 9A-9E). Representative TEM micrographs show that the IO-MMMs are attached and then internalized, individually or in clusters, by the cells via the plasma membrane. Despite their relatively larger sizes, the particles were majorly seen internalized in the cytosol, but not in the nucleus, in agreement with previous reports. See Llinàs et al. (2018). The particles' engulfment took place without the particles being surface functionalized by polymeric or targeting groups, consistent with earlier reported works where particles up to 1,000 nm were found to be abundantly present in different areas of the cytoplasm. See Al-Salam, S. et al. In Vitro Study and Biocompatibility of Calcined Mesoporous Silica Microparticles in Mouse Lung. *Toxicol. Sci.* 122, 86-99 (2011); and Blumen, S. R. et al. Unique uptake of acid-prepared mesoporous spheres by lung epithelial and mesothelioma cells. *Am J Respir Cell Mol Biol* 36, 333-342 (2007), each incorporated herein by reference in their entirety. Commonly, cells uptake particles through one form of endocytic mechanisms, engulfed within the cell membrane, and contained intracellularly in membrane-bound vesicles which then traffic via endolysosomal pathways. See Bareford, L. M. & Swaan, P. W. Endocytic mechanisms for targeted drug delivery. *Advanced drug delivery reviews* 59, 748-758 (2007), incorporated herein by reference in its entirety. Studies have revealed that the particles' internalization, and their subsequent intracellular routing, is strongly dependent on their size, shape, composition, and surface properties, as well as on cell-specific parameters such as cell type, protein expression levels, or cell cycle phase. See Shang, L., Nienhaus, K. & Nienhaus, G. U. Engineered nanoparticles interacting with cells: size matters. *J. Nanobiotechnology* 12, 5-5 (2014); and Gratton, S. E. A. et al. The effect of particle design on cellular internalization pathways. *Proc. Natl. Acad. Sci. USA* 105, 11613-11618 (2008), each incorporated herein by reference in their entirety. The size-dependent interaction of different particles with the cell membrane is likely related to the membrane-wrapping process that initiates endocytosis, as has been observed here. It is generally accepted that larger particles (>500 nm) are predominantly taken up via non-specific energy-dependent membrane-tangled internalization and macropinocytosis. See Rejman, J., Oberle, V., Zuhorn, I. S. & Hoekstra, D. Size-dependent internalization of particles via the pathways of clathrin- and caveolae-mediated endocytosis. *Biochem. J.* 377, 159-169 (2004), incorporated herein by reference in its entirety. Moreover, the observed uptake may be possibly due to the high adsorption of phospholipid head groups on the plasma membranes to surface hydroxyl groups (Fe—OH) via a proven Fe—O—H—O—P mechanism. See Chaudhury, S., Varadachari, C. & Ghosh, K. Ab Initio Studies on Hematite Surface and the Adsorption of Phosphate. *J. Theor. Chem.* 2014, 7 (2014), incorporated herein by reference in its entirety. Thus it is believed that the internalization is to occur by a combination of mechanisms, most notably non-selective macropinocytosis, where internalization of upper-size-limit particles up to 3-µm was elegantly demonstrated. See Palm, W. Metabolic functions of macropinocytosis. *Philos Trans R Soc Lond B Biol Sci* 374, 20180285 (2019); and Gratton et al. (2008), each incorporated herein by reference in their entirety. After being uptaken, the particles subsequently traffic to lysosomes to be hydrolyzed and broken down. Interestingly, in some micrographs it was possible to observe agglomerates of iron oxide clusters closer to the nucleus, showing their traffic to acidic lysosomal compartments. It is worth noting that no major alternations in cellular structures or micro-organelles was apparent, confirming the biocompatibility of the utilized IO-MMM carriers. As compared to particles with smaller sizes (<200 nm), although the net internalization might be less, the actual drug release into the cytosol may well be higher, due to the prolonged residence time of the microparticles inside, thus avoiding rapid lysosomal degradation. See Rejman et al. (2004). Another important benefit, is that microparticles cannot passively diffuse into cells, enter organelles (i.e. mitochondria), and disrupt normal cell functions, which thus reduces potential toxic and systemic effects of smaller nanoparticles after administration. See Nel, A., Xia, T., Madler, L. & Li, N. Toxic Potential of Materials at the Nanolevel. *Science* 311, 622 (2006), incorporated herein by reference in its entirety. According to the references, this is the first report systematically studying the intracellular uptake of iron oxide mesostructures of sizes (>500 nm).

Collectively, all the results provide evidence that the major route of drug delivery is through differential uptake of drug@IO-MMMs into the cells, followed by sustained release of drugs intracellularly in a pH-dependent manner, causing apoptotic cell death. It is, thus, repeatedly evident that while free drugs are internalized by passive diffusion, the uptake of iron oxide nano/microparticles are rather directed by endocytic trafficking mechanisms. Regardless of the exact and complex intracellular routing, these results indicate that using the IO-MMM carriers described here is superiorly advantageous, as it reduces the unwanted diffusive side effects of the free drugs allowing selective synergistic anticancer drug delivery.

Example 6

Penetration of Drug@IO-MMMs into Tumor Tissue

In order to investigate the penetration of Daun/Tam@IO-MMM formulation into tumor tissues, primary breast tumor surgery sections derived directly from primary lesions were treated with either Daun/Tam@IO-MMMs or free Daun/Tam at equivalent drug concentrations. Due to inadequate drug accumulation, tumor drug resistance, and limited drug penetration of chemotherapeutic drugs to tumor tissues, it is imperative to design advanced delivery systems to enhance tumor accumulation, improve drug delivery, and, hence, enhance overall efficacies. See Saggar, J. K., Yu, M., Tan, Q. & Tannock, I. F. The Tumor Microenvironment and Strategies to Improve Drug Distribution. Front. Oncol. 3 (2013); and Danhier, F., Feron, O. & Préat, V. To exploit the tumor microenvironment: Passive and active tumor targeting of nanocarriers for anti-cancer drug delivery. *J. Control Release* 148, 135-146 (2010), each incorporated herein by reference in their entirety. While free drugs diffuse nonspecifically with typically limited penetration to interior of tumors, drug delivery carriers have tendencies to better accumulate in the tumor tissues via the acknowledged enhanced permeability and retention (EPR) effect and kill the cancer cells residing in the center, resulting in enhanced therapies. See Schroeder et al. (2012); El-Boubbou (2018); and Torchilin, V. Tumor delivery of macromolecular drugs based on the EPR effect. *Adv. Drug Deliv. Rev.* 63, 131-135 (2011), each incorporated herein by reference in their entirety. If anticancer drugs are unable to access and penetrate the cells within a tumor, then their therapeutic effectiveness will be hampered, no matter what is their actual potency. See Minchinton, A. I. & Tannock, I. F. Drug penetration in solid tumors. *Nat. Rev. Cancer* 6, 583-592 (2006), incorporated herein by reference in its entirety. Despite the existence of different strategies for stimuli-responsive triggered drug release systems (i.e. pH, redox, enzymes, heat, light etc.) intended to better penetrate tumors, many barriers still exist. See Mura et al. (2013); and Wilhelm, S. et al. Analysis of nanoparticle delivery to tumors. *Nat.* Rev. Mater. 1, 16014 (2016), each incorporated herein by reference in their entirety. In fact, the tumor penetration is a passive process that requires bio-stable particles of appropriate sizes (not too small nor too big) loaded with high capacities of drugs to allow extravasation of the particles across the hyper-permeable tumor vessels and effective diffusion through the tumor interstitial space. See Li, S.-D. & Huang, L. Pharmacokinetics and Biodistribution of Nanoparticles. *Mol. Pharmaceutics* 5, 496-504 (2008), incorporated herein by reference in its entirety. Primary tumor vessels have a defective cellular lining composed of disorganized, loosely connected, overlapping or sprouting endothelial cells where the gaps have been reported to range between 300 nm and 4700 nm. See Hashizume, H. et al. Openings between defective endothelial cells explain tumor vessel leakiness. *Am. J. Pathol.* 156, 1363-1380 (2000); and Sarin, H. et al. Physiologic upper limit of pore size in the blood-tumor barrier of malignant solid tumors. *J. Transl. Med.* 7, 51 (2009), each incorporated herein by reference in their entirety. This particularly contributes to tumor vessel leakiness and permits access of therapeutic vehicles. The challenge remains to deliver the particles throughout the tumor and its metastases given the heterogeneity of tumor microenvironment along with the limitations of spatial and temporal changes in the expression of the target. One of the most promising directions is, thus, to employ an internal pH-dependent sustainable delivery system that accumulates in the tumor and delivers drug-loaded particles into the target cells, releasing their loads intratumorally. Although nano-sized materials have been advocated for drug delivery to tumors, micron-sized particles such as Dox-loaded APMS have also shown promise in enhancing intracellular uptake of Dox and inhibiting tumor growth without any systemic toxicity both in vitro and in vivo. See Hillegass, J. M. et al. Increased efficacy of doxorubicin delivered in multifunctional microparticles for mesothelioma therapy. *Int. J. Cancer* 129, 233-244 (2011), incorporated herein by reference in its entirety. Therefore, and based on the promising in vitro cellular studies obtained, it was believed that the pH-triggered IO-MMM formulation designed here will attain the above-mentioned criteria.

Figure 10D:
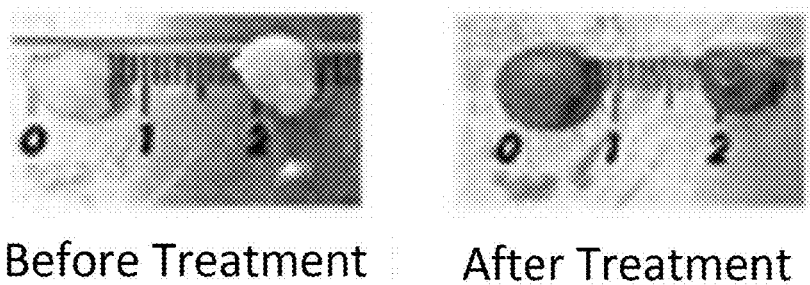
FIG. 10D is a photograph of tumor tissue before and after treatment with either Daun/Tam or Daun/Tam@IO-MMMs.

Dissected breast cancer tumor tissues were cut to ~1 mm$^3$ of equivalent sizes and were cultured to mimic oxygen, nutrient, and energy gradients similar to those found in vivo. The treatment was performed for 2 weeks at 37° C. and 5% $CO_2$. Z-stack confocal microscopy images starting from top to bottom of patient biopsy tissue sample exposed to Daun/Tam@IO-MMMs were acquired (FIG. 10A). As shown, extensive distribution of red Daun fluorescence through the tumor from top to bottom was observed (a middle selected slice of the z-stack images is displayed in FIG. 10B). 3D reconstructed images excitingly showed areas of extensive red fluorescence deep inside the tissue (~105 µm depth), signaling significant intracellular Daun release inside the tumor (FIG. 10C). It is believed that the particles penetrated inside the leaky vasculature of tumor tissue to a certain level, releasing the drugs internally. In comparison, the amount of red fluorescence penetration was noticeably much lower for the free drug. Thus, from the results, it is evident that the Daun/Tam@IO-MMM formulation penetrated deeper and delivered enhanced anticancer drugs into the tumor compared to the free diffusive drugs. Furthermore, optical photographs of tissue sections before and after treatment were also captured to register the shrinkage of tissue mass due to the different treatments (FIG. 10D). Even with the naked eye, the shrinkage of Daun/Tam@IO-MMMs-treated tumor tissue compared to free drug-treated tissue was evident, confirming the potential of IO-MMMs as effective drug delivery vehicles penetrating inside the tumor via the EPR effect, and significantly improving the recognized limited tumor penetration of free drugs. It is to be noted that similar tumor tissues were also treated with either Daun@IO-MMMs or Dox@IO-MMMs alone, however, lower therapeutic effects were observed, signifying that the co-delivery of Daun and Tam together synergistically exert their anti-cancer functions to achieve a better outcome. This designed multi-drug IO-MMM formulation is, thus, promising to enhance the effectiveness of the therapeutic drugs with advantageous doses, opening new opportunities for in vivo combined therapeutics. This combinatory drug therapy depicts the synergistic enhanced antitumor effects where lower doses of each therapeutic drug can be used, which in turn will have a dramatic effect in cancer treatments, reducing the typical toxicity towards the healthy cells. Furthermore, magnetic guidance on this system is potentially feasible by focusing an external magnetic field on the target after injection of IO-MMMs.

Unique bio-stable iron oxide mesoconstructs with remarkably high surface areas and pore volumes were prepared by hard-templated methodology using APMS as the silica template. The as-prepared IO-MMM mesostructures can be loaded with hydrophilic and hydrophobic therapeutic anticancer drugs, or a combination of both drugs, on demand. The combinatory drug@IO-MMM formulation demonstrated cellular uptake and pH-dependent drug release with enhanced cytotoxic effects towards different types of cancerous cells. Particularly, Daun/Tam@IO-MMMs were found to be highly potent to the different metastatic breast and colorectal cancer cells, with considerably less toxicity towards the normal primary cells, showing potential as selective anti-cancer agents for cancer therapeutics. Importantly, this drug-loaded IO-MMM formulation was also able to effectively accumulate in patient primary tumor tissues, delivering the cytotoxic drugs and killing the tumor cells inside. The Daun/Tam@IO-MMM vehicle described herein facilitates packing of chemo/hormonal therapeutic anticancer drugs without premature release at physiological pH, recognizes the target cells, and finally releases the drugs at the intracellular site of tumor cells to induce apoptosis and shrinkage. Notably, this combinatory mesoporous drug@IO-MMM platform displays not only a pH-dependent but potentially a magneto-responsive drug release behavior, opening new opportunities for in vivo imaging, cancer monitoring, and theranostics.

Example 7

Materials and Methods

Unless otherwise indicated, all chemicals and solvents were obtained from commercial suppliers and used as received without further purification. Iron (III) chloride hexahydrate ($FeCl_3.6H_2O$), zinc metal powder, magnesium powder, cetyltrimethylammonium bromide (CTAB), tetraethyl orthosilicate (TEOS),3-aminopropyltriethoxysilane (APTES), sodium fluoride (NaF), concentrated HCl, ammonium hydroxide ($NH_4OH$), iron (II) chloride tetrahydrate ($FeCl_2.4H_2O$), polyacrylic acid (PAA), fluorescein isothiocyanate (FITC) as well as the drugs Doxorubicin (Dox), Daunorubicin (Daun), and Tamoxifen (Tam) were all purchased from UFC Biotechnology. Dulbecco's Phosphate Buffered Saline (DPBS), Phosphate Buffered Saline (PBS), Advanced Dulbecco's Modified Eagle Medium (DMEM), Phenol-red free DMEM, Fetal Bovine Serum (FBS), Hoechst 33342 stain, L-Glutamine, and Penicillin-Streptomycin (Pen-Strep) were all purchased from Invitrogen. MTT (Thiazolyl Blue Tetrazolium Bromide) powder was purchased from Bioworld, USA. All cell lines were purchased from the American Type Culture Collection (ATCC) and grown in Advanced DMEM supplemented with 10% FBS and 1% Penicillin/Streptomycin. Human cancerous cells used in this study are: MCF7 (Michigan Cancer Foundation-7 metastatic breast cancer cell line isolated from a 69-year-old Caucasian woman); HCT-8 (Human ileocecal colorectal adenocarcinoma cell line isolated from a 67-year-old male); KAIMRC1 (naturally immortalized breast cancer cells isolated from a 62-year-old Arab female suffering from stage JIB breast cancer); along with primary normal fibroblast-like cells (isolated from a breast cancer patient after surgical procedure) used as a control. Cells were cultured for at least 24 h before conducting the experiments. All experiments were conducted in triplicates and mean averages were plotted. Tumor surgical sections were collected after examination by a certified pathologist, prepared for analysis on the same day, and cultured in advanced DMEM. Tissues were collected at the time of surgery after written informed consent was obtained from patients at King Abdulaziz Medical City, National Guard Hospital, under approval from KAIMRC Institutional Review Board (IRB). The tissue biopsies were surgical remnants which were consequently used in this study. All methods were performed in accordance with standard guidelines and regulations, and the procedures of tissue experiments were approved by Bioethics Department, IRB, KAIMRC (RC16/096).

Example 8

Characterization

SEM images were processed using a FEI NanoSEM 450® scanning electron microscope at 15 kV. EDX were acquired using same system which is supplied with EDAX® AMETEK® (material analysis division). TEM images were collected on a JEOL-JEM 1400 operating at 120 kV using a Gatan® camera with Digital Micrograph Imaging software. Samples were prepared by depositing 1 µL of the nanoparticles dispersed onto 400 mesh Formvar/Carbon-supported copper grid. X-ray diffraction (XRD) patterns were recorded using Bruker D8 Diffractometer® using Cu Kα radiation operated at 40 kV and 20 scan range from 20° to 70°. FTIR spectra (400-4000 $cm^{-1}$) were recorded as KBr pellets using Shimadzu IRAffinity-1®. DLS and zeta potential measurements were assessed on Malvern Zetasizer® Nano ZS instrument. Calcinations were carried out either under flowing air or under argon. The following heating profile was used for APMS calcination: 2° C./min ramp to 450° C., 240 min hold at 450° C., 10° C./min ramp to 550° C., 480 min hold at 550° C. Confocal images were visualized using inverted Zeiss LSM 780® multiphoton laser scanning confocal microscope equipped with 20× and 40× (oil immersion) objectives and Axiocam® cameras. Z-stack images of tissue sections were acquired using above mentioned Zeiss LSM780® microscope.

Example 9

Preparation of APMS

APMS was synthesized following previous work where TEOS was used as the silica source and CTAB as the structure directing agent. Briefly, CTAB (0.7 g), $H_2O$ (15 mL), ethanol (5 mL), and concentrated HCl (1.7 mL) were vigorously stirred until the surfactant was dissolved. TEOS (1.4 mL) was then slowly added while stirring. After 5 min, NaF (0.5 M in water, 1.85 mL) was added and stirring was continued until the mixture turned turbid. The mixture was then quickly transferred to a Teflon bottle and heated at 100° C. for 60 mins. The resulting APMS precipitate was cooled to room temperature, collected by vacuum filtration, repeatedly washed with water and ethanol, and dried under vacuum. Calcination at 550° C. under air to remove the CTAB surfactant afforded calcined APMS ready for iron impregnation.

Example 10

Preparation of IO-MMMs

IO-MMMs were prepared following modified literature procedures using calcined APMS as the hard template. See Lu et al. (2010); and Shen et al. (2015). 0.175 g of APMS was dispersed in 10 mL of 0.5 M aqueous solution of $FeCl_3.6H_2O$. Trace amounts (0.001-1%) of zinc (or magnesium) were then added and the reaction mixture was aged for 24 h under constant stirring at room temperature. The resulting material was carefully decanted to separate the reducing agent, purified by successive centrifugation and repeated washing with water and ethanol, and finally dried under vacuum. This impregnation process was then repeated with 0.5 M of $FeCl_3$ aqueous solution to ensure complete iron impregnation. The obtained product was then heated to 350° C. at 2° C./min for 3 h under argon atmosphere and left at this temperature for 4 h. Thermal treatment at 350° C. under inert atmosphere is adequate to completely decompose and convert iron species to $\gamma$-$Fe_2O_3$ nanocrystals, without formation of other phases. Finally, the sample was treated several times with hot 5 M NaOH solution to completely remove the APMS silica template, purified by centrifugation, washed with water and ethanol, and then dried in an oven at 100° C. IO-MMMs were dispersed in water for cellular studies. It is worth noting that different $FeCl_3$ aqueous solutions (0.25, 0.5, 0.75, and 1 M) for impregnation were tested. No much difference was observed when greater than 0.5 M solutions were used. This experimental procedure can be extended to a wider range of binary transition metal oxides by simply using a wide range of the commercially available cheap metal salt precursors.

Example 11

Preparation of IO-MMMs

First, PAA-MNPs were prepared according to a previous report. See El-Boubbou et al. (2016). In a generalized procedure, 5 mL aqueous solution of $FeCl_3.6H_2O$ (0.10 g) and PAA (0.10 g) were mixed and magnetically stirred under argon in a degassed vial for 15 min. Aqueous solution of $FeCl_2.4H_2O$ (0.05 g) was then injected. After stirring for a few minutes, 1 mL of ammonium hydroxide (30%) was slowly added, and the mixture was heated to 80° C. and vigorously stirred for 90 min. The black precipitate of PAA-MNPs formed was cooled to room temperature by removing the heat source, isolated via centrifugation (4500 rpm, 10 min), washed repeatedly with water, isopropanol, and ethanol, and finally redispersed in water. Centrifugation (4500 rpm, 20 min) was then applied to remove any undispersed residue. The stable colloidal PAA-MNPs solution was stored at ambient conditions for several months. No precipitation over the course of months was observed. It is to be noted that when hexylamine (0.5 mL) was added in the synthesis, PAA-MNPs clump and precipitate, and the particles were found to be dispersible in ethanol. 0.10 g of as-prepared calcined APMS was then impregnated/wetted with aqueous or ethanolic solution of PAA-MNPs (0.1 to 2 mg/mL) and the reaction mixture was stirred for 24 h at room temperature. The resulting material was then centrifuged, washed repeatedly with water and ethanol, dried under vacuum, and thermally treated as before. Etching using hot 5 M NaOH solution afforded very low yields of IO-MMNs instead, with low BET surface areas and pore volumes. Even when repeated impregnation was performed, not much of a change in the final product was observed.

Example 12

Magnetic Manipulation of IO-MMM Magnetized Cells

Prior to the experiment, cells were seeded on 35 mm Ibidi® dishes for 24 h at 37 C and 5% $CO_2$. Cells were then treated with IO-MMMs for 1 h, washed with PBS, stained with HOECHST 33342 nuclear stain, and imaged using EVOS FL Auto Imaging System® in the presence or absence of a permanent magnet. Both transmitted light and blue fluorescence images were acquired. Optical camera photos were also shot recording the aggregation of cells in the presence of the magnet.

Example 13

Drug Loading 1 mL aqueous dispersion of IO-MMMs (1.0 mg/mL) and aqueous drug solutions (250 µg/mL) were gently shaken on a rotary shaker for 36 h to enable maximal drug loading. The particle dispersions were then isolated via centrifugation (4500 rpm, 10 min), washed repeatedly with water until no drug was detected in the supernatant by UV-vis, and finally redispersed in water to form stable aqueous dispersions of drug@IO-MMMs. In case of Tam and Daun loading, Tam was first loaded followed by Daun to afford Daun/Tam@IO-MMMs (165 µg/mL Tam; 235 µg/mL Daun). Loading efficiencies were determined by UV-Vis spectroscopy as depicted below. The absorbance of the residual drug in the supernatant was measured $\lambda_{max}$=490 nm for Dox and Daun; $\lambda_{max}$=290 nm for Tam) and the percentage of drug loading (w/w %) was then quantified. The loading efficiency was calculated as:

Loading Efficiency=$(W_1/W_0)\times 100$, where $W_1$ is the amount of drug loaded onto the particles, and $W_0$ is the amount of drug in the initial solution. The amount of drug loaded onto IO-MMMs was calculated from the difference between the initial drug concentration and the drug concentration left in the supernatant.

Example 14

Drug Release

In a typical study, 5 mg of drug@IO-MMMs were suspended in 1 mL PBS buffer at two different pH values (pH=7.4 and pH=4.5) and gently rotated at 37° C. in an oven provided with a precise control in the temperature within 0.01° C. The concentration of drugs in the supernatant was determined at fixed time intervals by UV-vis spectroscopy. At specific time points, supernatant aliquots obtained by centrifugation were taken from each tube, measured and returned to their respective tubes after UV-vis measurements. The drug concentration could be directly calculated from the measured absorbance. Triplicate aliquots were run for each time interval, and average values plotted. The percent drug release was calculated using the equation below:

% Drug Release=$(Abs_{(t)}$ of released drug/$Abs_{(t0)})\times 100$.

Example 15

Cell Viability Assays

All cell lines were seeded in a 96-well plate at a density of $5\times 10^4$ cells/well and incubated at 95%/5% humidified air/$CO_2$ and 37° C. Post 24 h, the media was removed and fresh phenol-red free DMEM containing 0.5% FBS was added to the cells. Cells were then treated with various concentrations of IO-MMMs, drugs@IO-MMMs, and respective free drugs in 200 µL supplemented DMEM. The wells at all edges were left free of cells in order to prevent edge effect. An additional row with only the particles was added in order to account for the particle effect. After 48 h of incubation, the media was removed and the cells were washed with PBS. Cell viability was then determined using the MTT viability assay following the manufacturer's protocol. Briefly, 20 µL, of MTT reagent (5 mg/mL) was added to each well and kept for 4 h at 37° C. in the incubator. The supernatant was then removed, and the MTT formazan were dissolved in 100 µL dimethyl sulfoxide (DMSO). The absorbance was measured on Molecular Devices SpectraMax® microplate absorbance reader at 570 nm. The percentage of viable cells was calculated as the ratio of the absorbance of the treated group, divided by the absorbance of the control group, multiplied by 100. The absorbance from the untreated control cells was set as 100% viable.

Example 16

Live Confocal Microscopy Imaging

Cells were incubated in 8-well dish ((iBidi, Germany) for 24 h prior to particle exposure. After removing the supernatant, cells were then exposed to IO-MMMs (10 µg/mL), Daun/Tam@IO-MMMs (10 µg/mL NPs; 2.50 µg/mL Daun; 1.75 µg/mL Tam), or equivalent concentration of free Daun/Tam. The cells were incubated for different periods of time (i.e. 6 and 24 h). Hoechst 33342 stain was then added. The cells were allowed to settle down for 20 min before microscopic visualization. To mimic physiological conditions, no fixation of cells was conducted.

Example 17

Fluorescence Activated Cell Sorting (FACS)

Cancerous and normal cells (1×10$^5$ cells per well) were seeded in 12 well culture dishes, incubated for 24 h, and then treated for different periods of time with FITC-labeled IO-MMMs (10 µg/mL) prepared following literature procedure. See Li, Z. et al. Biomimetic nanoassembly for targeted antigen delivery and enhanced Th1-type immune response. *Chem. Commun.* 51, 15975-15978 (2015), incorporated herein by reference in its entirety. Both live and dead cells were collected, pelleted, washed with PBS, and then transferred to FACS tubes for analysis. Flow cytometry measurements were then assessed. Triplicate experiments were conducted. Mean values were plotted and error bars represents standard deviations.

Example 18

Scanning Electron Microscopy of Cell Specimens

Cells were treated with IO-MMMs (10 µg/mL) for 6 h prior to fixation. The specimens were then processed for SEM by the following method: Cells were first fixed with 4% paraformaldehyde at 4° C. for 30 min and then dehydrated with graded concentrations of ethanol. The cells were then transferred to appropriate carbon taped stubs (Ted Pella, USA) for imaging. To enhance the electron conductivity, samples were coated with gold/palladium (Au/Pd) by sputter coating and examined on a FEI NanoSEM 450 scanning electron microscope at 15 kV.

Example 19

Transmission Electron Microscopy of Cell Specimens

Cells were first treated with the IO-MMMs for 2 h as described above. The specimens were then processed for TEM by the following method: the specimen was fixed in 4% glutaraldehyde in 0.1 M PBS (pH 7.4) for 1 h. After washing in the same buffer, the sample was post-fixed in 1% OsO$_4$ in 0.1 M PBS (pH 7.4) for 1 h, followed by PBS washing. The specimen was then dehydrated in a series of acetone solutions and infiltrated in acetone: resin (1:1) for 1 h, and then with acetone: resin (1:2) for more than 3 h. The specimen was then embedded in epoxy resin (Araldite®) and placed in an oven at 80° C. overnight to polymerize. Ultrathin sections were obtained with Ultramicrotome (RMS), mounted on copper grids, and stained for contrast with heavy metal stains (uranyl acetate and lead citrate). TEM images were then collected on a JEOL-JEM 1200® operating at 120 kV using Gatan® camera with Digital Micrograph Imaging software.

Example 20

Surgical Tissue Processing

Human breast cancer patient tissue resections were placed in a sterile conical tube containing PBS on wet ice during transportation from the operating room to the research laboratory. Resections were transported to the laboratory within 30 min of clinical sample collection. Upon arrival, the tissue resections were examined by a certified pathologist. Resections were then manually minced using a sterile scalpel and washed thoroughly with PBS. Then small tumor pieces were transferred into 8-well µ-dishes (Ibidi, Germany) containing advanced DMEM supplemented with 10% FBS, 1% L-glutamine, and 1% antibiotics (Pen-Strep). Tumor tissue sections were treated with the different drug@IO-MMMs or equivalent concentration of free drugs for 7 days prior to imaging with an inverted Zeiss LSM 780® multiphoton laser scanning confocal microscope equipped with 20× and 40× (oil immersion) objectives and Axiocam® cameras.

Iron oxide mesoporous magnetic microparticles (IO-MMMs) were prepared by a modified reverse hard-templating approach using acid-prepared mesoporous spheres (APMS) as the hard silica template. The obtained mesostructures exhibited remarkably high surface area and large pore volumes ($S_{BET}$=240 m$^2$/g and $V_{pore}$=0.55 cm$^3$/g), controllable average sizes, generally uniform morphologies, and excellent biocompatibilities, allowing them to achieve effective drug release in cancer cells and tumor tissues. IO-MMM carriers were able to co-load high amounts of hydrophilic chemotherapeutic drugs (Dox or Daun) and/or hydrophobic hormonal anticancer drugs (Tam), and release them sustainably in a pH-dependent manner, utilizing the fluorescence of Daun to real-time trace the intracellular drug distribution, and employing Daun/Tam to treat cancer by combined chemo/hormonal therapy. Cytotoxicity assays against different types of cancerous cells showed that the combinatory Daun/Tam@IO-MMM formulation significantly reduced the viability of metastatic MCF7 and KAIMRC1 breast as well as HCT8 colorectal cancer cells, with the least potency towards non-cancerous normal primary cells (up to 10-fold). Electron, flow, and live confocal microscopy imaging confirmed that the loaded vehicles were successfully and differentially uptaken by the different tested cells, gradually releasing their payloads, and causing apoptotic cell death. Importantly, compared to free drugs, Daun/Tam@IO-MMMs displayed enhanced drug accumulation in patient breast primary tumor tissues, deeply penetrating into the tumor region and killing the tumor cells inside. The designed carriers described here thus constitute a magnetic mesoporous smart system that entraps different kinds of drugs and releases them in a controlled manner for combinatorial chemo/hormonal cancer theranostics. This multifactorial platform provides an efficient synergistic antitumor system that overcomes limitations of conventional cancer therapy.

As a proof-of-concept, anticancer chemo/hormonal therapeutic drugs of various hydrophilicities were loaded into the IO-MMMs and systematically tested against different types of human cancerous cells and patient tumor tissues. Loading and release results show that high loading efficiencies were achieved with drug release rates dramatically improved at low acidic cellular pH, but not at neutral physiological pH. The cytotoxic effects of IO-MMMs and drug@IO-MMMs were then evaluated in different types of breast and colorectal cancer cells as well as normal primary cells. The fluorescence of drugs was monitored by live confocal imaging to demonstrate subcellular internalization and pH-driven drug release of drug@IO-MMMs inside the cells. Moreover, electron microscopy was employed to further assess the uptake of the IO-MMMs-treated cellular samples. Importantly, when tested with primary breast tumor surgery sections derived directly from patient primary lesions, enhanced drug penetration with evident tissue shrinkage was observed, implying that the system is a highly promising combinatory chemo/hormonal therapeutic platform with efficient synergistic antitumor effects. This new platform designed here integrated real-time tracking, pH-driven drug release, and chemo/hormonal therapy, affording efficacy to potentially treat cancer through enhanced passive targeting and combinatorial therapeutic mechanisms. This is the first report using chemo/hormonal magnetic formulation to systematically study the microparticles' uptake and co-delivery of their cytotoxic agents to different types and stages of human cancerous cells and tumors.

The invention claimed is:

1. An uncoated, spheroidal microparticle drug carrier having an average core diameter in a range of 0.2 to 1.0 μm, comprising small iron oxide nanoparticles having an average core diameter in a range of 2-10 nm,
wherein said microparticle drug carrier does not contain silica; is mesoporous with interconnected pores; has a Brunauer-Emmett-Teller (BET) surface area ($S_{BET}$) in a range of 50-300 m$^2$/g; has a pore volume ($V_{pore}$) in a range of 0.15-0.65 cm$^3$/g; and has an average pore diameter ($d_{pore}$) in a range of 2 to 10 nm; and
wherein said microparticle drug carrier further comprises a combination of anticancer drugs comprising a hydrophilic chemotherapeutic anticancer drug and a hydrophobic hormonal anticancer drug.

2. The microparticle drug carrier of claim 1, wherein the iron oxide nanoparticles comprise maghemite (γ-Fe$_2$O$_3$), hematite (α-Fe$_2$O$_3$), and/or magnetite (Fe$_3$O$_4$).

3. The microparticle drug carrier of claim 1, wherein an amount of the chemotherapeutic anticancer drug released is 4-8 times greater when the microparticle drug carrier is in contact with a medium having a pH in a range of 3.5-5.5 than a medium having a pH in a range of 6.4-8.4.

4. The microparticle drug carrier of claim 1 that is made by a process comprising:
contacting acid-prepared mesoporous silica (APMS) microparticles with an aqueous solution of at least one iron (III) salt selected from the group consisting of FeCl$_3$, Fe(NO$_3$)$_3$, Fe$_2$(SO$_4$)$_3$, and FePO$_4$; and a reducing agent comprising Zn or Mg to produce iron loaded silica particle;
drying and heating the iron loaded silica particle at 300-400° C. under an inert atmosphere to produce an iron oxide impregnated silica particle having an iron oxide within its pores; and
reacting the iron oxide impregnated silica particle with 1 to 10 M NaOH to remove the silica, thus producing the microparticle drug carrier.

5. The microparticle drug carrier of claim 1 wherein the iron is distributed homogenously within the microparticles as depicted by SEM or TEM electron microscopy and/or wherein FTIR spectroscopy shows characteristic absorption bands of iron oxide FeO at 500-600 cm$^{-1}$ and O—K at 3200-3600 cm$^{-1}$ and the disappearance of peaks around 960-1100 cm$^{-1}$ which correspond to Si—O at 1100 cm$^{-1}$ and Si—O—Fe at 960 cm$^{-1}$.

6. The microparticle drug carrier of claim 1, wherein the chemotherapeutic anticancer drug is daunorubicin or doxorubicin and the hormonal anticancer drug is tamoxifen.

7. The microparticle drug carrier of claim 1, wherein the combination of anticancer drugs comprises at least one chemotherapeutic anticancer drug and at least one hormonal anticancer drug selected from the group consisting of doxorubicin, daunorubicin, tamoxifen, nab-paclitaxel, carboplatin, cyclophosphamide, epirubicin, fluorouracil, gemcitabine, eribulin, ixabepilone, methotrexate, mutamycin, mitoxantrone, vinorelbine, paclitaxel, docetaxel, thiotepa, vincristine, cepecitabine, raloxifen, toremifene, anastrozole, exemestane, letrozole, fulvestrant, and combinations thereof.

8. A method of treating a tumor with a combination of anticancer drugs comprising a chemotherapeutic anticancer drug and a hormonal anticancer drug, comprising:
loading the combination of anticancer drugs into the microparticle drug carrier of claim 1 to produce a loaded carrier comprising 1-50 wt % anticancer drugs relative to a total weight of the loaded carrier, and
contacting a tumor with the loaded drug carrier, wherein cancerous cells of the tumor uptake the loaded carrier, and the loaded carrier releases the drugs within the cancerous cells.

9. The method of claim 8, wherein at least one anticancer drug is selected from doxorubicin, daunorubicin, and/or tamoxifen.

10. The method of claim 8, wherein the tumor is a breast tumor or a colorectal tumor.

11. The method of claim 8, wherein a viability of the cancerous cells of the tumor after the contacting is 30-80% lower than a viability of noncancerous cells being contacted by a substantially similar loaded drug carrier.

12. The method of claim 8, wherein the uptake of the loaded drug carrier by the cancerous cells is a factor of 2-10 times greater than an uptake of a similar concentration of loaded carrier brought into contact with a similar concentration of noncancerous cells under substantially similar conditions.

13. The method of claim 8, wherein during the uptake the loaded carrier interacts with a plasma membrane of a cancerous cell of a tumor and is internalized into the cytoplasm of the cancerous cell.

14. The method of claim 9, wherein the tumor is treated with a combination of daunorubicin and tamoxifen,
wherein a viability of the cancerous cells after the contacting is 5-50% of a viability of substantially similar cancerous cells being contacted with a single drug loaded carrier, and/or the drug combination induces more tumor tissue shrinkage than tumor tissue treated with free daunorubicin and tamoxifen.

15. The method of claim 11, wherein the viability of the noncancerous cells after being contacted by the substantially similar loaded carrier is 2-10 times the viability of substantially similar noncancerous cells being contacted with a substantially similar amount of anticancer drug free in a solution.

* * * * *